US009730977B2

(12) United States Patent
Mochly-Rosen et al.

(10) Patent No.: US 9,730,977 B2
(45) Date of Patent: Aug. 15, 2017

(54) INHIBITORS OF MITOCHONDRIAL FISSION AND METHODS OF USE THEREOF

(71) Applicant: The Board of Trustees of the Leland Stanford Junior University, Palo Alto, CA (US)

(72) Inventors: Daria Mochly-Rosen, Menlo Park, CA (US); Xin Qi, Beachwood, OH (US); Nir Qvit, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/988,403

(22) Filed: Jan. 5, 2016

(65) Prior Publication Data

US 2016/0120933 A1    May 5, 2016

Related U.S. Application Data

(63) Continuation of application No. 14/271,301, filed on May 6, 2014, now Pat. No. 9,243,232, which is a continuation of application No. 13/471,221, filed on May 14, 2012, now Pat. No. 8,748,393.

(60) Provisional application No. 61/486,044, filed on May 13, 2011.

(51) Int. Cl.
| | |
|---|---|
| *A61K 38/08* | (2006.01) |
| *G01N 33/573* | (2006.01) |
| *C07K 7/06* | (2006.01) |
| *C07K 14/705* | (2006.01) |
| *C07K 14/00* | (2006.01) |
| *C07K 14/47* | (2006.01) |
| *A61K 38/16* | (2006.01) |
| *C07K 7/08* | (2006.01) |
| *C12N 9/14* | (2006.01) |
| *C12Q 1/34* | (2006.01) |
| *A61K 38/00* | (2006.01) |
| *A61K 51/08* | (2006.01) |

(52) U.S. Cl.
CPC ............ *A61K 38/08* (2013.01); *A61K 38/16* (2013.01); *C07K 7/06* (2013.01); *C07K 7/08* (2013.01); *C07K 14/00* (2013.01); *C07K 14/47* (2013.01); *C07K 14/4722* (2013.01); *C07K 14/705* (2013.01); *C12N 9/14* (2013.01); *C12Q 1/34* (2013.01); *G01N 33/573* (2013.01); *A61K 38/00* (2013.01); *A61K 51/08* (2013.01); *C07K 2319/00* (2013.01); *G01N 2333/4703* (2013.01); *G01N 2333/914* (2013.01); *G01N 2500/02* (2013.01); *G01N 2500/10* (2013.01); *G01N 2500/20* (2013.01)

(58) Field of Classification Search
CPC ........ A61K 38/08; A61K 38/00; A61K 38/16; A61K 51/08; C07K 14/705; C07K 14/00; C07K 14/4722; C07K 2319/00; C07K 7/06; C07K 7/08; C07K 14/47; C12N 9/14; C12Q 1/34; G01N 33/573; G01N 2333/4703; G01N 2333/914; G01N 2500/02; G01N 2500/10; G01N 2500/20
See application file for complete search history.

(56) References Cited

U.S. PATENT DOCUMENTS

| | | |
|---|---|---|
| 5,837,813 A | 11/1998 | Ruoslathi et al. |
| 8,748,393 B2 | 6/2014 | Mochly-Rosen et al. |
| 9,243,232 B2 | 1/2016 | Mochly-Rosen et al. |
| 2007/0044171 A1 | 2/2007 | Kovalic et al. |
| 2008/0287473 A1 | 11/2008 | Nunnari et al. |
| 2013/0053321 A1 | 2/2013 | Mochly-Rosen et al. |
| 2014/0274904 A1 | 9/2014 | Mochly-Rosen et al. |

FOREIGN PATENT DOCUMENTS

| | | |
|---|---|---|
| EP | 1884521 A1 | 2/2008 |
| WO | WO 2008/136869 A2 | 11/2008 |

OTHER PUBLICATIONS

Yoon et al, The Mitochondrial Protein hFis1 Regulates Mitochondrial Fission in Mammalian Cells through an Interaction with the Dynamin-Like Protein DLP1, Molecular and Cellular Biology, 2003, 23, pp. 5409-5420.*
Yu et al, Regulation of mitochondrial fission and apoptosis by the mitochondrial outer membrane protein hFis1, Journal of Cell Science, 2005, 118, pp. 4141-4151.*
Cochran, Antagonists of protein-protein interactions, Chemistry & Biology, 2000, 7, pp. R85-R94.*
Arduino et al., "Mitochondrial fusion/fission, transport and autophagy in Parkinson's disease: When mitochondria get nasty", SAGE-Hindawi Access to Research, Parkinson's Disease, 13 pages (2011).
Barsoum et al., "Nitric oxide-induced mitochondrial fission is regulated by dynamin-related GTPases in neurons", The EMBO Journal, vol. 25, pp. 3900-3911 (2006).

(Continued)

*Primary Examiner* — Julie Ha
*Assistant Examiner* — Li Ni Komatsu
(74) *Attorney, Agent, or Firm* — Judy Mohr; McDermott Will & Emery LLP

(57) ABSTRACT

The present disclosure provides peptides and constructs that inhibit mitochondrial fission, and compositions comprising the peptides or constructs. The present disclosure provides methods of reducing abnormal mitochondrial fission in a cell. Also provided are methods for designing and validating mitochondrial fission inhibitor constructs and peptides, including but not limited to, evaluating the effects of the constructs and peptides on binding of dynamin-1-related protein (Drp1) GTPase activity, Drp1 to mitochondrial fission 1 protein (Fis1), reduction of mitochondrial damage, reduction in cell death, inhibition of mitochondrial fragmentation in a cell under pathological conditions, and reduced loss of neurites in primary dopaminergic neurons in a Parkinsonism cell culture.

8 Claims, 23 Drawing Sheets

(56) References Cited

OTHER PUBLICATIONS

Berendsen, "A glimps of the holy grail", Science, vol. 282, No. 5389, pp. 642-643 (1998).
Bradley et al., "Limits of cooperativity in a structurally modular protein: Response of the notch ankyrin domain to analogous alanine substitutions in each repeat", J. Mol. Biol., vol. 324, pp. 373-386 (2002).
Chan, "Mitochondria: dynamic organelles in disease, aging, and development", Cell, vol. 125, pp. 1241-1252 (2006).
Costa et al., "Mitochondrial fission and cristae disruption increase the response of cell models of Huntington's disease to apoptotic stimuli", EMBO Mol. Med., vol. 2, pp. 490-503 (2010).
Cui et al., "Perturbations in mitochondrial dynamics induced by human mutant PINK1 can be rescued by the mitochondrial division inhibitor mdivi-1", J. Biol. Chem., vol. 285, No. 15, pp. 11740-11752 (2010).
Deng et al., "The Parkinson's disease genes pink1 and parkin promote mitochondrial fission and/or inhibit fusion in *Drosophilia*", PNAS USA, vol. 105, No. 38, pp. 14503-14508 (2008).
Ferrari et al., "Role of Drp1, a key mitochondrial fission protein, in neuropathic pain", The Journal of Neuroscience, vol. 31, No. 31, pp. 11404-14110 (2011).
International Search Report from PCT Patent Application No. PCT/US2012/037800 mailed on Nov. 23, 2012.
James et al., "hFis1, a novel component of the mammalian mitochondrial fission machinery", J. Biol. Chem., vol. 278, No. 38, pp. 36373-36379 (2003).
Kageyama et al., "Mitochondrial division: molecular machinery and physiological functions", Curr. Opin. Cell. Biol., vol. 23, No. 4, pp. 427-434 (2011).
Knott et al., "Mitochondrial fragmentation in neurodegeneration", Nat. Rev Neurosci., vol. 9, No. 7, pp. 505-518 (2008).
Ngo et al., "Computational complexity, protein structure protection and the levinthal paradox", The Protein Folding Problem and Tertiary Structure Prediction, Merz and Le Grand, Ed., Birkhauser, Boston, Chapter 14, pp. 491-494 (1994).
Palaniyandi et al., "Regulation of mitochondrial processes: a target for heart failure", Drug Discov. Today Dis. Mech., vol. 7, No. 2, pp. e95-e102 (2010).
Parone et al., "Inhibiting the mitochondrial fission machinery does not prevent Bax/Bak-dependent apoptosis", Mol. Cell. Biol., vol. 26, No. 20, pp. 7397-7408 (2006).
Qi et al., "Aberrant mitochondrial fission in neurons induced by protein kinase Cd under oxidative stress conditions in vivo", Molecular Biology of the Cell, vol. 22, pp. 256-265 (2011).
Ron and Mochly-Rosen, "An autoregulatory region in protein in kinase C: The psuedoanchoring site", PNAS USA, vol. 92, pp. 492-496 (1995).
Rudinger, "Characteristics of the amino acids as components of a peptide hormone sequence", Peptide Hormones, J.A. Parsons, Ed., National Institute for Medical Research Mill Hill, London, University Park Press, pp. 1-7 (1976).
Sigma Genosys, "Designing Custom Peptides, Technical Bulletin", Custom Peptide Synthesis, 2 pages, Online article downloaded from http://www.sigma-genosys.com/peptide_design.asp (2004).
Smirnova et al., "Dynamin-related protein Drp1 is required for mitochondrial division in mammalian cells", Mol. Biol. Cell, vol. 12, No. 8, pp. 2245-2256 (2001).
Species ELLPRGS STIC search result, Title: US-14-271-301-301-12D1E, 1 page, Accessed Apr. 7, 2015.
Suzuki et al., "Novel structure of the N terminus in yeast Fis1 correlates with a specialized function in mitochondrial fission", J. Biol. Chem., vol. 280, No. 22, pp. 21444-21452 (2005).
Twig et al., "Fission and selective fusion govern mitochondrial segregation and elimination by autophagy", The EMBO J., vol. 27, pp. 433-446 (2008).
UniProt, X6LRD4-X6LRD4_RETFI, Protein: Uncharacterized protein, Gene: RFI_33456, Organism: Reticulomyxa filose, Online article downloaded from http://www.uniprot.org/uniprot/X6LRD4, 3 pages, Accessed Apr. 10, 2015.
UniProtKB/Swiss-Prot., Accession No. O00429.2, "Dynamin-1-like protein", Online article downloaded from http://www.ncbi.nlm.nih.gov/protein/O00429.3, 26 pages, Accessed Apr. 10, 2015.
Van Der Bliek et al., "Mutations in human dynamin block an intermediate stage in coated vesicle formation", J. Cell Biol., vol. 122, No. 3, pp. 553-563 (1993).
Voet et al., "Abnormal Hemoglobins", Biochemistry, John Wiley & Sons, Inc., pp. 235-241 (1995).

\* cited by examiner

| | GenBank Acc # | | | SEQ ID NO |
|---|---|---|---|---|
| 108 | | STQELLRFPK | | 10 |
| Human-DNM1L | O00429 | QRIIQHCSNYSTQELLRFPKLHDAIVEVVTC | 470 | 55 |
| Rat-DNM1L | O35303 | QRIIQHCSNYSTQELLRFPKLHDAIVEVVTC | 483 | 56 |
| Mouse-DNM1L | Q8K1M6 | QRIIQHCSNYSTQELLRFPKLHDAIVEVVTC | 476 | 57 |
| Chick-DNM1L | E1BV15 | INTVRQCT----KKLSQYPHLREEMERIVTT | 462 | 58 |
| Darne-DNM1L | E9QF63 | VNTVRQCT----KKLAQYPMLREEMERIVTQ | 462 | 59 |
| | | :::*: :* ::* *:: :** | | |
| 109 | | KLSAREQRD | | 11 |
| Human-DNM1L | O00429 | LLDVPVPVARKLSAREQRDCEVIERLI | 651 | 55 |
| Rat-DNM1L | O35303 | LLDVPVPVARKLSAREQRDCEVIERLI | 670 | 56 |
| Mouse-DNM1L | Q8K1M6 | LLDVPVPVARKLSAREQRDCEVIERLI | 657 | 57 |
| Chick-DNM1L | E1BV15 | -ENGSDSFMHSMDPQLERQVETIRNLV | 666 | 58 |
| Darne-DNM1L | E9QF63 | DESSSDGFMHSMDPQLERQVETIRNLV | 667 | 59 |
| | | : :*: * * *: | | |
| 110 | | DLLPRGS | | 12 |
| Human-DNM1L | O00429 | SVLESLVGRDLLPRGTGIVTRRPLILQLVH | 69 | 55 |
| Rat-DNM1L | O35303 | SVLESLVGRDLLPRGTGVVTRRPLILQLVH | 69 | 56 |
| Mouse-DNM1L | Q8K1M6 | SVLESLVGRDLLPRGTGVVTRRPLILQLVH | 69 | 57 |
| Chick-DNM1L | E1BV15 | SVLENFVGRDFLPRGSGIVTRRPLVLQLVN | 76 | 58 |
| Darne-DNM1L | E9QF63 | SVLENFVGKDFLPRGSGIVTRRPLVLQLIN | 76 | 59 |
| | | **::*:****:*:***:*:: | | |
| 111 | | SVEDLLKFEK | | 60 |
| Human-FIS1 | Q9Y3D6 | MEAVLNELVSVEDLLKFEKKFQSEKAAGSV | 30 | 61 |
| Rat-FIS1 | P84817 | MEAVLNELVSVEDLKNFERKFQSEQAAGSV | 30 | 62 |
| Mouse-FIS1 | Q9CQ92 | MEAVLNELVSVEDLKNFERKFQSEQAAGSV | 30 | 63 |
| Darne-FIS1 | E9QGI1 | MEAVVSDIVAPEDLKKFEKKYNAELVKGPV | 30 | 64 |
| | | ****: ::* *** :**:*:::* * * | | |
| 112 | | KGSKEEQRD | | 15 |
| Human-FIS1 | Q9Y3D6 | IRKGIVLLEELLPKGSKEEQRDYVFYLAVG | 80 | 61 |
| Rat-FIS1 | P84817 | IRRGIVLLEELLPKGSKEEQRDYVFYLAVG | 80 | 62 |
| Mouse-FIS1 | Q9CQ92 | IRRGIVLLEELLPKGSKEEQRDYVFYLAVG | 80 | 63 |
| Darne-FIS1 | E9QGI1 | IVKGIQLLEELVHTSKKDDQRDFLFYLAVA | 80 | 64 |
| | | * : ***: *::*::*** | | |
| 113 | | ELLPKGS | | 16 |
| Human-FIS1 | Q9Y3D6 | IRKGIVLLEELLPKGSKEEQRDYVFYLAVG | 80 | 61 |
| Rat-FIS1 | P84817 | IRRGIVLLEELLPKGSKEEQRDYVFYLAVG | 80 | 62 |
| Mouse-FIS1 | Q9CQ92 | IRRGIVLLEELLPKGSKEEQRDYVFYLAVG | 80 | 63 |
| Darne-FIS1 | E9QGI1 | IVKGIQLLEELVHTSKKDDQRDFLFYLAVA | 80 | 64 |
| | | * : ***: *::*::*** | | |

FIG. 1C

```
                            SEQUENCE LISTING

<160> NUMBER OF SEQ ID NOS: 62

<210> SEQ ID NO 1
<211> LENGTH: 710
<212> TYPE: PRT
<213> ORGANISM: Homo sapiens

<400> SEQUENCE: 1

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Val Gly
            20                  25                  30

Thr Gln Ser Ser Gly Lys Ser Ser Val Leu Glu Ser Leu Val Gly Arg
        35                  40                  45

Asp Leu Leu Pro Arg Gly Thr Gly Ile Val Thr Arg Arg Pro Leu Ile
    50                  55                  60

Leu Gln Leu Val His Val Ser Gln Glu Asp Lys Arg Lys Thr Thr Gly
65                  70                  75                  80

Glu Glu Asn Gly Val Glu Ala Glu Glu Trp Gly Lys Phe Leu His Thr
                85                  90                  95

Lys Asn Lys Leu Tyr Thr Asp Phe Asp Glu Ile Arg Gln Glu Ile Glu
            100                 105                 110

Asn Glu Thr Glu Arg Ile Ser Gly Asn Asn Lys Gly Val Ser Pro Glu
        115                 120                 125

Pro Ile His Leu Lys Ile Phe Ser Pro Asn Val Val Asn Leu Thr Leu
    130                 135                 140

Val Asp Leu Pro Gly Met Thr Lys Val Pro Val Gly Asp Gln Pro Lys
145                 150                 155                 160

Asp Ile Glu Leu Gln Ile Arg Glu Leu Ile Leu Arg Phe Ile Ser Asn
                165                 170                 175

Pro Asn Ser Ile Ile Leu Ala Val Thr Ala Ala Asn Thr Asp Met Ala
            180                 185                 190

Thr Ser Glu Ala Leu Lys Ile Ser Arg Glu Val Asp Pro Asp Gly Arg
        195                 200                 205

Arg Thr Leu Ala Val Ile Thr Lys Leu Asp Leu Met Asp Ala Gly Thr
    210                 215                 220

Asp Ala Met Asp Val Leu Met Gly Arg Val Ile Pro Val Lys Leu Gly
225                 230                 235                 240

Ile Ile Gly Val Val Asn Arg Ser Gln Leu Asp Ile Asn Asn Lys Lys
                245                 250                 255

Ser Val Thr Asp Ser Ile Arg Asp Glu Tyr Ala Phe Leu Gln Lys Lys
            260                 265                 270

Tyr Pro Ser Leu Ala Asn Arg Asn Gly Thr Lys Tyr Leu Ala Arg Thr
```

```
            275                 280                 285
Leu Asn Arg Leu Leu Met His His Ile Arg Asp Cys Leu Pro Glu Leu
290                 295                 300
Lys Thr Arg Ile Asn Val Leu Ala Ala Gln Tyr Gln Ser Leu Leu Asn
305                 310                 315                 320
Ser Tyr Gly Glu Pro Val Asp Asp Lys Ser Ala Thr Leu Leu Gln Leu
                325                 330                 335
Ile Thr Lys Phe Ala Thr Glu Tyr Cys Asn Thr Ile Glu Gly Thr Ala
            340                 345                 350
Lys Tyr Ile Glu Thr Ser Glu Leu Cys Gly Gly Ala Arg Ile Cys Tyr
        355                 360                 365
Ile Phe His Glu Thr Phe Gly Arg Thr Leu Glu Ser Val Asp Pro Leu
370                 375                 380
Gly Gly Leu Asn Thr Ile Asp Ile Leu Thr Ala Ile Arg Asn Ala Thr
385                 390                 395                 400
Gly Pro Arg Pro Ala Leu Phe Val Pro Glu Val Ser Phe Glu Leu Leu
                405                 410                 415
Val Lys Arg Gln Ile Lys Arg Leu Glu Glu Pro Ser Leu Arg Cys Val
            420                 425                 430
Glu Leu Val His Glu Glu Met Gln Arg Ile Ile Gln His Cys Ser Asn
        435                 440                 445
Tyr Ser Thr Gln Glu Leu Leu Arg Phe Pro Lys Leu His Asp Ala Ile
450                 455                 460
Val Glu Val Val Thr Cys Leu Leu Arg Lys Arg Leu Pro Val Thr Asn
465                 470                 475                 480
Glu Met Val His Asn Leu Val Ala Ile Glu Leu Ala Tyr Ile Asn Thr
                485                 490                 495
Lys His Pro Asp Phe Ala Asp Ala Cys Gly Leu Met Asn Asn Asn Ile
            500                 505                 510
Glu Glu Gln Arg Arg Asn Arg Leu Ala Arg Glu Leu Pro Ser Ala Val
        515                 520                 525
Ser Arg Asp Lys Leu Ile Gln Asp Ser Arg Arg Glu Thr Lys Asn Val
530                 535                 540
Ala Ser Gly Gly Gly Val Gly Asp Gly Val Gln Glu Pro Thr Thr
545                 550                 555                 560
Gly Asn Trp Arg Gly Met Leu Lys Thr Ser Lys Ala Glu Glu Leu Leu
                565                 570                 575
Ala Glu Glu Lys Ser Lys Pro Ile Pro Ile Met Pro Ala Ser Pro Gln
            580                 585                 590
Lys Gly His Ala Val Asn Leu Leu Asp Val Pro Val Pro Val Ala Arg
        595                 600                 605
Lys Leu Ser Ala Arg Glu Gln Arg Asp Cys Glu Val Ile Glu Arg Leu
610                 615                 620
Ile Lys Ser Tyr Phe Leu Ile Val Arg Lys Asn Ile Gln Asp Ser Val
625                 630                 635                 640
Pro Lys Ala Val Met His Phe Leu Val Asn His Val Lys Asp Thr Leu
                645                 650                 655
Gln Ser Glu Leu Val Gly Gln Leu Tyr Lys Ser Ser Leu Leu Asp Asp
            660                 665                 670
Leu Leu Thr Glu Ser Glu Asp Met Ala Gln Arg Arg Lys Glu Ala Ala
        675                 680                 685
Asp Met Leu Lys Ala Leu Gln Gly Ala Ser Gln Ile Ile Ala Glu Ile
690                 695                 700
```

```
Arg Glu Thr His Leu Trp
705             710

<210> SEQ ID NO 2
<211> LENGTH: 152
<212> TYPE: PRT
<213> ORGANISM: Homo sapiens

<400> SEQUENCE: 2

Met Glu Ala Val Leu Asn Glu Leu Val Ser Val Glu Asp Leu Leu Lys
1               5                   10                  15

Phe Glu Lys Lys Phe Gln Ser Glu Lys Ala Ala Gly Ser Val Ser Lys
                20                  25                  30

Ser Thr Gln Phe Glu Tyr Ala Trp Cys Leu Val Arg Ser Lys Tyr Asn
            35                  40                  45

Asp Asp Ile Arg Lys Gly Ile Val Leu Leu Glu Glu Leu Leu Pro Lys
        50                  55                  60

Gly Ser Lys Glu Glu Gln Arg Asp Tyr Val Phe Tyr Leu Ala Val Gly
65                  70                  75                  80

Asn Tyr Arg Leu Lys Glu Tyr Glu Lys Ala Leu Lys Tyr Val Arg Gly
                85                  90                  95

Leu Leu Gln Thr Glu Pro Gln Asn Asn Gln Ala Lys Glu Leu Glu Arg
                100                 105                 110

Leu Ile Asp Lys Ala Met Lys Lys Asp Gly Leu Val Gly Met Ala Ile
            115                 120                 125

Val Gly Gly Met Ala Leu Gly Val Ala Gly Leu Ala Gly Leu Ile Gly
        130                 135                 140

Leu Ala Val Ser Lys Ser Lys Ser
145                 150

<210> SEQ ID NO 3
<211> LENGTH: 7
<212> TYPE: PRT
<213> ORGANISM: Artificial sequence
<220> FEATURE:
<223> OTHER INFORMATION: Synthetic peptide

<400> SEQUENCE: 3

Asp Leu Leu Pro Arg Gly Thr
1               5

<210> SEQ ID NO 4
<211> LENGTH: 10
<212> TYPE: PRT
<213> ORGANISM: Artificial sequence
<220> FEATURE:
<223> OTHER INFORMATION: Synthetic peptide

<400> SEQUENCE: 4

Ser Thr Gln Glu Leu Leu Arg Phe Pro Lys
1               5                   10

<210> SEQ ID NO 5
<211> LENGTH: 9
<212> TYPE: PRT
<213> ORGANISM: Artificial sequence
<220> FEATURE:
<223> OTHER INFORMATION: Synthetic peptide

<400> SEQUENCE: 5

Lys Ser Leu Ala Arg Glu Gln Arg Asp
```

```
<210> SEQ ID NO 6
<211> LENGTH: 7
<212> TYPE: PRT
<213> ORGANISM: Artificial sequence
<220> FEATURE:
<223> OTHER INFORMATION: Synthetic peptide

<400> SEQUENCE: 6

Glu Leu Leu Pro Lys Gly Ser
1               5

<210> SEQ ID NO 7
<211> LENGTH: 10
<212> TYPE: PRT
<213> ORGANISM: Artificial sequence
<220> FEATURE:
<223> OTHER INFORMATION: Synthetic peptide

<400> SEQUENCE: 7

Ser Val Glu Asp Leu Leu Lys Phe Glu Lys
1               5                   10

<210> SEQ ID NO 8
<211> LENGTH: 9
<212> TYPE: PRT
<213> ORGANISM: Artificial sequence
<220> FEATURE:
<223> OTHER INFORMATION: Synthetic peptide

<400> SEQUENCE: 8

Lys Gly Ser Lys Glu Glu Gln Arg Asp
1               5

<210> SEQ ID NO 9
<211> LENGTH: 736
<212> TYPE: PRT
<213> ORGANISM: Homo sapiens

<400> SEQUENCE: 9

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Gly
            20                  25                  30

Thr Gln Ser Ser Gly Lys Ser Ser Val Leu Glu Ser Leu Val Gly Arg
        35                  40                  45

Asp Leu Leu Pro Arg Gly Thr Gly Ile Val Thr Arg Arg Pro Leu Ile
    50                  55                  60

Leu Gln Leu Val His Val Ser Gln Glu Asp Lys Arg Lys Thr Thr Gly
65                  70                  75                  80

Glu Glu Asn Gly Val Glu Ala Glu Glu Trp Gly Lys Phe Leu His Thr
                85                  90                  95

Lys Asn Lys Leu Tyr Thr Asp Phe Asp Glu Ile Arg Gln Glu Ile Glu
            100                 105                 110

Asn Glu Thr Glu Arg Ile Ser Gly Asn Asn Lys Gly Val Ser Pro Glu
        115                 120                 125

Pro Ile His Leu Lys Ile Phe Ser Pro Asn Val Val Asn Leu Thr Leu
    130                 135                 140

Val Asp Leu Pro Gly Met Thr Lys Val Pro Val Gly Asp Gln Pro Lys
145                 150                 155                 160
```

-continued

Asp Ile Glu Leu Gln Ile Arg Glu Leu Ile Leu Arg Phe Ile Ser Asn
            165                 170                 175

Pro Asn Ser Ile Ile Leu Ala Val Thr Ala Ala Asn Thr Asp Met Ala
            180                 185                 190

Thr Ser Glu Ala Leu Lys Ile Ser Arg Glu Val Asp Pro Asp Gly Arg
            195                 200                 205

Arg Thr Leu Ala Val Ile Thr Lys Leu Asp Leu Met Asp Ala Gly Thr
            210                 215                 220

Asp Ala Met Asp Val Leu Met Gly Arg Val Ile Pro Val Lys Leu Gly
225                 230                 235                 240

Ile Ile Gly Val Val Asn Arg Ser Gln Leu Asp Ile Asn Asn Lys Lys
                245                 250                 255

Ser Val Thr Asp Ser Ile Arg Asp Glu Tyr Ala Phe Leu Gln Lys Lys
                260                 265                 270

Tyr Pro Ser Leu Ala Asn Arg Asn Gly Thr Lys Tyr Leu Ala Arg Thr
            275                 280                 285

Leu Asn Arg Leu Leu Met His His Ile Arg Asp Cys Leu Pro Glu Leu
            290                 295                 300

Lys Thr Arg Ile Asn Val Leu Ala Ala Gln Tyr Gln Ser Leu Leu Asn
305                 310                 315                 320

Ser Tyr Gly Glu Pro Val Asp Asp Lys Ser Ala Thr Leu Leu Gln Leu
                325                 330                 335

Ile Thr Lys Phe Ala Thr Glu Tyr Cys Asn Thr Ile Glu Gly Thr Ala
                340                 345                 350

Lys Tyr Ile Glu Thr Ser Glu Leu Cys Gly Gly Ala Arg Ile Cys Tyr
            355                 360                 365

Ile Phe His Glu Thr Phe Gly Arg Thr Leu Glu Ser Val Asp Pro Leu
            370                 375                 380

Gly Gly Leu Asn Thr Ile Asp Ile Leu Thr Ala Ile Arg Asn Ala Thr
385                 390                 395                 400

Gly Pro Arg Pro Ala Leu Phe Val Pro Glu Val Ser Phe Glu Leu Leu
                405                 410                 415

Val Lys Arg Gln Ile Lys Arg Leu Glu Glu Pro Ser Leu Arg Cys Val
                420                 425                 430

Glu Leu Val His Glu Met Gln Arg Ile Ile Gln His Cys Ser Asn
            435                 440                 445

Tyr Ser Thr Gln Glu Leu Leu Arg Phe Pro Lys Leu His Asp Ala Ile
            450                 455                 460

Val Glu Val Val Thr Cys Leu Leu Arg Lys Arg Leu Pro Val Thr Asn
465                 470                 475                 480

Glu Met Val His Asn Leu Val Ala Ile Glu Leu Ala Tyr Ile Asn Thr
                485                 490                 495

Lys His Pro Asp Phe Ala Asp Ala Cys Gly Leu Met Asn Asn Asn Ile
            500                 505                 510

Glu Glu Gln Arg Arg Asn Arg Leu Ala Arg Glu Leu Pro Ser Ala Val
            515                 520                 525

Ser Arg Asp Lys Ser Ser Lys Val Pro Ser Ala Leu Ala Pro Ala Ser
            530                 535                 540

Gln Glu Pro Ser Pro Ala Ala Ser Ala Glu Ala Asp Gly Lys Leu Ile
545                 550                 555                 560

Gln Asp Ser Arg Arg Glu Thr Lys Asn Val Ala Ser Gly Gly Gly Gly
                565                 570                 575

Val Gly Asp Gly Val Gln Glu Pro Thr Thr Gly Asn Trp Arg Gly Met

```
                    580                 585                 590
Leu Lys Thr Ser Lys Ala Glu Glu Leu Leu Ala Glu Glu Lys Ser Lys
                595                 600                 605

Pro Ile Pro Ile Met Pro Ala Ser Pro Gln Lys Gly His Ala Val Asn
            610                 615                 620

Leu Leu Asp Val Pro Val Pro Val Ala Arg Lys Leu Ser Ala Arg Glu
625                 630                 635                 640

Gln Arg Asp Cys Glu Val Ile Glu Arg Leu Ile Lys Ser Tyr Phe Leu
                645                 650                 655

Ile Val Arg Lys Asn Ile Gln Asp Ser Val Pro Lys Ala Val Met His
                660                 665                 670

Phe Leu Val Asn His Val Lys Asp Thr Leu Gln Ser Glu Leu Val Gly
            675                 680                 685

Gln Leu Tyr Lys Ser Ser Leu Leu Asp Asp Leu Leu Thr Glu Ser Glu
            690                 695                 700

Asp Met Ala Gln Arg Arg Lys Glu Ala Ala Asp Met Leu Lys Ala Leu
705                 710                 715                 720

Gln Gly Ala Ser Gln Ile Ile Ala Glu Ile Arg Glu Thr His Leu Trp
                725                 730                 735

<210> SEQ ID NO 10
<211> LENGTH: 10
<212> TYPE: PRT
<213> ORGANISM: Artificial sequence
<220> FEATURE:
<223> OTHER INFORMATION: Synthetic peptide

<400> SEQUENCE: 10

Ser Thr Gln Glu Leu Leu Arg Phe Pro Lys
1               5                   10

<210> SEQ ID NO 11
<211> LENGTH: 9
<212> TYPE: PRT
<213> ORGANISM: Artificial sequence
<220> FEATURE:
<223> OTHER INFORMATION: Synthetic peptide

<400> SEQUENCE: 11

Lys Leu Ser Ala Arg Glu Gln Arg Asp
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic peptide

<400> SEQUENCE: 12

Asp Leu Leu Pro Arg Gly Ser
1               5

<210> SEQ ID NO 13
<211> LENGTH: 7
<212> TYPE: PRT
<213> ORGANISM: Artificial sequence
<220> FEATURE:
<223> OTHER INFORMATION: Synthetic peptide

<400> SEQUENCE: 13

Asp Leu Leu Pro Arg Gly Thr
```

```
1               5

<210> SEQ ID NO 14
<211> LENGTH: 11
<212> TYPE: PRT
<213> ORGANISM: Artificial sequence
<220> FEATURE:
<223> OTHER INFORMATION: Synthetic peptide

<400> SEQUENCE: 14

Cys Ser Val Glu Asp Leu Leu Lys Phe Glu Lys
1               5                   10

<210> SEQ ID NO 15
<211> LENGTH: 9
<212> TYPE: PRT
<213> ORGANISM: Artificial sequence
<220> FEATURE:
<223> OTHER INFORMATION: Synthetic peptide

<400> SEQUENCE: 15

Lys Gly Ser Lys Glu Glu Gln Arg Asp
1               5

<210> SEQ ID NO 16
<211> LENGTH: 7
<212> TYPE: PRT
<213> ORGANISM: Artificial sequence
<220> FEATURE:
<223> OTHER INFORMATION: Synthetic peptide

<400> SEQUENCE: 16

Glu Leu Leu Pro Lys Gly Ser
1               5

<210> SEQ ID NO 17
<211> LENGTH: 23
<212> TYPE: PRT
<213> ORGANISM: Artificial sequence
<220> FEATURE:
<223> OTHER INFORMATION: Synthetic peptide

<400> SEQUENCE: 17

Arg Arg Arg Gln Arg Arg Lys Lys Arg Gly Tyr Gly Gly Ser Thr Gln
1               5                   10                  15

Glu Leu Leu Arg Phe Pro Lys
            20

<210> SEQ ID NO 18
<211> LENGTH: 22
<212> TYPE: PRT
<213> ORGANISM: Artificial sequence
<220> FEATURE:
<223> OTHER INFORMATION: Synthetic peptide

<400> SEQUENCE: 18

Arg Arg Arg Gln Arg Arg Lys Lys Arg Gly Tyr Gly Gly Lys Leu Ser
1               5                   10                  15

Ala Arg Glu Gln Arg Asp
            20

<210> SEQ ID NO 19
<211> LENGTH: 20
<212> TYPE: PRT
<213> ORGANISM: Artificial sequence
<220> FEATURE:
```

<223> OTHER INFORMATION: Synthetic peptide

<400> SEQUENCE: 19

Arg Arg Arg Gln Arg Arg Lys Lys Arg Gly Tyr Gly Gly Asp Leu Leu
1               5                   10                  15

Pro Arg Gly Ser
            20

<210> SEQ ID NO 20
<211> LENGTH: 20
<212> TYPE: PRT
<213> ORGANISM: Artificial sequence
<220> FEATURE:
<223> OTHER INFORMATION: Synthetic peptide

<400> SEQUENCE: 20

Arg Arg Arg Gln Arg Arg Lys Lys Arg Gly Tyr Gly Gly Asp Leu Leu
1               5                   10                  15

Pro Arg Gly Thr
            20

<210> SEQ ID NO 21
<211> LENGTH: 24
<212> TYPE: PRT
<213> ORGANISM: Artificial sequence
<220> FEATURE:
<223> OTHER INFORMATION: Synthetic peptide

<400> SEQUENCE: 21

Arg Arg Arg Gln Arg Arg Lys Lys Arg Gly Tyr Gly Gly Cys Ser Val
1               5                   10                  15

Glu Asp Leu Leu Lys Phe Glu Lys
            20

<210> SEQ ID NO 22
<211> LENGTH: 22
<212> TYPE: PRT
<213> ORGANISM: Artificial sequence
<220> FEATURE:
<223> OTHER INFORMATION: Synthetic peptide

<400> SEQUENCE: 22

Arg Arg Arg Gln Arg Arg Lys Lys Arg Gly Tyr Gly Gly Lys Gly Ser
1               5                   10                  15

Lys Glu Glu Gln Arg Asp
            20

<210> SEQ ID NO 23
<211> LENGTH: 20
<212> TYPE: PRT
<213> ORGANISM: Artificial sequence
<220> FEATURE:
<223> OTHER INFORMATION: Synthetic peptide

<400> SEQUENCE: 23

Arg Arg Arg Gln Arg Arg Lys Lys Arg Gly Tyr Gly Gly Glu Leu Leu
1               5                   10                  15

Pro Lys Gly Ser
            20

<210> SEQ ID NO 24
<211> LENGTH: 20
<212> TYPE: PRT
<213> ORGANISM: Artificial sequence
<220> FEATURE:
<223> OTHER INFORMATION: Synthetic peptide

<400> SEQUENCE: 24

Tyr Gly Arg Lys Lys Arg Arg Gln Arg Arg Gly Gly Ala Leu Leu
1               5                   10                  15

Pro Arg Gly Ser
            20

<210> SEQ ID NO 25
<211> LENGTH: 20
<212> TYPE: PRT
<213> ORGANISM: Artificial sequence
<220> FEATURE:
<223> OTHER INFORMATION: Synthetic peptide

<400> SEQUENCE: 25

Tyr Gly Arg Lys Lys Arg Arg Gln Arg Arg Gly Gly Asp Ala Leu
1               5                   10                  15

Pro Arg Gly Ser
            20

<210> SEQ ID NO 26
<211> LENGTH: 20
<212> TYPE: PRT
<213> ORGANISM: Artificial sequence
<220> FEATURE:
<223> OTHER INFORMATION: Synthetic peptide

<400> SEQUENCE: 26

Tyr Gly Arg Lys Lys Arg Arg Gln Arg Arg Gly Gly Asp Leu Ala
1               5                   10                  15

Pro Arg Gly Ser
            20

<210> SEQ ID NO 27
<211> LENGTH: 20
<212> TYPE: PRT
<213> ORGANISM: Artificial sequence
<220> FEATURE:
<223> OTHER INFORMATION: Synthetic peptide

<400> SEQUENCE: 27

Tyr Gly Arg Lys Lys Arg Arg Gln Arg Arg Gly Gly Asp Leu Leu
1               5                   10                  15

Ala Arg Gly Ser
            20

<210> SEQ ID NO 28
<211> LENGTH: 20
<212> TYPE: PRT
<213> ORGANISM: Artificial sequence
<220> FEATURE:
<223> OTHER INFORMATION: Synthetic peptide

<400> SEQUENCE: 28

Tyr Gly Arg Lys Lys Arg Arg Gln Arg Arg Gly Gly Asp Leu Leu
1               5                   10                  15

Pro Ala Gly Ser
            20

<210> SEQ ID NO 29
<211> LENGTH: 20
<212> TYPE: PRT

```
<213> ORGANISM: Artificial sequence
<220> FEATURE:
<223> OTHER INFORMATION: Synthetic peptide

<400> SEQUENCE: 29

Tyr Gly Arg Lys Lys Arg Arg Gln Arg Arg Gly Gly Asp Leu Leu
1               5                   10                  15

Pro Arg Ala Ser
            20

<210> SEQ ID NO 30
<211> LENGTH: 20
<212> TYPE: PRT
<213> ORGANISM: Artificial sequence
<220> FEATURE:
<223> OTHER INFORMATION: Synthetic peptide

<400> SEQUENCE: 30

Tyr Gly Arg Lys Lys Arg Arg Gln Arg Arg Gly Gly Asp Leu Leu
1               5                   10                  15

Pro Arg Gly Ala
            20

<210> SEQ ID NO 31
<211> LENGTH: 11
<212> TYPE: PRT
<213> ORGANISM: Artificial sequence
<220> FEATURE:
<223> OTHER INFORMATION: Synthetic peptide

<400> SEQUENCE: 31

Tyr Gly Arg Lys Lys Arg Arg Gln Arg Arg
1               5                   10

<210> SEQ ID NO 32
<211> LENGTH: 11
<212> TYPE: PRT
<213> ORGANISM: Artificial sequence
<220> FEATURE:
<223> OTHER INFORMATION: Synthetic peptide

<400> SEQUENCE: 32

Arg Arg Arg Gln Arg Arg Lys Lys Arg Gly Tyr
1               5                   10

<210> SEQ ID NO 33
<211> LENGTH: 12
<212> TYPE: PRT
<213> ORGANISM: Artificial sequence
<220> FEATURE:
<223> OTHER INFORMATION: Synthetic peptide

<400> SEQUENCE: 33

Arg Arg Gln Arg Arg Thr Ser Lys Leu Met Lys Arg
1               5                   10

<210> SEQ ID NO 34
<211> LENGTH: 27
<212> TYPE: PRT
<213> ORGANISM: Artificial sequence
<220> FEATURE:
<223> OTHER INFORMATION: Synthetic peptide

<400> SEQUENCE: 34

Gly Trp Thr Leu Asn Ser Ala Gly Tyr Leu Leu Gly Lys Ile Asn Leu
1               5                   10                  15
```

```
Lys Ala Leu Ala Ala Leu Ala Lys Lys Ile Leu
            20                  25
```

```
<210> SEQ ID NO 35
<211> LENGTH: 33
<212> TYPE: PRT
<213> ORGANISM: Artificial sequence
<220> FEATURE:
<223> OTHER INFORMATION: Synthetic peptide

<400> SEQUENCE: 35

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala
```

```
<210> SEQ ID NO 36
<211> LENGTH: 16
<212> TYPE: PRT
<213> ORGANISM: Artificial sequence
<220> FEATURE:
<223> OTHER INFORMATION: Synthetic peptide

<400> SEQUENCE: 36

Arg Gln Ile Lys Ile Trp Phe Gln Asn Arg Arg Met Lys Trp Lys Lys
1               5                   10                  15
```

```
<210> SEQ ID NO 37
<211> LENGTH: 11
<212> TYPE: PRT
<213> ORGANISM: Artificial sequence
<220> FEATURE:
<223> OTHER INFORMATION: Synthetic peptide

<400> SEQUENCE: 37

Tyr Gly Arg Lys Lys Arg Arg Gln Arg Arg Arg
1               5                   10
```

```
<210> SEQ ID NO 38
<211> LENGTH: 11
<212> TYPE: PRT
<213> ORGANISM: Artificial sequence
<220> FEATURE:
<223> OTHER INFORMATION: Synthetic peptide

<400> SEQUENCE: 38

Arg Arg Arg Gln Arg Arg Lys Lys Arg Gly Tyr
1               5                   10
```

```
<210> SEQ ID NO 39
<211> LENGTH: 9
<212> TYPE: PRT
<213> ORGANISM: Artificial sequence
<220> FEATURE:
<223> OTHER INFORMATION: Synthetic peptide

<400> SEQUENCE: 39

Arg Lys Lys Arg Arg Gln Arg Arg Arg
1               5
```

```
<210> SEQ ID NO 40
<211> LENGTH: 11
<212> TYPE: PRT
<213> ORGANISM: Artificial sequence
```

<220> FEATURE:
<223> OTHER INFORMATION: Synthetic peptide

<400> SEQUENCE: 40

Tyr Gly Arg Lys Lys Arg Arg Gln Arg Arg Arg
1               5                   10

<210> SEQ ID NO 41
<211> LENGTH: 11
<212> TYPE: PRT
<213> ORGANISM: Artificial sequence
<220> FEATURE:
<223> OTHER INFORMATION: Synthetic peptide

<400> SEQUENCE: 41

Arg Arg Arg Gln Arg Arg Lys Lys Arg Gly Tyr
1               5                   10

<210> SEQ ID NO 42
<211> LENGTH: 8
<212> TYPE: PRT
<213> ORGANISM: Artificial sequence
<220> FEATURE:
<223> OTHER INFORMATION: Synthetic peptide

<400> SEQUENCE: 42

Arg Lys Lys Arg Arg Gln Arg Arg
1               5

<210> SEQ ID NO 43
<211> LENGTH: 11
<212> TYPE: PRT
<213> ORGANISM: Artificial sequence
<220> FEATURE:
<223> OTHER INFORMATION: Synthetic peptide

<400> SEQUENCE: 43

Tyr Ala Arg Ala Ala Ala Arg Gln Ala Arg Ala
1               5                   10

<210> SEQ ID NO 44
<211> LENGTH: 11
<212> TYPE: PRT
<213> ORGANISM: Artificial sequence
<220> FEATURE:
<223> OTHER INFORMATION: Synthetic peptide

<400> SEQUENCE: 44

Thr His Arg Leu Pro Arg Arg Arg Arg Arg Arg
1               5                   10

<210> SEQ ID NO 45
<211> LENGTH: 11
<212> TYPE: PRT
<213> ORGANISM: Artificial sequence
<220> FEATURE:
<223> OTHER INFORMATION: Synthetic peptide

<400> SEQUENCE: 45

Gly Gly Arg Arg Ala Arg Arg Arg Arg Arg Arg
1               5                   10

<210> SEQ ID NO 46
<211> LENGTH: 5
<212> TYPE: PRT
<213> ORGANISM: Artificial sequence
<220> FEATURE:

```
<223> OTHER INFORMATION: Synthetic peptide

<400> SEQUENCE: 46

Gly Ser Gly Gly Ser
1               5

<210> SEQ ID NO 47
<211> LENGTH: 4
<212> TYPE: PRT
<213> ORGANISM: Artificial sequence
<220> FEATURE:
<223> OTHER INFORMATION: Synthetic peptide

<400> SEQUENCE: 47

Gly Gly Gly Ser
1

<210> SEQ ID NO 48
<211> LENGTH: 4
<212> TYPE: PRT
<213> ORGANISM: Artificial sequence
<220> FEATURE:
<223> OTHER INFORMATION: Synthetic peptide

<400> SEQUENCE: 48

Gly Gly Ser Gly
1

<210> SEQ ID NO 49
<211> LENGTH: 5
<212> TYPE: PRT
<213> ORGANISM: Artificial sequence
<220> FEATURE:
<223> OTHER INFORMATION: Synthetic peptide

<400> SEQUENCE: 49

Gly Gly Ser Gly Gly
1               5

<210> SEQ ID NO 50
<211> LENGTH: 5
<212> TYPE: PRT
<213> ORGANISM: Artificial sequence
<220> FEATURE:
<223> OTHER INFORMATION: Synthetic peptide

<400> SEQUENCE: 50

Gly Ser Gly Ser Gly
1               5

<210> SEQ ID NO 51
<211> LENGTH: 5
<212> TYPE: PRT
<213> ORGANISM: Artificial sequence
<220> FEATURE:
<223> OTHER INFORMATION: Synthetic peptide

<400> SEQUENCE: 51

Gly Ser Gly Gly Gly
1               5

<210> SEQ ID NO 52
<211> LENGTH: 5
<212> TYPE: PRT
<213> ORGANISM: Artificial sequence
<220> FEATURE:
<223> OTHER INFORMATION: Synthetic peptide
```

```
<400> SEQUENCE: 52

Gly Gly Gly Ser Gly
1               5

<210> SEQ ID NO 53
<211> LENGTH: 5
<212> TYPE: PRT
<213> ORGANISM: Artificial sequence
<220> FEATURE:
<223> OTHER INFORMATION: Synthetic peptide

<400> SEQUENCE: 53

Gly Ser Ser Ser Gly
1               5

<210> SEQ ID NO 54
<211> LENGTH: 755
<212> TYPE: PRT
<213> ORGANISM: Rattus norvegicus

<400> SEQUENCE: 54

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Gly
            20                  25                  30

Thr Gln Ser Ser Gly Lys Ser Val Leu Glu Ser Leu Val Gly Arg
        35                  40                  45

Asp Leu Leu Pro Arg Gly Thr Gly Val Val Thr Arg Arg Pro Leu Ile
    50                  55                  60

Leu Gln Leu Val His Val Ser Pro Glu Asp Lys Arg Lys Thr Thr Gly
65                  70                  75                  80

Glu Glu Asn Asp Pro Ala Thr Trp Lys Asn Ser Arg His Leu Ser Lys
                85                  90                  95

Gly Val Glu Ala Glu Trp Gly Lys Phe Leu His Thr Lys Asn Lys
            100                 105                 110

Leu Tyr Thr Asp Phe Asp Glu Ile Arg Gln Glu Ile Glu Asn Glu Thr
        115                 120                 125

Glu Arg Ile Ser Gly Asn Asn Lys Gly Val Ser Pro Glu Pro Ile His
    130                 135                 140

Leu Lys Val Phe Ser Pro Asn Val Val Asn Leu Thr Leu Val Asp Leu
145                 150                 155                 160

Pro Gly Met Thr Lys Val Pro Val Gly Asp Gln Pro Lys Asp Ile Glu
                165                 170                 175

Leu Gln Ile Arg Glu Leu Ile Leu Arg Phe Ile Ser Asn Pro Asn Ser
            180                 185                 190

Ile Ile Leu Ala Val Thr Ala Ala Asn Thr Asp Met Ala Thr Ser Glu
        195                 200                 205

Ala Leu Lys Ile Ser Arg Glu Val Asp Pro Asp Gly Arg Arg Thr Leu
    210                 215                 220

Ala Val Ile Thr Lys Leu Asp Leu Met Asp Ala Gly Thr Asp Ala Met
225                 230                 235                 240

Asp Val Leu Met Gly Arg Val Ile Pro Val Lys Leu Gly Ile Ile Gly
                245                 250                 255

Val Val Asn Arg Ser Gln Leu Asp Ile Asn Asn Lys Lys Ser Val Thr
            260                 265                 270

Asp Ser Ile Arg Asp Glu Tyr Ala Phe Leu Gln Lys Lys Tyr Pro Ser
```

```
            275                 280                 285
Leu Ala Asn Arg Asn Gly Thr Lys Tyr Leu Ala Arg Thr Leu Asn Arg
290                 295                 300

Leu Leu Met His His Ile Arg Asp Cys Leu Pro Glu Leu Lys Thr Arg
305                 310                 315                 320

Ile Asn Val Leu Ala Ala Gln Tyr Gln Ser Leu Leu Asn Ser Tyr Gly
                325                 330                 335

Glu Pro Val Asp Asp Lys Ser Ala Thr Leu Leu Gln Leu Ile Thr Lys
                340                 345                 350

Phe Ala Thr Glu Tyr Cys Asn Thr Ile Glu Gly Thr Ala Lys Tyr Ile
                355                 360                 365

Glu Thr Ser Glu Leu Cys Gly Gly Ala Arg Ile Cys Tyr Ile Phe His
370                 375                 380

Glu Thr Phe Gly Arg Thr Leu Glu Ser Val Asp Pro Leu Gly Gly Leu
385                 390                 395                 400

Asn Thr Ile Asp Ile Leu Thr Ala Ile Arg Asn Ala Thr Gly Pro Arg
                405                 410                 415

Pro Ala Leu Phe Val Pro Glu Val Ser Phe Glu Leu Leu Val Lys Arg
                420                 425                 430

Gln Ile Lys Arg Leu Glu Glu Pro Ser Leu Arg Cys Val Glu Leu Val
                435                 440                 445

His Glu Glu Met Gln Arg Ile Ile Gln His Cys Ser Asn Tyr Ser Thr
450                 455                 460

Gln Glu Leu Leu Arg Phe Pro Lys Leu His Asp Ala Ile Val Glu Val
465                 470                 475                 480

Val Thr Cys Leu Leu Arg Lys Arg Leu Pro Val Thr Asn Glu Met Val
                485                 490                 495

His Asn Leu Val Ala Ile Glu Leu Ala Tyr Ile Asn Thr Lys His Pro
                500                 505                 510

Asp Phe Ala Asp Ala Cys Gly Leu Met Asn Asn Asn Ile Glu Glu Gln
                515                 520                 525

Arg Arg Asn Arg Leu Ala Arg Glu Leu Pro Ser Ala Val Ser Arg Asp
530                 535                 540

Lys Ser Ser Lys Val Pro Ser Ala Leu Ala Pro Ala Ser Gln Glu Pro
545                 550                 555                 560

Ser Pro Ala Ala Ser Ala Glu Ala Asp Gly Lys Leu Ile Gln Asp Asn
                565                 570                 575

Arg Arg Glu Thr Lys Asn Val Ala Ser Ala Gly Gly Ile Gly Asp
                580                 585                 590

Gly Gly Arg Ile Gly Asp Gly Gly Gln Glu Pro Thr Thr Gly Asn Trp
                595                 600                 605

Arg Gly Met Leu Lys Thr Ser Lys Ala Glu Glu Leu Ala Glu Glu
                610                 615                 620

Lys Ser Lys Pro Ile Pro Ile Met Pro Ala Ser Pro Gln Lys Gly His
625                 630                 635                 640

Ala Val Asn Leu Leu Asp Val Pro Val Pro Val Ala Arg Lys Leu Ser
                645                 650                 655

Ala Arg Glu Gln Arg Asp Cys Glu Val Ile Glu Arg Leu Ile Lys Ser
                660                 665                 670

Tyr Phe Leu Ile Val Arg Lys Asn Ile Gln Asp Ser Val Pro Lys Ala
                675                 680                 685

Val Met His Phe Leu Val Asn His Val Lys Asp Thr Leu Gln Ser Glu
                690                 695                 700
```

```
Leu Val Gly Gln Leu Tyr Lys Ser Ser Leu Asp Leu Leu Thr
705                 710                 715                 720

Glu Ser Glu Asp Met Ala Gln Arg Arg Lys Glu Ala Ala Asp Met Leu
                725                 730                 735

Lys Ala Leu Gln Gly Ala Ser Gln Ile Ile Ala Glu Ile Arg Glu Thr
                740                 745                 750

His Leu Trp
        755

<210> SEQ ID NO 55
<211> LENGTH: 742
<212> TYPE: PRT
<213> ORGANISM: Mus musculus

<400> SEQUENCE: 55

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Val Gly
            20                  25                  30

Thr Gln Ser Ser Gly Lys Ser Ser Val Leu Glu Ser Leu Val Gly Arg
        35                  40                  45

Asp Leu Leu Pro Arg Gly Thr Gly Val Val Thr Arg Arg Pro Leu Ile
    50                  55                  60

Leu Gln Leu Val His Val Ser Pro Glu Asp Lys Arg Lys Thr Thr Gly
65                  70                  75                  80

Glu Glu Asn Gly Lys Phe Gln Ser Trp Arg Val Glu Ala Glu Glu Trp
                85                  90                  95

Gly Lys Phe Leu His Thr Lys Asn Lys Leu Tyr Thr Asp Phe Asp Glu
            100                 105                 110

Ile Arg Gln Glu Ile Glu Asn Glu Thr Glu Arg Ile Ser Gly Asn Asn
        115                 120                 125

Lys Gly Val Ser Pro Glu Pro Ile His Leu Lys Val Phe Ser Pro Asn
    130                 135                 140

Val Val Asn Leu Thr Leu Val Asp Leu Pro Gly Met Thr Lys Val Pro
145                 150                 155                 160

Val Gly Asp Gln Pro Lys Asp Ile Glu Leu Gln Ile Arg Glu Leu Ile
                165                 170                 175

Leu Arg Phe Ile Ser Asn Pro Asn Ser Ile Ile Leu Ala Val Thr Ala
            180                 185                 190

Ala Asn Thr Asp Met Ala Thr Ser Glu Ala Leu Lys Ile Ser Arg Glu
        195                 200                 205

Val Asp Pro Asp Gly Arg Arg Thr Leu Ala Val Ile Thr Lys Leu Asp
    210                 215                 220

Leu Met Asp Ala Gly Thr Asp Ala Met Asp Val Leu Met Gly Arg Val
225                 230                 235                 240

Ile Pro Val Lys Leu Gly Ile Ile Gly Val Val Asn Arg Ser Gln Leu
                245                 250                 255

Asp Ile Asn Asn Lys Lys Ser Val Thr Asp Ser Ile Arg Asp Glu Tyr
            260                 265                 270

Ala Phe Leu Gln Lys Lys Tyr Pro Ser Leu Ala Asn Arg Asn Gly Thr
        275                 280                 285

Lys Tyr Leu Ala Arg Thr Leu Asn Arg Leu Leu Met His His Ile Arg
    290                 295                 300

Asp Cys Leu Pro Glu Leu Lys Thr Arg Ile Asn Val Leu Ala Ala Gln
```

```
                305                 310                 315                 320
        Tyr Gln Ser Leu Leu Asn Ser Tyr Gly Glu Pro Val Asp Asp Lys Ser
                        325                 330                 335

Ala Thr Leu Leu Gln Leu Ile Thr Lys Phe Ala Thr Glu Tyr Cys Asn
                        340                 345                 350

Thr Ile Glu Gly Thr Ala Lys Tyr Ile Glu Thr Ser Glu Leu Cys Gly
                        355                 360                 365

Gly Ala Arg Ile Cys Tyr Ile Phe His Glu Thr Phe Gly Arg Thr Leu
                        370                 375                 380

Glu Ser Val Asp Pro Leu Gly Gly Leu Asn Thr Ile Asp Ile Leu Thr
        385                 390                 395                 400

Ala Ile Arg Asn Ala Thr Gly Pro Arg Pro Ala Leu Phe Val Pro Glu
                        405                 410                 415

Val Ser Phe Glu Leu Leu Val Lys Arg Gln Ile Lys Arg Leu Glu Glu
                        420                 425                 430

Pro Ser Leu Arg Cys Val Glu Leu Val His Glu Glu Met Gln Arg Ile
                        435                 440                 445

Ile Gln His Cys Ser Asn Tyr Ser Thr Gln Glu Leu Leu Arg Phe Pro
                        450                 455                 460

Lys Leu His Asp Ala Ile Val Glu Val Val Thr Cys Leu Leu Arg Lys
        465                 470                 475                 480

Arg Leu Pro Val Thr Asn Glu Met Val His Asn Leu Val Ala Ile Glu
                        485                 490                 495

Leu Ala Tyr Ile Asn Thr Lys His Pro Asp Phe Ala Asp Ala Cys Gly
                        500                 505                 510

Leu Met Asn Asn Asn Ile Glu Glu Gln Arg Arg Asn Arg Leu Ala Arg
                        515                 520                 525

Glu Leu Pro Ser Ala Gly Ser Arg Asp Lys Ser Ser Lys Val Pro Ser
                        530                 535                 540

Ala Leu Ala Pro Ala Ser Gln Glu Pro Pro Ala Ala Ser Ala Glu
        545                 550                 555                 560

Ala Asp Gly Lys Leu Ile Gln Asp Asn Arg Arg Glu Thr Lys Asn Val
                        565                 570                 575

Pro Ser Ala Gly Gly Ile Gly Asp Gly Gly Gln Glu Pro Thr Thr
                        580                 585                 590

Gly Asn Trp Arg Gly Met Leu Lys Thr Ser Lys Ala Glu Glu Leu Leu
                        595                 600                 605

Ala Glu Glu Lys Ser Lys Pro Ile Pro Ile Met Pro Ala Ser Pro Gln
        610                 615                 620

Lys Gly His Ala Val Asn Leu Leu Asp Val Pro Val Pro Val Ala Arg
        625                 630                 635                 640

Lys Leu Ser Ala Arg Glu Gln Arg Asp Cys Glu Val Ile Glu Arg Leu
                        645                 650                 655

Ile Lys Ser Tyr Phe Leu Ile Val Arg Lys Asn Ile Gln Asp Ser Val
                        660                 665                 670

Pro Lys Ala Val Met His Phe Leu Val Asn His Val Lys Asp Thr Leu
                        675                 680                 685

Gln Ser Glu Leu Val Gly Gln Leu Tyr Lys Ser Ser Leu Leu Asp Asp
                        690                 695                 700

Leu Leu Thr Glu Ser Glu Asp Met Ala Gln Arg Arg Lys Glu Ala Ala
        705                 710                 715                 720

Asp Met Leu Lys Ala Leu Gln Gly Ala Ser Gln Ile Ile Ala Glu Ile
                        725                 730                 735
```

Arg Glu Thr His Leu Trp
            740

<210> SEQ ID NO 56
<211> LENGTH: 852
<212> TYPE: PRT
<213> ORGANISM: Gallus gallus

<400> SEQUENCE: 56

Met Gly Asn Arg Gly Met Glu Asp Leu Ile Pro Leu Val Asn Arg Leu
1               5                   10                  15

Gln Asp Ala Phe Ala Ala Ile Gly Gln Asn Ala Asn Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Asp Phe Leu Pro Arg Gly Ser Gly Ile Val
    50                  55                  60

Thr Arg Arg Pro Leu Val Leu Gln Leu Val Asn Ala Ser Thr Glu Tyr
65                  70                  75                  80

Gly Glu Phe Leu His Cys Lys Gly Lys Lys Phe Thr Asp Phe Glu Glu
                85                  90                  95

Ile Arg Leu Glu Ile Glu Ala Glu Thr Asp Arg Val Thr Gly Ser Asn
            100                 105                 110

Lys Gly Ile Ser Pro Val Pro Ile Asn Leu Arg Val Tyr Ser Pro His
        115                 120                 125

Val Leu Asn Leu Thr Leu Val Asp Leu Pro Gly Met Thr Lys Val Pro
    130                 135                 140

Val Gly Asp Gln Pro Pro Asp Ile Glu Phe Gln Ile Arg Asp Met Leu
145                 150                 155                 160

Met Gln Phe Val Thr Lys Glu Asn Cys Leu Ile Leu Ala Val Ser Pro
                165                 170                 175

Ala Asn Ser Asp Leu Ala Asn Ser Asp Ala Leu Lys Val Ala Lys Glu
            180                 185                 190

Val Asp Pro Gln Gly Gln Arg Thr Ile Gly Val Ile Thr Lys Leu Asp
        195                 200                 205

Leu Met Asp Glu Gly Thr Asp Ala Arg Asp Val Leu Glu Asn Lys Leu
    210                 215                 220

Leu Pro Leu Arg Arg Gly Tyr Ile Gly Val Val Asn Arg Ser Gln Lys
225                 230                 235                 240

Asp Ile Asp Gly Lys Lys Asp Ile Gln Ala Ala Leu Ala Ala Glu Arg
                245                 250                 255

Lys Phe Phe Leu Ser His Pro Ala Tyr Arg His Met Ala Asp Arg Met
            260                 265                 270

Gly Thr Pro Tyr Leu Gln Lys Val Leu Asn Gln Gln Leu Thr Asn His
        275                 280                 285

Ile Arg Asp Thr Leu Pro Gly Leu Arg Asn Lys Leu Gln Ser Gln Leu
    290                 295                 300

Leu Ser Ile Glu Lys Glu Val Glu Glu Tyr Lys Asn Phe Arg Pro Asp
305                 310                 315                 320

Asp Pro Ala Arg Lys Thr Lys Ala Leu Leu Gln Met Val Gln Gln Phe
                325                 330                 335

Ala Val Asp Phe Glu Lys Arg Ile Glu Gly Ser Gly Asp Gln Ile Asp
            340                 345                 350

Thr Tyr Glu Leu Ser Gly Gly Ala Arg Ile Asn Arg Ile Phe His Glu

```
              355                 360                 365
Arg Phe Pro Phe Glu Leu Val Lys Met Glu Phe Asp Glu Lys Glu Leu
370                     375                 380
Arg Arg Glu Ile Ser Tyr Ala Ile Lys Asn Ile His Gly Ile Arg Thr
385                 390                 395                 400
Gly Leu Phe Thr Pro Asp Met Ala Phe Glu Thr Ile Val Lys Lys Gln
                405                 410                 415
Val Lys Lys Ile Lys Glu Pro Cys Leu Lys Cys Val Asp Met Val Ile
                420                 425                 430
Ser Glu Leu Ile Asn Thr Val Arg Gln Cys Thr Lys Lys Leu Ser Gln
                435                 440                 445
Tyr Pro His Leu Arg Glu Glu Met Glu Arg Ile Val Thr Thr His Ile
                450                 455                 460
Arg Glu Arg Glu Gly Arg Thr Lys Asp Gln Val Met Leu Leu Ile Asp
465                 470                 475                 480
Ile Glu Leu Ala Tyr Met Asn Thr Asn His Glu Asp Phe Ile Gly Phe
                485                 490                 495
Ala Asn Ala Gln Gln Arg Ser Ser Gln Met Ser Lys Lys Ala Ala
                500                 505                 510
Gly Asn Gln Asp Glu Ile Leu Val Ile Arg Lys Gly Trp Leu Thr Ile
                515                 520                 525
Asn Asn Ile Gly Ile Met Lys Gly Gly Ser Lys Glu Tyr Trp Phe Val
530                 535                 540
Leu Thr Ala Glu Asn Leu Ser Trp Tyr Lys Asp Asp Glu Glu Lys Glu
545                 550                 555                 560
Lys Lys Tyr Met Leu Pro Val Asp Asn Leu Lys Leu Arg Asp Val Glu
                565                 570                 575
Lys Gly Phe Met Ser Ser Lys His Ile Phe Ala Leu Phe Asn Thr Glu
                580                 585                 590
Gln Arg Asn Val Tyr Lys Asp Tyr Arg Gln Leu Glu Leu Ala Cys Glu
                595                 600                 605
Thr Gln Glu Glu Val Asp Ser Trp Lys Ala Ser Phe Leu Arg Ala Gly
                610                 615                 620
Val Tyr Pro Glu Arg Val Gly Asp Lys Asp Lys Ala Ser Glu Ala Glu
625                 630                 635                 640
Glu Asn Gly Ser Asp Ser Phe Met His Ser Met Asp Pro Gln Leu Glu
                645                 650                 655
Arg Gln Val Glu Thr Ile Arg Asn Leu Val Asp Ser Tyr Met Ala Ile
                660                 665                 670
Val Asn Lys Thr Ile Arg Asp Leu Met Pro Lys Thr Ile Met His Leu
                675                 680                 685
Met Ile Asn Asn Thr Lys Asp Phe Ile His Ser Glu Leu Leu Ala Asn
                690                 695                 700
Leu Tyr Ser Cys Gly Asp Gln Asn Thr Leu Met Glu Glu Ser Ala Glu
705                 710                 715                 720
Gln Ala Gln Arg Arg Asp Glu Met Leu Arg Met Tyr His Ala Leu Lys
                725                 730                 735
Glu Ala Leu Asn Ile Ile Gly Asp Ile Asn Thr Ser Thr Ile Ser Thr
                740                 745                 750
Pro Met Pro Pro Pro Val Asp Asp Ser Trp Leu Gln Val Gln Ser Val
                755                 760                 765
Pro Ser Gly Arg Arg Ser Pro Thr Ser Ser Pro Thr Pro Gln Arg Arg
                770                 775                 780
```

```
Ala Pro Ala Val Pro Pro Ala Arg Pro Gly Ser Arg Gly Pro Ala Pro
785                 790                 795                 800

Gly Pro Pro Pro Ala Gly Gly Ser Ala Leu Gly Gly Ala Pro Pro Val
            805                 810                 815

Pro Ser Arg Pro Gly Ala Ser Pro Asp Pro Phe Gly Pro Pro Pro Gln
            820                 825                 830

Val Pro Ser Arg Pro Asn Arg Ala Pro Pro Gly Val Pro Arg Ile Thr
            835                 840                 845

Ile Ser Asp Pro
    850

<210> SEQ ID NO 57
<211> LENGTH: 846
<212> TYPE: PRT
<213> ORGANISM: Danio rerio

<400> SEQUENCE: 57

Met Gly Asn Arg Gly Met Glu Asp Leu Ile Pro Leu Val Asn Arg Met
1               5                   10                  15

Gln Asp Ala Phe Ser Ala Ile Gly Gln Asn Ala Asn Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Lys Asp Phe Leu Pro Arg Gly Ser Gly Ile Val
    50                  55                  60

Thr Arg Arg Pro Leu Val Leu Gln Leu Ile Asn Cys Pro Thr Glu Tyr
65                  70                  75                  80

Ala Glu Phe Leu His Cys Lys Gly Lys Lys Phe Thr Asp Phe Asp Glu
                85                  90                  95

Val Arg Gln Glu Ile Glu Ala Glu Thr Asp Arg Ile Thr Gly Gln Asn
            100                 105                 110

Lys Gly Ile Ser Pro Val Pro Ile Asn Leu Arg Val Tyr Ser Pro Asn
        115                 120                 125

Val Leu Asn Leu Thr Leu Val Asp Leu Pro Gly Met Thr Lys Val Pro
    130                 135                 140

Val Gly Asp Gln Pro Ala Asp Ile Glu Ala Gln Ile Arg Asp Met Leu
145                 150                 155                 160

Met Gln Phe Val Thr Lys Glu Asn Cys Leu Leu Ala Val Ser Pro
                165                 170                 175

Ala Asn Ser Asp Leu Ala Asn Ser Asp Ala Leu Lys Ile Ala Lys Glu
            180                 185                 190

Val Asp Pro Gln Gly Met Arg Thr Ile Gly Val Ile Thr Lys Leu Asp
        195                 200                 205

Leu Met Asp Glu Gly Thr Asp Ala Arg Glu Ile Leu Glu Asn Lys Leu
    210                 215                 220

Leu Pro Leu Arg Arg Gly Tyr Ile Gly Val Val Asn Arg Ser Gln Lys
225                 230                 235                 240

Asp Ile Asp Gly Lys Lys Asp Ile Thr Ala Ala Met Ser Ala Glu Arg
                245                 250                 255

Lys Phe Phe Leu Thr His Pro Ser Tyr Arg His Leu Ala Asp Arg Met
            260                 265                 270

Gly Thr Pro Tyr Leu Gln Lys Ala Leu Asn Gln Gln Leu Thr Asn His
        275                 280                 285

Ile Arg Asp Thr Leu Pro Gly Leu Arg Asn Lys Leu Gln Ser Gln Leu
```

-continued

```
            290                 295                 300
Leu Ser Ile Glu Lys Glu Val Glu Tyr Lys His Phe Arg Pro Asp
305                 310                 315                 320

Asp Pro Ser Arg Lys Thr Lys Ala Leu Leu Gln Met Val Gln Gln Phe
                325                 330                 335

Ala Val Asp Phe Glu Lys Cys Ile Glu Gly Ser Gly Asp Gln Val Asp
                340                 345                 350

Thr Val Glu Leu Ser Gly Gly Ala Arg Ile Asn Arg Ile Phe His Glu
                355                 360                 365

Arg Phe Pro Phe Glu Leu Val Lys Met Glu Phe Asp Glu Lys Glu Leu
                370                 375                 380

Arg Lys Glu Ile Ser Tyr Ala Ile Lys Asn Ile His Gly Ile Arg Thr
385                 390                 395                 400

Gly Leu Phe Thr Pro Asp Met Ala Phe Glu Thr Ile Val Lys Arg Gln
                405                 410                 415

Ile Ala Lys Ile Lys Glu Pro Cys Gln Lys Cys Val Asp Leu Val Ile
                420                 425                 430

Thr Glu Leu Val Asn Thr Val Arg Gln Cys Thr Lys Lys Leu Ala Gln
                435                 440                 445

Tyr Pro Met Leu Arg Glu Glu Met Glu Arg Ile Val Thr Gln His Ile
                450                 455                 460

Arg Asp Arg Glu Ser Arg Thr Lys Asn Gln Val Met Leu Leu Ile Asp
465                 470                 475                 480

Ile Glu Leu Ala Tyr Met Asn Thr Asn His Glu Asp Phe Ile Gly Phe
                485                 490                 495

Ala Asn Ala Gln Gln Arg Ser Ser Gln Met Asn Lys Lys Ala Ala
                500                 505                 510

Gly Asn Gln Asp Glu Ile Met Val Ile Arg Lys Gly Trp Leu Thr Ile
                515                 520                 525

Asn Asn Ile Gly Ile Met Lys Gly Gly Ala Lys Glu Tyr Trp Phe Val
                530                 535                 540

Met Thr Ala Glu Asn Leu Ser Trp Tyr Lys Asp Asp Glu Glu Lys Glu
545                 550                 555                 560

Lys Lys Tyr Met Leu Pro Leu Asp Asn Leu Lys Leu Arg Asp Ile Glu
                565                 570                 575

Lys Ser Phe Met Ser Ser Lys His Val Phe Ala Leu Phe Asn Thr Glu
                580                 585                 590

Gln Arg Asn Val Tyr Lys Asp Tyr Arg Gln Leu Glu Leu Ala Ser Asp
                595                 600                 605

Thr Gln Glu Glu Val Asp Ser Trp Lys Ala Ser Phe Leu Arg Ala Gly
                610                 615                 620

Val Tyr Pro Glu Arg Ile Thr Asp Lys Leu Lys Gln Ser Asp Thr Ser
625                 630                 635                 640

Asp Glu Ser Ser Ser Asp Gly Phe Met His Ser Met Asp Pro Gln Leu
                645                 650                 655

Glu Arg Gln Val Glu Thr Ile Arg Asn Leu Val Asp Ser Tyr Met Ala
                660                 665                 670

Ile Val Asn Lys Thr Val Arg Asp Leu Met Pro Lys Thr Ile Met His
                675                 680                 685

Leu Met Ile Asn Asn Thr Lys Asp Phe Ile His Ala Glu Leu Leu Ala
                690                 695                 700

Asn Leu Tyr Ser Cys Gly Asp Gln Asn Thr Leu Met Glu Glu Ser Ala
705                 710                 715                 720
```

Glu Gln Ala Gln His Arg Glu Met Leu Arg Met Tyr His Ala Leu
            725                 730                 735

Lys Glu Ala Leu Asn Ile Ile Gly Asp Ile Ser Thr Ser Thr Val Ser
                740                 745                 750

Thr Ala Met Pro Pro Val Asp Asp Ser Trp Leu Gln Val Gln Gly
            755                 760                 765

Gly Pro Ser Gly Arg Arg Ser Pro Met Ser Ser Pro Thr Pro Gln Arg
    770                 775                 780

Arg Ala Pro Pro Gly Pro Pro Arg Pro Gly Gly Arg Thr Ala Pro Gly
785                 790                 795                 800

Pro Pro Thr Ile Gly Ala Pro Pro Val Pro Ser Arg Pro Gly Ala Ser
                805                 810                 815

Pro Asp Pro Phe Gly Ala Pro Pro Gln Val Pro Ser Arg Pro Asn
            820                 825                 830

Arg Ala Pro Pro Gly Val Pro Arg Ile Ser Ile Ser Asp Gln
835                 840                 845

<210> SEQ ID NO 58
<211> LENGTH: 152
<212> TYPE: PRT
<213> ORGANISM: Homo sapiens

<400> SEQUENCE: 58

Met Glu Ala Val Leu Asn Glu Leu Val Ser Val Glu Asp Leu Leu Lys
1               5                   10                  15

Phe Glu Lys Lys Phe Gln Ser Glu Lys Ala Ala Gly Ser Val Ser Lys
                20                  25                  30

Ser Thr Gln Phe Glu Tyr Ala Trp Cys Leu Val Arg Ser Lys Tyr Asn
            35                  40                  45

Asp Asp Ile Arg Lys Gly Ile Val Leu Leu Glu Glu Leu Leu Pro Lys
        50                  55                  60

Gly Ser Lys Glu Glu Gln Arg Asp Tyr Val Phe Tyr Leu Ala Val Gly
65                  70                  75                  80

Asn Tyr Arg Leu Lys Glu Tyr Glu Lys Ala Leu Lys Tyr Val Arg Gly
                85                  90                  95

Leu Leu Gln Thr Glu Pro Gln Asn Asn Gln Ala Lys Glu Leu Glu Arg
            100                 105                 110

Leu Ile Asp Lys Ala Met Lys Lys Asp Gly Leu Val Gly Met Ala Ile
        115                 120                 125

Val Gly Gly Met Ala Leu Gly Val Ala Gly Leu Ala Gly Leu Ile Gly
    130                 135                 140

Leu Ala Val Ser Lys Ser Lys Ser
145                 150

<210> SEQ ID NO 59
<211> LENGTH: 152
<212> TYPE: PRT
<213> ORGANISM: Rattus norvegicus

<400> SEQUENCE: 59

Met Glu Ala Val Leu Asn Glu Leu Val Ser Val Glu Asp Leu Lys Asn
1               5                   10                  15

Phe Glu Arg Lys Phe Gln Ser Glu Gln Ala Ala Gly Ser Val Ser Lys
                20                  25                  30

Ser Thr Gln Phe Glu Tyr Ala Trp Cys Leu Val Arg Ser Lys Tyr Asn
            35                  40                  45

```
Asp Asp Ile Arg Arg Gly Ile Val Leu Leu Glu Glu Leu Leu Pro Lys
        50                  55                  60

Gly Ser Lys Glu Glu Gln Arg Asp Tyr Val Phe Tyr Leu Ala Val Gly
 65                  70                  75                  80

Asn Tyr Arg Leu Lys Glu Tyr Glu Lys Ala Leu Lys Tyr Val Arg Gly
                 85                  90                  95

Leu Leu Gln Thr Glu Pro Gln Asn Asn Gln Ala Lys Glu Leu Glu Arg
            100                 105                 110

Leu Ile Asp Lys Ala Met Lys Lys Asp Gly Leu Val Gly Met Ala Ile
        115                 120                 125

Val Gly Gly Met Ala Leu Gly Val Ala Gly Leu Ala Gly Leu Ile Gly
    130                 135                 140

Leu Ala Val Ser Lys Ser Lys Ser
145                 150

<210> SEQ ID NO 60
<211> LENGTH: 152
<212> TYPE: PRT
<213> ORGANISM: Mus musculus

<400> SEQUENCE: 60

Met Glu Ala Val Leu Asn Glu Leu Val Ser Val Glu Asp Leu Lys Asn
 1               5                  10                  15

Phe Glu Arg Lys Phe Gln Ser Glu Gln Ala Ala Gly Ser Val Ser Lys
                20                  25                  30

Ser Thr Gln Phe Glu Tyr Ala Trp Cys Leu Val Arg Ser Lys Tyr Asn
            35                  40                  45

Glu Asp Ile Arg Arg Gly Ile Val Leu Leu Glu Glu Leu Leu Pro Lys
 50                  55                  60

Gly Ser Lys Glu Glu Gln Arg Asp Tyr Val Phe Tyr Leu Ala Val Gly
 65                  70                  75                  80

Asn Tyr Arg Leu Lys Glu Tyr Glu Lys Ala Leu Lys Tyr Val Arg Gly
                 85                  90                  95

Leu Leu Gln Thr Glu Pro Gln Asn Asn Gln Ala Lys Glu Leu Glu Arg
            100                 105                 110

Leu Ile Asp Lys Ala Met Lys Lys Asp Gly Leu Val Gly Met Ala Ile
        115                 120                 125

Val Gly Gly Met Ala Leu Gly Val Ala Gly Leu Ala Gly Leu Ile Gly
    130                 135                 140

Leu Ala Val Ser Lys Ser Lys Ser
145                 150

<210> SEQ ID NO 61
<211> LENGTH: 155
<212> TYPE: PRT
<213> ORGANISM: Artificial sequence
<220> FEATURE:
<223> OTHER INFORMATION: Synthetic peptide

<400> SEQUENCE: 61

Met Glu Ala Val Val Ser Asp Ile Val Ala Pro Glu Asp Leu Lys Lys
 1               5                  10                  15

Phe Glu Lys Lys Tyr Asn Ala Glu Leu Val Lys Gly Pro Val Ser Arg
                20                  25                  30

Asp Thr Thr Phe Glu Tyr Ala Trp Cys Leu Ile Arg Ser Lys Tyr Thr
            35                  40                  45
```

-continued

```
Asn Asp Ile Val Lys Gly Ile Gln Leu Leu Glu Glu Leu Val His Thr
    50              55                  60
Ser Lys Lys Asp Asp Gln Arg Asp Phe Leu Phe Tyr Leu Ala Val Ala
65              70                  75                  80
Asn Tyr Arg Leu Lys Glu Tyr Glu Arg Ala Leu Lys Tyr Ile Arg Thr
                85                  90                  95
Leu Leu Lys Asn Glu Pro Asp Asn Lys Gln Ala Leu Glu Leu Glu Lys
            100                 105                 110
Leu Ile Lys Asp Ala Leu Lys Lys Asp Gly Leu Val Gly Met Ala Ile
        115                 120                 125
Val Gly Gly Ile Gly Leu Gly Val Ala Gly Leu Ala Gly Leu Ile Gly
    130                 135                 140
Leu Ala Val Ser Lys Ala His Lys Glu Arg Ser
145             150                 155

<210> SEQ ID NO 62
<211> LENGTH: 4
<212> TYPE: PRT
<213> ORGANISM: Artificial sequence
<220> FEATURE:
<223> OTHER INFORMATION: Synthetic peptide

<400> SEQUENCE: 62

Gly Gly Gly Gly
1
```

INHIBITORS OF MITOCHONDRIAL FISSION AND METHODS OF USE THEREOF

CROSS-REFERENCE TO RELATED APPLICATIONS

This application is a continuation of U.S. application Ser. No. 14/271,301, filed May 6, 2014, now U.S. Pat. No. 9,243,232, which is a continuation of U.S. application Ser. No. 13/471,221, filed May 14, 2012, now U.S. Pat. No. 8,748,393, which claims the benefit of U.S. Provisional Application No. 61/486,044, filed May 13, 2011, the contents of which are incorporated herein by reference in their entirety.

STATEMENT REGARDING FEDERALLY SPONSORED RESEARCH

This invention was made with Government support under contract HL052141 awarded by the National Institutes of Health. The Government has certain rights in the invention.

CROSS-REFERENCE TO A SEQUENCE LISTING

A Sequence Listing is being submitted electronically via EFS in the form of a text file, created Jan. 5, 2016, and named 091511-0595_SequenceListing.txt (57,000 bytes), the contents of which are incorporated herein by reference in their entirety.

BACKGROUND

Mitochondrial dysfunction plays an important role in a number of human diseases, including neurodegenerative diseases, cardiovascular disease, diabetes, and cancer. Proper mitochondrial function is maintained, in part, by balanced mitochondrial dynamics, i.e., a balance between an increase in mitochondrial number by fission and a decrease in mitochondrial number by fusion.

Mitochondria are organized in a highly dynamic tubular network that is continuously reshaped by opposing processes of fusion and fission (Chan, 2006, *Annu Rev Cell Dev Biol*, 22:79-99). This dynamic process controls not only mitochondrial morphology, but also the subcellular location and function of mitochondria. A defect in either fusion or fission limits mitochondrial motility, decreases energy production and increases oxidative stress, thereby promoting cell dysfunction and death (Jahani-Asl et al., 2010, *Biochim Biophys Acta* 1802:162-166; Scott and Youle, 2010; *Essays Biochem*, 47:85-98). The two opposing processes, fusion and fission, are controlled by evolutionarily conserved large GTPases that belong to the dynamin family of proteins. In mammalian cells, mitochondrial fusion is regulated by mitofusin-1 and -2 (MFN-1/2) and optic atrophy 1 (OPA1), whereas mitochondrial fission is controlled by dynamin-1-related protein, Drp1 (Scott and Youle, 2010; *Essays Biochem*, 47:85-98; Chan, 2006, *Cell* 125:1241-1252).

Drp1 is primarily found in the cytosol, but it translocates from the cytosol and the mitochondrial surface in response to various cellular stimuli to regulate mitochondrial morphology (Chang and Blackstone, 2010; *Ann NY Acad Sci*, 1201:34-39). At the mitochondrial surface, Drp1 is thought to wrap around the mitochondria to induce fission powered by its GTPase activity (Smirnova et al., 2001, *Mol Biol Cell* 12:2245-2256). Cell culture studies demonstrated that Drp1-induced excessive mitochondrial fission and fragmentation plays an active role in apoptosis (Frank et al., 2001, *Dev Cell*, 1:515-525; Estaquier and Arnoult, 2007, *Cell Death Differ*, 14:1086-1094), autophagic cell death (Twig et al., 2008, *EMBO J* 27:433-446; Barsoum et al., 2006, *EMBO J* 25:3900-3911) and necrosis (Wang et al., 2012, *Cell* 148: 228-243). Inhibition of Drp1 by either expression of a Drp1-dominant negative mutant or by RNA interference leads to decreased mitochondrial fragmentation. This reduction in mitochondrial fission impairment results in longer and more interconnected mitochondrial tubules, increased ATP production, and the prevention of cell death (Frank et al., 2001, *Dev Cell*, 1:515-525; Barsoum et al., 2006, *EMBO J* 25:3900-3911; Yuan et al., 2007, *Cell Death Differ*, 14:462-471).

The association of Drp1 with the mitochondrial outer membrane and its activity in mammalian cells depends on various accessory proteins. Fis1 is an integral mitochondrial outer membrane protein that recruits Drp1 to promote fission (Yoon et al., 2003, *Mol Cell Biol*, 23:5409-5420; James et al., 2003, *J Biol Chem* 278:36373-36379). In yeast, recruitment of Dnm1 (yeast Drp1) from the cytosol and assembly in punctate structures on the mitochondrial surface depends on Fis1 (Fannjiang et al., 2004, *Genes Dev* 18:2785-2797; Suzuki et al., 2005, *J Biol Chem* 280:21444-21452). In mammals, Fis1 interacts with Drp1 and apparently has a similar role in mitochondrial fission as its yeast counterpart; Fis1 overexpression promotes mitochondrial fragmentation and Fis1 depletion produces interconnected mitochondrial network (Yoon et al., 2003, *Mol Cell Biol*, 23:5409-5420; James et al., 2003, *J Biol Chem* 278:36373-36379).

Since protein-protein interaction (PPI) between Drp1 and Fis1 appear to be required for mitochondrial fission, an inhibitor of this interaction may have a therapeutic utility. A rational design protocol was used to identify short peptide inhibitors of the protein-protein interaction between Drp1 and Fis1. Among other things, a novel selective peptide inhibitor of Drp1 was identified and its use as an inhibitor of Drp1-mediated mitochondrial dysfunction in a cell culture model of Parkinson's disease (PD) was examined. Such mitochondria fission inhibitor compositions are described herein as related to a need in the art for methods of reducing aberrant mitochondrial fission.

SUMMARY

The present disclosure provides peptides that inhibit mitochondrial fission, and compositions comprising the peptides. The present disclosure provides methods of reducing abnormal mitochondrial fission in a cell as well as methods for treating diseases or disorders associated with abnormal mitochondrial fission.

In one aspect, a mitochondrial fission inhibitor peptide is provided wherein the peptide comprises or consists of about 7 to 20 amino acids. In one embodiment, the peptide comprises an amino acid sequence having at least about 80%, 85%, 90%, or 95% amino acid identity to a contiguous stretch of from about 7 to 20 amino acids of a Drp1 polypeptide or a Fis1 polypeptide.

In one embodiment, the mitochondrial fission inhibitor peptide comprises a peptide that is about 43%, 57%, 71%, or 86% identical to SEQ ID NO:12. In another embodiment, the fission inhibitor peptide comprises a peptide that is about 89%, 78%, 67%, or 56% identical to SEQ ID NO:11. In still another embodiment, the fission inhibitory peptide comprises a peptide that is about 89%, 78%, 67%, or 56% identical to SEQ ID NO:15. In one embodiment, the fission inhibitor peptide comprises SEQ ID NO:12, SEQ ID NO:11 or SEQ ID NO:15.

In one aspect, a mitochondrial fission inhibitor construct is provided, wherein the construct comprises a mitochondrial fission inhibitor peptide.

In one embodiment, the mitochondrial fission inhibitor construct further comprises a carrier moiety. In another embodiment, the carrier moiety is a carrier peptide. In still another embodiment, the carrier peptide comprises SEQ ID NO:32.

In one embodiment, the mitochondrial fission inhibitor construct is a linear peptide which comprises the carrier peptide linked to the fission inhibitor peptide by a peptide bond. In one embodiment, the fission inhibitor construct further comprises a linker, wherein the linker is positioned between the fission inhibitor peptide and the carrier peptide and the linker is linked at one end to the fission inhibitor peptide by a peptide bond and is linked at the other end to the carrier peptide by a peptide bond. In still another embodiment, the linker comprises 1, 2, 3, 4, 5, or more amino acids. In another embodiment, the linker comprises 1 to 2, 1 to 5, 2 to 5, 2 to 4, 1 to 10, 5 to 10, 3 to 6, or 2 to 10 amino acids. In still another embodiment, the linker is G, GG, GGG, or GGGG (SEQ ID NO:62).

In one embodiment, the inhibitor construct comprises, in order from amino terminus to carboxyl terminus: a) a protein transduction moiety, b) an optional linker, and c) a mitochondrial fission inhibitor peptide.

In one embodiment, the amino terminus, the carboxyl terminus or both the amino and carboxyl termini of the mitochondrial fission construct are modified. In another embodiment, the amino terminal modification is an amine group or an acetyl group. In still another embodiment, the carboxyl terminal modification is an amide group.

In one embodiment, the fission inhibitor construct comprises SEQ ID NO:18, SEQ ID NO: 19; SEQ ID NO:20, or SEQ ID NO:22.

In one embodiment, the fission inhibitor peptide, the carrier peptide, and/or the linker comprises one or more D-amino acids.

In one embodiment, the fission inhibitor construct inhibits GTPase activity of a Drp1 polypeptide. In another embodiment, the fission inhibitor construct selectively inhibits GTPase activity of a Drp1 polypeptide.

In one embodiment, the fission inhibitor construct inhibits binding of a Fis1 polypeptide to a Drp1 polypeptide. In another embodiment, the fission inhibitor construct selectively inhibits binding of a Fis1 polypeptide to a Drp1 polypeptide.

In one embodiment, the fission inhibitor construct reduces or inhibits mitochondrial fragmentation in a cell. In another embodiment, the fission inhibitor construct reduces or inhibits fragmentation in a cell which has been stressed. In still another embodiment, the stress is oxidative stress or stress induced by MPP+, CCCP or rotenone.

In one embodiment, the Drp1 polypeptide is about 80%, 85%, 90%, 95%, 98%, 99% or 100% identical to SEQ ID NO:1. In another embodiment, the Fis1 polypeptide is about 80%, 85%, 90%, 95%, 98%, 99% or 100% identical to SEQ ID NO:2.

In another aspect, a pharmaceutical composition comprising a mitochondrial fission inhibitor peptide is provided.

In one embodiment, the pharmaceutical composition comprises a carrier peptide, an optional linker, and a mitochondrial fission inhibitor peptide.

In one embodiment, the pharmaceutical composition comprises a pharmaceutically acceptable excipient.

In one aspect, a method of inhibiting or reducing abnormal mitochondrial fission in a cell is provided, wherein the method comprises contacting the cell with a composition comprising a mitochondrial fission inhibitor peptide, wherein said contacting inhibits abnormal mitochondrial fission.

In one embodiment, the method comprises mixing the composition comprising a mitochondrial fission inhibitor peptide with a cell in vitro. In another embodiment, the method comprises administering the composition to an animal, wherein the animal exhibits one or more symptoms of a disease or disorder associated with abnormal mitochondrial function. In another embodiment, the administering to an animal comprises administering an amount of the composition which is effective to reduce at least one adverse symptom of the disease. In still another embodiment, the adverse symptoms is selected from the group consisting of tremor, bradykinesia, rigidiy, and postural dysfunction.

In one aspect, a method of treating a disease or disorder associated with abnormal mitochondrial fission is provided.

In one embodiment, the method comprises administering to a subject diagnosed with the disease or disorder, or predisposed to the disease or disorder, a therapeutically effective amount of a mitochondrial fission inhibitor construct. In another embodiment, the administering is effective to reduce at least one adverse symptom of the disease.

In one embodiment, the disease or disorder is Parkinson's disease, Huntington's disease, Alzheimer's disease, ischemia, reperfusion injury, diabetes-induced neuropathy or heart disease.

In one embodiment, the administering is by a route selected from intravenous, intramuscular, subcutaneous or oral.

BRIEF DESCRIPTION OF THE DRAWINGS

FIG. 1C shows a sequence alignment of the 3 identified homology regions of Drp1 (Regions 108, 109, 110) and Fis1 (Regions 111, 112, 113).

DEFINITIONS

Figures 1A, 1B:
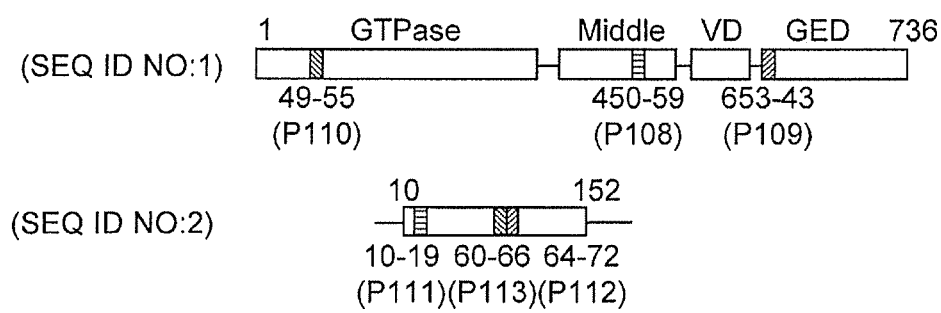
FIG. 1A provides a schematic showing regions of homology identified in the Drp1 (SEQ ID NO:1) and Fis1 (SEQ ID NO:2) proteins.
FIG. 1B shows representative sequences identified in the homologous regions of Drp1 and Fis1 (DLLPRGT, SEQ ID NO:3; STQELLRFPK, SEQ ID NO:4; KSLAREQRD, SEQ ID NO:5; ELLPKGS, SEQ ID NO:6; SVEDLLKFEK, SEQ ID NO:7; KGSKEEQRD, SEQ ID NO:8).

The terms "polypeptide," "peptide," and "protein," used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The terms "nucleic acid molecule" and "polynucleotide" are used interchangeably and refer to a polymeric form of nucleotides of any length, either deoxyribonucleotides or ribonucleotides, or analogs thereof. Non-limiting examples of polynucleotides include linear and circular nucleic acids, messenger RNA (mRNA), cDNA, recombinant polynucleotides, vectors, probes, and primers.

"Substantially pure" indicates that an entity (e.g., a synthetic peptide or a mitochondrial fission inhibitor peptide or construct) makes up greater than about 50% of the total content of the composition (e.g., total protein of the composition), or greater than about 80% of the total protein content. For example, a "substantially pure" refers to compositions in which at least 80%, at least 85%, at least 90% or more of the total composition is the entity of interest (e.g. 95%, 98%, 99%, greater than 99%), of the total protein. The protein can make up greater than about 90%, or greater than about 95% of the total protein in the composition.

The terms "subject," "individual," and "patient" are used interchangeably herein to refer to a member or members of any mammalian or non-mammalian species that may have a need for the pharmaceutical methods, compositions and treatments described herein. Subjects and patients thus include, without limitation, primate (including humans and non-human primates), canine, feline, ungulate (e.g., equine, bovine, swine (e.g., pig)), avian, and other subjects. In some cases, the subject is a murine (e.g., rat or mouse), such as a rat or mouse model of a disease. In some cases, the subject is a human.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient, in combination with another agent, or alone (e.g., in monotherapy) in one or more doses, to effect such treatment for the disease. The "therapeutically effective amount" can vary depending on the compound, the disease and its severity and the age, weight, etc., of the subject to be treated.

The terms "mitochondrial fission inhibitor peptide," "mitochondrial inhibitory peptide," "mitochondrial inhibiting peptide," or "subject synthetic peptide" are used interchageably herein to refer to the peptides described herein which function to inhibit mitochondrial fission as well as to inhibit one or more functions associated with mitochondrial fission as described herein.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a mitochondrial fission inhibitor" peptide or construct includes a plurality of such peptides or constructs and reference to "the protein translocation domain" or "the protein translocation moiety" includes reference to one or more protein translocation domains and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides synthetic peptides that inhibit mitochondrial fission, and compositions comprising the peptides. The present disclosure provides methods of reducing abnormal mitochondrial fission in a cell.

Excessive mitochondrial fragmentation through a process called fission has been implicated in the pathogenesis of diverse human diseases, including neurodegenerative diseases. Thus, selective inhibitors of aberrant mitochondrial fission will provide important research tools as well as potential leads for drug development. Disclosed herein are methods for identifying inhibitors of protein-protein interaction (PPI) between the fission protein, Drp1 (Dynamin 1-like protein, GenBank Acc. No. AAH24590; SEQ ID NO:1) or an isoform thereof (e.g., GenBank Acc. No. O00429; SEQ ID NO:9), and its mitochondrial adaptor, Fis1 (mitochondrial fission 1 protein, GenBank Acc. No. NP_057152; SEQ ID NO:2) or an isoform thereof. Also disclosed are mitochondrial fission inhibitor peptides identified through these methods.

Mitochondrial Fission Inhibitory Compositions

Previous studies have shown that short peptides derived from interaction sites between two proteins act as highly specific inhibitors of that interaction and are effective drugs in basic research and in animal models of human diseases, such as myocardial infarction and hypertension (Inagaki et al., 2003, *Circulation* 108:2304-2307; Qi et al., 2008, *J Clin Invest*, 118:173-182; Palaniyandi et al., 2009, *Cardiovasc Res* 82:229-239). One possibility is that because such peptides are flexible and represent part of the natural binding site, they may be superior and more selective inhibitors of protein-protein interaction as compared with more rigid small molecules (Rob and Mochly-Rosen, 1995, *Proc Natl Acad Sci USA* 92:492-496; Qvit and Mochly-Rosen, 2010, *Drug Discov Today Dis Mech* 7:e87-e93; Souroujon and Mochly-Rosen, 1998, *Nat Biotechnol* 16:919-924). For example, a peptide corresponding to a homologous sequence between protein kinase C (PKC) and its scaffold protein, RACK, serves as a selective regulator of the function of PKC, as determined in culture and in in vivo animal models of acute myocardial infarction (Chen et al., 2001, *Proc Natl Acad Sci USA* 98:11114-11119; Kheifets et al., 2006, *J Biol Chem* 281:23218-23226; Dorn et al., 1999, *Proc Natl Acad Sci USA*, 96:12798-128803), heart failure (Inagaki et al., 2008, *Hypertension* 51:1565-1569), pain (Sweitzer et al., 2004, *Pain* 110:281-289), and cancer (Kim et al., 2011, *Prostate* 71:946-954).

Using this rational approach, novel and selective peptide inhibitors of excessive mitochondrial fission can be designed and validated. Such fission inhibitor peptides selectively inhibit the GTPase activation of the mitochondrial fission protein, Drp1.

L-ALIGN sequence alignment software (Huang, 1991, *Advances in Applied Mathematics* 12:337-357) used to align Drp1 and Fis1 identified 3 different regions of sequence similarity between the two proteins (FIG. 1A). The amino acid sequence for each of the 3 regions within each of the Drp1 and Fis1 proteins are presented in FIG. 1B. Based on empirical structure data and molecular modeling, it was determined that each region is present on the surface of Drp1 or Fis1, and thus likely accessible for protein-protein interaction between the two proteins. Further, using principles similar to the evolutionary trace method of Lichtarge and collaborators (Lichtarge et al., 1996, *J Mol Biol* 257:342-358), it was found that while these homologous sequences are conserved in a variety of species, only the sequence in region 110 is identical in mammals, fish, chicken and yeast, suggesting that this region is most likely critical for the function of Drp1 (FIG. 1C). Another way to determine whether region 110 in Drp1 may represent a unique site for protein-protein interaction is to determine whether it is present in other proteins in the human genome. Sixteen other proteins have a sequence that is at least 80% similar to the sequence in region 110. Such region-110-like sequences were found in TOM22 (mitochondrial import receptor subunit, TOM22), DYN1 (dynamin-1), DYN2 (dynamin-2), DYN3 (dynamin-3), MIA3 (melanoma inhibitory activity protein 3), SCN5A (sodium channel protein type 5, subunit alpha), HIP1 (Huntingtin-interacting protein 1), PCDGK (protocadherin gamma-C3), BI2L2 (brain-specific angiogenesis inhibitor 1-associated protein 2-like protein 2), ZSWIM5 (zinc finger, SWIM-type containing 5), ADAM 17 (disintegrin and metalloproteinase domain-containing protein 17), AP2B (AP-2 complex subunit beta), ZSWM4 (zinc finger SWIM domain-containing protein 4), MIA2 (melanoma inhibitory activity protein 3), CYP2W1 (cytochrome P450, 2W1) and MSLN (mesothelin). However, Fis1 was the only protein in which this sequence was 100% identical in other mammalians (and 50% identical in yeast), further supporting the hypothesis that 110 represents an important region for interaction between Drp1 and Fis1.

A mitochondrial fission inhibitor construct or peptide inhibits mitochondrial fission in a cell under pathological conditions, but does not inhibit mitochondrial fission in normal control cells. Thus, a mitochondrial fission inhibitor construct or peptide of the present disclosure is useful for inhibiting aberrant (pathological) mitochondrial fission.

A mitochondrial fission inhibitor peptide can have a length of from about 7 amino acids to about 50 amino acids, e.g., from about 7 amino acids to about 10 amino acids, from about 10 amino acids to about 15 amino acids, from about 15 amino acids to about 20 amino acids, from about 20 amino acids to about 25 amino acids, from about 25 amino acids to about 30 amino acids, from about 30 amino acids to about 35 amino acids, from about 35 amino acids to about 40 amino acids, from about 40 amino acids to about 45 amino acids, or from about 45 amino acids to about 50 amino acids, or longer than 50 amino acids.

A mitochondrial fission inhibiting peptide can have a length of from about 7 amino acids to about 20 amino acids, e.g., a mitochondrial fission inhibiting peptide can have a length of 7 amino acids (aa), 8 aa, 9 aa, 10 aa, 11 aa, 12 aa, 13 aa, 14 aa, 15 aa, 16 aa, 17 aa, 18 aa, 19 aa, or 20 aa.

In some cases, a mitochondrial fission inhibitor construct comprises, in order from $NH_2$ (amino) terminus to COOH (carboxyl) terminus: a) a carrier peptide; b) an optional linker of from about 1 amino acid to about 40 amino acids; and c) a mitochondrial fission inhibitor peptide.

In some cases, a mitochondrial fission inhibitor peptide comprises an amino acid sequence having at least about 80%, at least about 85%, at least about 90%, at least about 95%, at least about 98%, at least about 99%, or 100%, amino acid sequence identity to a contiguous stretch of from about 7 amino acids to about 20 amino acids of the Fis1 amino acid sequence (SEQ ID NO:2). A mitochondrial fission inhibitor peptide can comprise an amino acid sequence differing in amino acid sequence by one, two, three, four, or five amino acids, compared to a contiguous stretch of from about 7 amino acids to about 20 amino acids of the Fis1 amino acid sequence (SEQ ID NO:2). The amino acid differences can be conservative amino acid differences.

In some cases, a mitochondrial fission inhibitor peptide comprises an amino acid sequence having at least about 80%, at least about 85%, at least about 90%, at least about 95%, at least about 98%, at least about 99%, or 100%, amino acid sequence identity to a contiguous stretch of from about 7 amino acids to about 20 amino acids of the Drp1 amino acid sequence (SEQ ID NO:1). A mitochondrial fission inhibitor peptide can comprise an amino acid sequence differing in amino acid sequence by one, two, three, four, or five amino acids, compared to a contiguous stretch of from about 7 amino acids to about 20 amino acids of the Drp1 amino acid sequence (SEQ ID NO:1). The amino acid differences can be conservative amino acid differences.

By "conservative amino acid substitution" generally refers to substitution of amino acid residues within the following groups:
  1) L, I, M, V, F;
  2) R, K;
  3) F, Y, H, W, R;
  4) G, A, T, S;
  5) Q, N; and
  6) D, E.

Conservative amino acid substitutions in the context of a mitochondrial fission inhibitor peptide are selected so as to preserve activity of the peptide. Such presentation may be preserved by substituting with an amino acid with a side chain of similar acidity, basicity, charge, polarity, or size to the side chain of the amino acid being replaced. Guidance for substitutions, insertion, or deletion may be based on alignments of amino acid sequences of different variant proteins or proteins from different species. For example, at certain residue positions that are fully conserved, substitution, deletion or insertion may not be allowed while at other positions where one or more residues are not conserved, an amino acid change can be tolerated. Residues that are semi-conserved may tolerate changes that preserve charge, polarity, and/or size. For example, a mitochondrial fission inhibitor peptide comprising SEQ ID NO:12 may have 1, 2 or 3 amino acid substitutions, at position 1, 2, 3, 4, 5, 6, and/or 7, wherein the substituted amino acid may be any one of the known 20 amino acids, wherein the inhibitor peptide maintains a mitochondrial fission inhibiting function.

A Fis1 polypeptide can have at least about 80%, at least about 85%, at least about 90%, at least about 95%, at least about 98%, at least about 99%, or 100%, amino acid sequence identity to a contiguous stretch of from about 100 amino acids to about 120 amino acids, from about 120 amino acids to about 130 amino acids, from about 130 amino acids to about 140 amino acids, or from about 140 amino acids to 152 amino acids, of the amino acid sequence depicted by SEQ ID NO:1.

A Drp1 polypeptide can have at least about 80%, at least about 85%, at least about 90%, at least about 95%, at least about 98%, at least about 99%, or 100%, amino acid sequence identity to a contiguous stretch of from about 500 amino acids to about 600 amino acids, or from about 600 amino acids to about 650 amino acids, from about 650 amino acids to about 675 amino acids, or from about 675 amino acids to 710 amino acids, of the amino acid sequence depicted by SEQ ID NO:2.

Protein Transduction Moiety

As noted above, a mitochondrial fission inhibitor construct can include, in addition to a mitochondrial fission inhibitor peptide, a carrier moiety (also referred to herein as a "protein transduction moiety"). "Carrier moiety" refers to a polypeptide, polynucleotide, carbohydrate, or organic or inorganic compound that facilitates traversing a lipid bilayer, micelle, cell membrane, organelle membrane, or vesicle membrane. A carrier moiety attached to another molecule facilitates the molecule traversing a membrane, for example going from extracellular space to intracellular space, or cytosol to within an organelle. In some cases, a carrier moiety facilitates crossing the blood-brain barrier. In some embodiments, a carrier moiety is covalently linked to the amino terminus of a mitochondrial fission inhibiting peptide. In some embodiments, a carrier moiety is covalently linked to the carboxyl terminus of a mitochondrial fission inhibiting peptide.

In some cases, the carrier moiety is a carrier peptide and is covalently linked to a fission inhibiting peptide. In some embodiments, the covalent linkage is a peptide bond. For example, the carrier peptide can be a polypeptide having a length of from about 5 amino acids (aa) to about 50 aa, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

Exemplary protein transduction domains which may be linked to the mitochondria fission inhibitor peptide include but are not limited to a minimal undecapeptide protein transduction domain corresponding to residues 47-57 of human immunodeficiency virus-1 (HIV-1) TAT (GenBank Acc. No. AEB53027; including YGRKKRRQRRR (SEQ ID NO:31) or RRRQRRKKRGY (SEQ ID NO:32)), a polyarginine sequence comprising a number of arginines sufficient to direct entry into a cell (e.g., 3, 4, 5, 6, 7, 8, 9, 10, or 10-50 arginines); a VP22 domain (Zender et al. (2002) *Cancer Gene Ther.* 9(6):489-96); an *Drosophila* Antennapedia protein transduction domain (Noguchi et al. (2003) *Diabetes* 52(7):1732-1737); a truncated human calcitonin peptide (Trehin et al. (2004) *Pharm. Research* 21:1248-1256); polylysine (Wender et al. (2000) *Proc. Natl. Acad. Sci. USA* 97:13003-13008); RRQRRTSKLMKR (SEQ ID NO:33); Transportan GWTLNSAGYLLGKINLKALAALAKKIL (SEQ ID NO:34); KALAWEAKLAKALAKA-LAKHLAKALAKALKCEA (SEQ ID NO:35); and RQIKI-WFQNRRMKWKK (SEQ ID NO:36). Exemplary PTDs include but are not limited to, YGRKKRRQRRR (SEQ ID NO:37); RRRQRRKKRGY (SEQ ID NO:38); RKKRRQRRR (SEQ ID NO:39); an arginine homopolymer of from 3 arginine residues to 50 arginine residues; Exemplary PTD domain amino acid sequences include, but are not limited to, any of the following: YGRKKRRQRRR (SEQ ID NO:40); RRRQRRKKRGY (SEQ ID NO:41); RKKRRQRR (SEQ ID NO:42); YARAAARQARA (SEQ ID NO:43); THRLPRRRRRR (SEQ ID NO:44); and GGR-RARRRRRR (SEQ ID NO:45).

Linkers

Where a mitochondrial fission inhibitor construct includes a linker which joins or links a carrier moiety to a mitochondrial fission inhibitor peptide, the linker may be a peptide having any of a variety of amino acid sequences. A linker which is a spacer peptide, can be of a flexible nature, although other chemical linkages are not excluded. A linker peptide can have a length of from about 1 amino acid to about 40 amino acids, e.g., from about 1 amino acid (aa) to about 5 aa, from about 5 aa to about 10 aa, from about 10 aa to about 20 aa, from about 20 aa to about 30 aa, or from about 30 aa to about 40, in length. These linkers can be produced using synthetic, linker-encoding oligonucleotides to couple the proteins. Peptide linkers with a degree of flexibility can be used. The linking peptides may have virtually any amino acid sequence, where in some embodiments the linker peptide will have a sequence that results in a generally flexible peptide. The use of small amino acids, such as glycine and alanine, are of use in creating a flexible peptide. The creation of such sequences is routine to those of skill in the art. Various linkers are commercially available and are considered suitable for use.

Suitable linkers can be readily selected and can be of any of a suitable of different lengths, such as from 1 amino acid (e.g., Gly) to 40 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linker which can be used to join or link a carrier moiety to a mitochondrial fission inhibitor peptide, for example, via peptide bonds, include glycine polymers $(G)_n$, (e.g., where n is an integer from 1 to about 20); glycine-serine polymers (including, for example, $(GS)_n$, $GSGGS_n$ (SEQ ID NO:46) and $GGGS_n$ (SEQ ID NO:47), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are used in some embodiments. See Scheraga, *Rev. Computational Chem.* 11173-142 (1992). Exemplary flexible linkers include, but are not limited to GG, GGG, GGS, GGSG (SEQ ID NO:48), GGSGG (SEQ ID NO:49), GSGSG (SEQ ID NO:50), GSGGG (SEQ ID NO:51), GGGSG (SEQ ID NO:52), GSSSG (SEQ ID NO:53), and the like.

Non-peptide linker moieties can also be used to join or link a carrier moiety to a mitochondrial fission inhibitor peptide. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

In an alternative embodiment, the inhibitor peptide may be linked to the carrier peptide by a disulfide bond. In some embodiments, the disulfide bond is formed between two cysteines, two cysteine analogs or a cysteine and a cysteine analog. In this embodiment, both the modulatory peptide and the carrier peptide contain at least one cysteine or cysteine analog. The cysteine residue or analog may be present as the N-terminal or C-terminal residue of the peptide or as an internal residue of the inhibitor peptide and of the carrier peptide. The disulfide linkage is then formed between the sulfur residues on each of the cysteine residues or analogs. Thus, the disulfide linkage may form between, for example, the N-terminus of the inhibitor peptide and the N-terminus of the carrier peptide, the C-terminus of the inhibitor peptide and the C-terminus of the carrier peptide, the N-terminus of the inhibitor peptide and the C-terminus of the carrier peptide, the C-terminus of the inhibitor peptide and the N-terminus of the carrier peptide, or any other such combination including at any internal position within the inhibitor peptide and/or the carrier peptide.

Exemplary Peptides

Non-limiting examples of mitochondrial fission inhibitor peptides include, e.g.,:

```
                                    (SEQ ID NO: 10)
STQELLRFPK;

(SEQ ID NO: 11)
KLSAREQRD;

(SEQ ID NO: 12)
DLLPRGS;

(SEQ ID NO: 13)
DLLPRGT;

(SEQ ID NO: 14)
CSVEDLLKFEK;

(SEQ ID NO: 15)
KGSKEEQRD;
and (SEQ ID NO: 16)
ELLPKGS.
```

Each of these inhibitor peptides can be included in a mitochondrial fission inhibitor construct. A mitochondrial fission inhibiting peptide can comprise an amino acid sequence having at least about 80%, at least about 85%, at least about 90%, at least about 95%, at least about 98%, at least about 99%, amino acid sequence identity to any of the above-listed amino acid sequences. A mitochondrial fission inhibiting peptide can comprise an amino acid sequence differing in amino acid sequence by one, two, three, four, or five amino acids, compared to any of the above-listed amino acid sequences.

Non-limiting examples of a mitochondrial fission inhibitor construct include the following:

```
                                    (SEQ ID NO: 17)
RRRQRRKKRGYGGSTQELLRFPK;

(SEQ ID NO: 18)
RRRQRRKKRGYGGKLSAREQRD;

(SEQ ID NO: 19)
RRRQRRKKRGYGGDLLPRGS;

(SEQ ID NO: 20)
RRRQRRKKRGYGGDLLPRGT;

(SEQ ID NO: 21)
RRRQRRKKRGYGGCSVEDLLKFEK;

(SEQ ID NO: 22)
RRRQRRKKRGYGGKGSKEEQRD;
and (SEQ ID NO: 23)
RRRQRRKKRGYGGELLPKGS.
```

A mitochondrial fission inhibitor peptide can comprise an amino acid sequence having at least about 80%, at least about 85%, at least about 90%, at least about 95%, at least about 98%, at least about 99%, amino acid sequence identity to any of the above-listed amino acid sequences. A mitochondrial fission inhibitor peptide can comprise an amino acid sequence differing in amino acid sequence by one, two, three, four, or five amino acids, compared to any of the above-listed amino acid sequences.

Modifications

In some cases, a subject peptide comprises one or more modifications. For example, a mitochondrial fission inhibitor construct or peptide can be cyclized. As another example, a subject peptide can have one or more amino acid modifications. A subject mitochondrial fission inhibitor construct or peptide can include one or more D-amino acids.

Modifications of interest that do not alter primary sequence include chemical derivatization of polypeptides, e.g., acetylation, or carboxylation. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are peptides that have phosphorylated amino acid residues, e.g. phosphotyrosine, phosphoserine, or phosphothreonine.

Also provided in the subject disclosure are mitochondrial fission inhibitor constructs or peptides that have been modified using ordinary molecular biological techniques and synthetic chemistry so as to improve their resistance to proteolytic degradation or to optimize solubility properties or to render them more suitable as a therapeutic agent. Analogs of such peptides include those containing residues other than naturally occurring L-amino acids, e.g., D-amino acids or non-naturally occurring synthetic amino acids.

A subject mitochondrial fission inhibitor construct or peptide may be joined to a wide variety of other oligopeptides or proteins for a variety of purposes. By providing for expression of the subject peptides, various post-translational modifications may be achieved. For example, by employing the appropriate coding sequences, one may provide farnesylation or prenylation. For example, a mitochondrial fission inhibitor construct or peptide can be bound to a lipid group at a terminus, so as to be able to be bound to a lipid membrane, such as a liposome.

Other suitable modifications include, but are not limited to (1) end-cappings of the terminal of the peptides, such as amidation of the C-terminus and/or acetylation or deamination of the N-terminus; (2) introducing peptidomimetic elements in the structure; and (3) cyclization, in which the cyclization of the peptide can occur through natural amino acids or non-naturally-occurring building blocks.

A subject mitochondrial fission inhibitor construct or peptide can be a peptoid (N-substituted oligoglycines), e.g., in which an amino acid side chain is connected to the nitrogen of the peptide backbone, instead of the α-carbon. See, e.g., Zuckermann et al. (1992) *J. Am. Chem. Soc.* 114:10646.

A subject mitochondrial fission inhibitor construct or peptide can include naturally-occurring and non-naturally occurring amino acids. A subject mitochondrial fission inhibitor construct or peptide can comprise D-amino acids, a combination of D- and L-amino acids, and various "designer" amino acids (e.g., β-methyl amino acids, Cα-methyl amino acids, and Nα-methyl amino acids, etc.) to convey special properties to peptides.

Additionally, a subject mitochondrial fission inhibitor construct or peptide can be a cyclic peptide. A subject mitochondrial fission inhibitor construct or peptide can include non-classical amino acids in order to introduce particular conformational motifs. Any known non-classical amino acid can be used. Non-classical amino acids include, but are not limited to, 1,2,3,4-tetrahydroisoquinoline-3-carboxylate; (2S,3S)-methylphenylalanine, (2S,3R)-methyl-phenylalanine, (2R,3S)-methyl-phenylalanine and (2R,3R)-methyl-phenylalanine; 2-aminotetrahydronaphthalene-2-carboxylic acid; hydroxy-1,2,3,4-tetrahydroisoquinoline-3-carboxylate; β-carboline (D and L); HIC (histidine isoquinoline carboxylic acid); and HIC (histidine cyclic urea). Amino acid analogs and peptidomimetics can be incorporated into a subject mitochondrial fission inhibitor construct or peptide to induce or favor specific secondary structures, including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analog; amide bond isostere; tretrazol; and the like.

A subject mitochondrial fission inhibitor construct or peptide can be a depsipeptide, e.g., a linear or a cyclic depsipeptide. Kuisle et al. (1999) *Tet. Letters* 40:1203-1206. "Depsipeptides" are compounds containing a sequence of at least two alpha-amino acids and at least one alpha-hydroxy carboxylic acid, which are bound through at least one normal peptide link and ester links, derived from the hydroxy carboxylic acids, where "linear depsipeptides" may comprise rings formed through S—S bridges, or through an hydroxy or a mercapto group of an hydroxy-, or mercapto-amino acid and the carboxyl group of another amino- or hydroxy-acid but do not comprise rings formed only through peptide or ester links derived from hydroxy carboxylic acids. "Cyclic depsipeptides" are peptides containing at least one ring formed only through peptide or ester links, derived from hydroxy carboxylic acids.

A subject mitochondrial fission inhibitor construct or peptide can be cyclic or bicyclic. For example, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexyl-carbodiimide (DCC) in solution, for example, in methylene chloride (CH$_2$Cl$_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Methods for making cyclic peptides are well known in the art. See, e.g., U.S. Patent Publication No. 2011/0092384.

The term "bicyclic" refers to a peptide comprising two ring closures. The ring closures are formed by covalent linkages between amino acids in the peptide. A covalent linkage between two nonadjacent amino acids constitutes a ring closure, as does a second covalent linkage between a pair of adjacent amino acids which are already linked by a covalent peptide linkage. The covalent linkages forming the ring closures may be amide linkages, i.e., the linkage formed between a free amino on one amino acid and a free carboxyl of a second amino acid, or linkages formed between the side chains or "R" groups of amino acids in the peptides. Thus, bicyclic peptides may be "true" bicyclic peptides, i.e., peptides cyclized by the formation of a peptide bond between the N-terminus and the C-terminus of the peptide, or they may be "depsi-bicyclic" peptides, i.e., peptides in which the terminal amino acids are covalently linked through their side chain moieties.

A desamino or descarboxy residue can be incorporated at a terminus or terminii of the peptide, so that there is no terminal amino or carboxyl group, to decrease susceptibility to proteases or to restrict the conformation of the peptide. C-terminal functional groups include amide, amide lower alkyl, amide di(lower alkyl), lower alkoxy, hydroxy, and carboxy, and the lower ester derivatives thereof, and the pharmaceutically acceptable salts thereof.

In some embodiments, a subject mitochondrial fission inhibitor construct or peptide comprises one or more non-naturally occurring amino acids (e.g., non-encoded amino acids). In some embodiments, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids.

Inclusion of a non-naturally occurring amino acid can provide for linkage to a polymer, a second polypeptide, a scaffold, etc. For example, a subject mitochondrial fission inhibitor construct or peptide linked to a water-soluble polymer can be made by reacting a water-soluble polymer (e.g., poly(ethylene glycol) (PEG)) that comprises a carbonyl group to an the subject mitochondrial fission inhibitor construct or peptide that comprises a non-naturally encoded amino acid that comprises an aminooxy, hydrazine, hydrazide or semicarbazide group.

As another example, a subject mitochondrial fission inhibitor construct or peptide linked to a water-soluble polymer can be made by reacting a subject mitochondrial fission inhibitor construct or peptide that comprises an alkyne-containing amino acid with a water-soluble polymer (e.g., PEG) that comprises an azide moiety; in some embodiments, the azide or alkyne group is linked to the PEG molecule through an amide linkage. A "non-naturally encoded amino acid" refers to an amino acid that is not one of the 20 common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

In some embodiments, a subject mitochondrial fission inhibitor construct or peptide is linked (e.g., covalently linked) to a polymer (e.g., a polymer other than a polypeptide). Suitable polymers include, e.g., biocompatible polymers, and water-soluble biocompatible polymers. Suitable polymers include synthetic polymers and naturally-occurring polymers. Suitable polymers include, e.g., substituted or unsubstituted straight or branched chain polyalkylene, polyalkenylene or polyoxyalkylene polymers or branched or unbranched polysaccharides, e.g. a homo- or hetero-polysaccharide. Suitable polymers include, e.g., ethylene vinyl alcohol copolymer (commonly known by the generic name EVOH or by the trade name EVAL); polybutylmethacrylate; poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); copoly(ether-esters) (e.g., poly(ethylene oxide)-poly(lactic acid) (PEO/PLA) co-polymers); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; amorphous Teflon; poly(ethylene glycol); and carboxymethyl cellulose.

Suitable synthetic polymers include unsubstituted and substituted straight or branched chain poly(ethyleneglycol), poly(propyleneglycol) poly(vinylalcohol), and derivatives thereof, e.g., substituted poly(ethyleneglycol) such as methoxypoly(ethyleneglycol), and derivatives thereof. Suitable naturally-occurring polymers include, e.g., albumin, amylose, dextran, glycogen, and derivatives thereof.

Suitable polymers can have an average molecular weight in a range of from 500 Da to 50,000 Da, e.g., from 5000 Da to 40,000 Da, or from 25,000 to 40,000 Da. For example, in some embodiments, where a subject mitochondrial fission inhibitor construct or peptide comprises a poly(ethylene glycol) (PEG) or methoxypoly(ethyleneglycol) polymer, the PEG or methoxypoly(ethyleneglycol) polymer can have a molecular weight in a range of from about 0.5 kiloDaltons (kDa) to 1 kDa, from about 1 kDa to 5 kDa, from 5 kDa to 10 kDa, from 10 kDa to 25 kDa, from 25 kDa to 40 kDa, or from 40 kDa to 60 kDa.

Compositions as Modulators of Mitochondrial Fission and Associated Activities and Effects on Cells Mitochondrial fission inhibitor peptides identified by the rational design approach described above, are characterized and validated through various functional assays described in more detail below. These functional assays are useful both in identifying inhibitors and activators of mitochondrial fission and of abnormal cell activities, as well as in characterizing the effects of the mitochondrial fission inhibitor constructs and compositions on mitochondrial activities and on the cells housing the mitochondria.

A mitochondrial fission peptide, or construct comprising the peptide, will have one or more of the following activities: 1) inhibition of Drp1 GTPase activity; 2) inhibition of binding of Drp1 to Fis1; 3) reduction of mitochondrial damage in a cell under pathological conditions or other conditions of stress; 4) reduction of cell death in a cell under pathological conditions or other conditions of stress; 5) reduction of translocation of Drp1 from the cytosol to a mitochondrion; 6) and inhibition of mitochondrial fragmentation in a cell under pathological conditions. Other effects include, but are not limited to, reduced mitochondrial fragmentation in neuronal cells exposed to several mitochondrial toxins; reduced mitochondrial ROS ($O_2$—) production and subsequently improved mitochondrial membrane potential and mitochondrial integrity; increased cell viability through reduction in apoptosis and autophagic cell death; and reduced loss of neurites in primary dopaminergic neurons in a Parkinsonism cell culture model through reduction in mitochondrial fragmentation and mitochondrial ROS production. In a preferred embodiment, treatment with or exposure to a mitochondrial fission inhibitor construct or peptide will have minimal effects on mitochondrial fission and cell viability of cells which are in non-stressed conditions or in a non-disease state.

In some embodiments, the inhibitor activity is selective, with respect to effects of the peptide or construct on a particular protein. In other words, a peptide or construct having selective inhibitory activity will inhibit the GTPase activity of Drp1 but inhibit the GTPase activity of other proteins such as, but not limited to, MFN1 or OPA1. In other embodiments, the inhibitor activity is selective in reducing mitochondrial damage, reducing cell death, reducing translocation of Drp1 from the cytosol to a mitochondrion, or inhibiting mitochondrial fragmentation when used to treat a diseased or stressed cell as compared to when the same inhibitor peptide or construct is used to treat a healthy or non-stressed cell. For the purposes of the present disclosure, a diseased cell includes a healthy cell which has been treated or genetically engineered to model a diseased cell.

To measure an increase or decrease of an activity or function upon treatment by a composition described herein, it is understood by the person having ordinary skill in the art that the function or activity can be measured, for example, in the presence and in the absence of the composition (e.g., mitochondrial fission inhibitor protein or construct), and a comparison is made between the levels of the activities in the presence and absence of the composition. Alternatively, the function or activity can be measured, for example, in the presence of two separate compositions, and the levels of the activity or function in the presence of each composition are compared. An inhibition of an activity can be a reduction of about 5% to 10%, 5% to 20%, 2% to 20%, 10% to 20%, 5% to 25%, 20% to 50%, 40% to 60%, 50% to 75%, 60% to 80%, 75% to 95%, 80% to 100%, 50% to 100%, 90% to 100%, or 85% to 95% when comparing the two conditions. Similarly, activation of an activity can be a increase of about 5% to 10%, 5% to 20%, 2% to 20%, 10% to 20%, 5% to 25%, 20% to 50%, 40% to 60%, 50% to 75%, 60% to 80%, 75% to 95%, 80% to 100%, 50% to 100%, 90% to 100%, 85% to 95%, or more than 100% but less than 500%, when comparing the two conditions.

Methods of Making a Inhibitor Construct or Peptide

A mitochondrial fission inhibitor peptide or construct can be isolated and purified in accordance with conventional methods of recombinant synthesis. A lysate may be prepared of the expression host and the lysate purified using high performance liquid chromatography (HPLC), exclusion chromatography, gel electrophoresis, affinity chromatography, or other purification technique. For the most part, the compositions which are used will comprise at least 80% by weight of the desired product, at least about 85% by weight, at least about 95% by weight, or at least about 99.5% by weight, in relation to contaminants related to the method of preparation of the product and its purification. The percentages can be based upon total protein.

A mitochondrial fission inhibitor peptide or construct may be prepared by in vitro (e.g., cell-free) synthesis, using conventional methods as known in the art. Various commercial synthetic apparatuses are available, for example, automated synthesizers by Applied Biosystems, Inc., Foster City, Calif., Beckman, etc. By using synthesizers, naturally occurring amino acids may be substituted with unnatural amino acids. The particular sequence and the manner of preparation will be determined by convenience, economics, purity required, and the like.

If desired, various groups may be introduced into the peptide during synthesis or during expression, which allow for linking to other molecules or to a surface, or provide some other desired property such as increased solubility, increased resistance to proteolysis, increased in vivo half-life, and the like. One or more cysteines can be used to make thioethers, histidines for linking to a metal ion complex, carboxyl groups for forming amides or esters, amino groups for forming amides, and the like.

A mitochondrial fission inhibitor peptide or construct as described herein may be in the form of a pharmaceutically acceptable salt. Pharmaceutically acceptable salts include acid addition salts, such as hydrochloride, hydrobromide, sulfurate, nitrate, phosphorate, acetate, propionate, glycolate, pyruvate, oxalate, malate, malonate, succinate, maleate, fumarate, tartarate, citrate, benzoate, cinnamate, mandelate, methanesulfonate, ethanesulfonate, p-toluene-sulfonate, salicylate and the like, and base addition salts, such as sodium, potassium, calcium, magnesium, lithium, aluminum, zinc, ammonium, ethylenediamine, arginine, piperazine and the like.

Compositions

The present disclosure provides compositions comprising a mitochondrial fission inhibitor peptide or construct. The composition can comprise, in addition to a mitochondrial fission inhibitor peptide or construct, one or more of: a salt, e.g., NaCl, $MgCl_2$, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.; a solubilizing agent; a detergent, e.g., a non-ionic detergent such as TWEEN-20, etc.; a protease inhibitor; glycerol; and the like.

Compositions comprising a mitochondrial fission inhibitor construct or peptide may include a buffer, which is selected according to the desired use of the peptide, and may also include other substances appropriate to the intended use. Those skilled in the art can readily select an appropriate buffer, a wide variety of which are known in the art, suitable for an intended use.

In some cases, a mitochondrial fission inhibitor construct or peptide composition is a pharmaceutical composition. A subject pharmaceutical composition can be administered to a subject in need thereof (e.g., a subject in need of inhibition of abnormal (e.g., pathological) mitochondrial fission). A subject pharmaceutical composition comprises: a) a mitochondrial fission inhibitor construct or peptide; and b) a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", $19^{th}$ Ed. (1995), or latest edition, Mack Publishing Co; A. Gennaro (2000) "Remington: The Science and Practice of Pharmacy", 20th edition, Lippincott, Williams, & Wilkins; Pharmaceutical Dosage Forms and Drug Delivery Systems (1999) H. C. Ansel et al., eds $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

Nucleic Acids Encoding the Constructs or Peptides

The present disclosure provides synthetic nucleic acids, where a subject synthetic nucleic acid comprises a nucleotide sequence encoding a mitochondrial fission inhibitor peptide or construct. A nucleotide sequence encoding a mitochondrial fission inhibitor peptide or construct can be operably linked to one or more regulatory elements, such as a promoter and enhancer, that allow expression of the nucleotide sequence in the intended target cells (e.g., a cell that is genetically modified to synthesize the encoded mitochondrial fission inhibitor construct or peptide). In some embodiments, a subject nucleic acid is a recombinant expression vector.

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, cytomegalovirus immediate early promoter; herpes simplex virus thymidine kinase promoter; early and late SV40 promoters; promoters present in long terminal repeats from a retrovirus; a metallothionein-I promoter; and the like.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; promoters such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) *Proc. Natl. Acad. Sci. U.S.A.* 80:21-25).

A nucleotide sequence encoding a mitochondrial fission inhibitor peptide or construct can be present in an expression vector and/or a cloning vector. An expression vector can include a selectable marker, an origin of replication, and other features that provide for replication and/or maintenance of the vector.

Large numbers of suitable vectors and promoters are known to those of skill in the art; many are commercially available for generating a subject recombinant construct. Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

The present disclosure provides isolated genetically modified host cells (e.g., in vitro cells) that are genetically modified with a nucleic acid comprising a nucleic acid sequence which encodes a mitochondrial fission inhibitor peptide or construct. In some embodiments, a subject isolated genetically modified host cell can produce a mitochondrial fission inhibitor construct or peptide.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Neurospora crassa, Chlamydomonas reinhardtii*, and the like.

Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. lmmunol.* 148:1176-1181; U.S. Pat. No. 6,447,784; and Sizemore et al. (1995) *Science* 270:299-302.

Formulations, Dosages, and Routes of Administration

A mitochondrial fission inhibitor peptide or construct of the present disclosure (also referred to below as "active agent") can be incorporated into a variety of formulations for therapeutic use (e.g., for treating a subjection diagnosed with or suffering from a disease which is associated with abnormal mitochondrial fission). More particularly, a mitochondrial fission inhibitor peptide or construct can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, lotions, and aerosols. As such, administration of a mitochondrial fission inhibitor peptide or construct can be achieved in various ways, including oral, vaginal, buccal, rectal, parenteral, intraperitoneal, intravenous, intramuscular, intradermal, transdermal, intratracheal, etc., administration. A mitochondrial fission inhibitor peptide or construct can be systemic after administration or may be localized by the use of an implant or other formulation that acts to retain the active dose at the site of implantation.

A mitochondrial fission inhibitor peptide or construct can be administered alone, in a combination of two or more mitochondrial fission inhibitor peptide or construct, or a mitochondrial fission inhibitor peptide or construct can be used in combination with known compounds (e.g., therapeutic agents suitable for treating a disease associated with abnormal mitochondrial fission, etc.) In pharmaceutical dosage forms, a mitochondrial fission inhibitor peptide or construct may be administered in the form of its pharmaceutically acceptable salt. The following methods and excipients are merely exemplary and are in no way limiting.

For oral preparations, a mitochondrial fission inhibitor peptide or construct can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A mitochondrial fission inhibitor peptide or construct of the present disclosure can be formulated into preparations for injections by dissolving, suspending or emulsifying the peptide in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A mitochondrial fission inhibitor peptide or construct of the present disclosure can be utilized in aerosol formulation to be administered via inhalation. A mitochondrial fission inhibitor construct or peptide of the present disclosure can be formulated into pressurized acceptable propellants such as dichlorodifluoromethane, propane, nitrogen and the like.

A mitochondrial fission inhibitor peptide or construct of the present disclosure can be used in topical formulations, by formulation with conventional additives such as solubilizers, isotonic agents, suspending agents, emulsifying agents, stabilizers and preservatives.

Furthermore, a mitochondrial fission inhibitor peptide or construct of the present disclosure can be made into suppositories by mixing with a variety of bases such as emulsifying bases or water-soluble bases. A mitochondrial fission inhibitor construct or peptide of the present disclosure can be administered rectally via a suppository. The suppository can include vehicles such as cocoa butter, carbowaxes and polyethylene glycols, which melt at body temperature, yet are solidified at room temperature.

Unit dosage forms for oral, vaginal or rectal administration such as syrups, elixirs, and suspensions may be provided wherein each dosage unit, for example, teaspoonful, tablespoonful, tablet or suppository, contains a predetermined amount of a mitochondrial fission inhibitor peptide or construct of the present disclosure. Similarly, unit dosage forms for injection or intravenous administration may comprise a mitochondrial fission inhibitor peptide or construct in a composition as a solution in sterile water, normal saline or another pharmaceutically acceptable carrier.

Implants for sustained release formulations are well known in the art. Implants can be formulated as microspheres, slabs, etc. with biodegradable or non-biodegradable polymers. For example, polymers of lactic acid and/or glycolic acid form an erodible polymer that is well-tolerated by the host. An implant containing a mitochondrial fission inhibitor peptide or construct can be used, so that the local concentration of active agent (mitochondrial fission inhibitor peptide or construct) is increased relative to the rest of the body.

Liposomes can be used as a delivery vehicle. The lipids can be any suitable combination of known liposome forming lipids, including cationic or zwitterionic lipids, such as phosphatidylcholine. The remaining lipid can include neutral or acidic lipids, such as cholesterol, phosphatidyl serine, phosphatidyl glycerol, and the like.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

The term "unit dosage form", as used herein, refers to physically discrete units suitable as unitary dosages for human and non-human animal subjects, each unit containing a predetermined quantity of a mitochondrial fission inhibitor peptide or construct calculated in an amount sufficient to produce the desired effect in association with a pharmaceutically acceptable diluent, carrier or vehicle. The specifications for the unit dosage forms depend on the particular peptide or construct employed and the effect to be achieved, and the pharmacodynamics associated with the peptide or construct in the host.

Exemplary dosages for systemic administration range from 0.1 µg to 100 milligrams per kg weight of subject per administration. An exemplary dosage may be one tablet taken from two to six times daily, or one time-release capsule or tablet taken once a day and containing a proportionally higher content of active ingredient. The time-release effect may be obtained by capsule materials that dissolve at different pH values, by capsules that release slowly by osmotic pressure, or by any other known means of controlled release.

Depending on the subject and condition being treated and on the administration route, an active agent (e.g., a mitochondrial fission inhibitor peptide or construct) may be administered in dosages of, for example, 0.1 µg to 500 mg/kg body weight per day, e.g., from about 0.1 µg/kg body weight per day to about 1 µg/kg body weight per day, from about 1 µg/kg body weight per day to about 25 µg/kg body weight per day, from about 25 µg/kg body weight per day to about 50 µg/kg body weight per day, from about 50 µg/kg body weight per day to about 100 µg/kg body weight per day, from about 100 µg/kg body weight per day to about 500 µg/kg body weight per day, from about 500 µg/kg body weight per day to about 1 mg/kg body weight per day, from about 1 mg/kg body weight per day to about 25 mg/kg body weight per day, from about 25 mg/kg body weight per day to about 50 mg/kg body weight per day, from about 50 mg/kg body weight per day to about 100 mg/kg body weight per day, from about 100 mg/kg body weight per day to about 250 mg/kg body weight per day, or from about 250 mg/kg body weight per day to about 500 mg/kg body weight per day. The range is broad, since in general the efficacy of a therapeutic effect for different mammals varies widely with doses generally being 20, 30 or even 40 times smaller (per unit body weight) in man than in the rat. Similarly the mode of administration can have an effect on dosage. Thus, for example, oral dosages may be about ten times the injection dose. Higher doses may be used for localized routes of delivery.

A specific mitochondrial fission inhibitor peptide or construct can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

Those of skill will readily appreciate that dose levels can vary as a function of the specific mitochondrial fission inhibitor peptide or construct, the severity of the symptoms and the susceptibility of the subject to side effects. Some of the specific peptides may be more potent than others. Preferred dosages for a given peptide are readily determinable by those of skill in the art by a variety of means. One means is to measure the physiological potency of a given peptide.

Routes of Administration

An active agent (e.g., a mitochondrial fission inhibitor peptide or construct) is administered to an individual using any available method and route suitable for drug delivery, including in vivo and ex vivo methods, as well as systemic and localized routes of administration. Administration can be acute (e.g., of short duration, e.g., a single administration, administration for one day to one week), or chronic (e.g., of long duration, e.g., administration for longer than one week, e.g., administration over a period of time of from about 2 weeks to about one month, from about one month to about 3 months, from about 3 months to about 6 months, or more).

Conventional and pharmaceutically acceptable routes of administration include intranasal, intramuscular, intratracheal, subcutaneous, intradermal, transdermal, sublingual, topical application, intravenous, ocular (e.g., topically to the eye, intravitreal, etc.), rectal, nasal, oral, and other enteral and parenteral routes of administration. Routes of administration may be combined, if desired, or adjusted depending upon the agent and/or the desired effect. A mitochondrial fission inhibitor peptide or construct can be administered in a single dose or in multiple doses.

An active agent (e.g., a mitochondrial fission inhibitor peptide or construct) can be administered to a host using any available conventional methods and routes suitable for delivery of conventional drugs, including systemic or localized routes. In general, routes of administration contemplated by the invention include, but are not necessarily limited to, enteral, parenteral, and inhalational routes.

Parenteral routes of administration other than inhalation administration include, but are not necessarily limited to, topical, transdermal, subcutaneous, intramuscular, intraorbital, intracapsular, intraspinal, intrasternal, ocular, and intravenous routes, i.e., any route of administration other than through the alimentary canal. Parenteral administration can be carried to effect systemic or local delivery of the agent. Where systemic delivery is desired, administration can involve invasive or systemically absorbed topical or mucosal administration of pharmaceutical preparations.

A mitochondrial fission inhibitor peptide or construct can also be delivered to the subject by enteral administration. Enteral routes of administration include, but are not necessarily limited to, oral and rectal (e.g., using a suppository) delivery.

Methods of administration of a mitochondrial fission inhibitor peptide or construct through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Treatment Methods

The present disclosure provides methods for treating a subject suffering from a disease or disorder characterized by, resulting from, or associated with, abnormal mitochondrial fission, is provided, wherein a mitochondrial fission inhibitor peptide or construct as described above is administered to the subject. Subjects amenable to treatment include individuals at risk of contracting the disease or disorder but not showing symptoms, as well as subjects presently showing symptoms. Such diseases or disorders include neurodegenerative diseases, cardiac diseases, mitochondriopathies, cancers, and the like. In some embodiments, the subject is suffering from Parkinson's disease, Huntington's disease, Alzheimer's disease, hypertension, encephalopathy, amyotrophic lateral sclerosis, cardiovascular disease, diabetes-induced neuropathy, cardiopathy, ischemia, reperfusion injury, heart failure, peripheral artery disease, and cancer.

A therapeutically effective amount of a mitochondrial fission inhibitor peptide or construct can be based on an amount of the peptide or construct which has been shown to be effective in reducing mitochondrial fission in a cell, for example, in vitro or in an animal model, compared to the degree of mitochondrial fission observed in the same system in the absence of treatment with the construct or peptide. The effective amount can be based on an amount which has been shown to be sufficient to reduce cell death (including, e.g., neuronal cell death) caused by abnormal mitochondrial fission at least about 10%, at least about 20%, at least about 30%, at least about 40%, at least about 50%, or more than 50%, compared to the degree of cell death in the absence of treatment with the construct or peptide.

A method of the present disclosure for treating disorders and diseases characterized by, resulting from, or associated with, abnormal mitochondrial fission generally involves administering to a subject in need thereof an effective amount of a mitochondrial fission inhibitor peptide or construct. A therapeutically effective amount of a mitochondrial fission inhibitor peptide or construct can be an amount sufficient to reduce an adverse symptom of the disease or disorder characterized by, resulting from, or associated with, abnormal mitochondrial fission by at least about 10%, at least about 20%, at least about 30%, at least about 40%, at least about 50%, or more than 50%, compared to the degree of the adverse symptom in the absence of treatment with the construct or peptide.

An effective amount of a mitochondrial fission inhibitor peptide or construct can be an amount sufficient to improve one or more functions in an individual having a disease or disorder characterized by, resulting from, or associated with, abnormal mitochondrial fission, compared to the level of the function in the absence of treatment with the peptide.

In some embodiments, multiple doses of an active agent are administered. The frequency of administration of a mitochondrial fission inhibitor peptide or construct ("active agent") can vary depending on any of a variety of factors, e.g., severity of the symptoms, etc. For example, in some embodiments, a mitochondrial fission inhibitor peptide or construct is administered once per month, twice per month, three times per month, every other week (qow), once per week (qw), twice per week (biw), three times per week (tiw), four times per week, five times per week, six times per week, every other day (qod), daily (qd), twice a day (bid), or three times a day (tid). As discussed above, in some embodiments, a mitochondrial fission inhibitor peptide or construct is administered continuously.

The duration of administration of a mitochondrial fission inhibitor peptide or construct, e.g., the period of time over which a mitochondrial fission inhibitor peptide or construct is administered, can vary, depending on any of a variety of factors, e.g., patient response, etc. For example, a mitochondrial fission inhibitor construct or peptide can be administered over a period of time ranging from about one day to about one week, from about two weeks to about four weeks, from about one month to about two months, or from about two months to about four months, or more.

The activity of a mitochondrial fission inhibitor peptide or construct in reducing abnormal mitochondrial fission in a cell, and treating an individual having a disease or disorder characterized by, resulting from, or associated with, abnormal mitochondrial fission, can be tested in a non-human animal model of such a disease or disorder.

In some aspects, a method for measuring the effects of a mitochondrial fission inhibitor peptide or construct when administered to an animal model is provided.

Suitable non-human animal models of Parkinson's disease (PD) include, e.g., the α-synuclein transgenic mouse model; and the 1-methyl-4-phenyl-1,2,3,6,-tetrahydropyridine (MPTP) mouse model of Parkinson's disease. See, e.g., Betarbet et al. (2002) *Bioessays* 24:308; Orth and Tabrizi (2003) *Mov. Disord.* 18:729; Beal (2001) *Nat. Rev. Neurosci.* 2:325.

Suitable non-human animal models of Huntington's disease include, e.g., a transgenic mouse comprising a human huntingtin transgene (e.g., the R6 line, the YAC line), where the human huntingtin transgene comprises 30-150 CAG repeats (encoding a polyglutamine expansion); a knock-in mouse model, comprising a homozygous or heterozygous replacement of endogenous mouse huntingtin gene with a human huntingtin gene comprising 30-150 CAG repeats. See, e.g., Mangiarini et al. (1996) *Cell* 87:493; Menalled (2005) *NeuroRx* 2:465; and Menalled and Chesselet (2002) *Trends Pharmacol. Sci.* 23:32; and Hodgson et al. (1999) *Neuron* 23:181.

For example, the effect of a mitochondrial fission inhibitor peptide on cognitive function, muscle function, motor function, brain function, behavior, and the like, is assessed. Electrophysiological tests can be used to assess brain function. Muscle function can be assessed using, e.g., a grip strength test. Motor function can be tested using, e.g., a rotarod test. Cognitive functions can be tested using, e.g., the open field test, the elevated plus maze, the Morris water maze, the zero maze test, the novel objection recognition test, and the like. Tests for neurological functioning and behavior that include sensory and motor function, autonomic reflexes, emotional responses, and rudimentary cognition, can be carried out. Such tests are well known in the art; see, e.g., Chapter 12 "Assessments of Cognitive Deficits in Mutant Mice" by Rodriguiz and Wetsel, in "Animal Models of Cognitive Impairment" (2006) E. D. Levin and J. J. Buccafusco, eds. CRC Press, Boca Raton, Fla.

The effect of a mitochondrial fission inhibitor construct or peptide on diabetes-induced neuropathy can be tested on a non-human animal model of diabetes (type 1 or type 2). See, e.g., Rees and Alcolado (2005) *Diabet. Med.* 22:359. Examples of suitable models include, e.g., the non-obese diabetic (NOD) mouse model. See, e.g., Kitukani and Makino (1992) *Adv. Immunol.* 51:285.

Subjects

Subjects suitable for treatment with a mitochondrial fission inhibitor peptide or construct include, e.g., an individual who has been diagnosed as having a disorders and diseases characterized by, resulting from, or associated with, abnormal mitochondrial fission, where such diseases include, e.g., neurodegenerative diseases, cardiac diseases, mitochondriopathies, cancers, and the like. Such diseases include, but are not limited to, Parkinson's disease, Huntington's disease, Alzheimer's disease, hypertension, encephalopathy, amyotrophic lateral sclerosis, cardiovascular disease, diabetes-induced neuropathy, cardiopathy, ischemia, reperfusion injury, heart failure, peripheral artery disease, and cancer.

Inhibition of Drp1 GTPase Activity

In one embodiment, the fission inhibitor proteins and constructs as described herein are identified by their ability to inhibit Drp1 GTPase activity. For example, the present disclosure describes how inhibitor proteins identified using the rational design approach described above are shown to be inhibitors of Drp1 GTPase activity. In another embodiment, the protein and construct is a selective inhibitor of the GTPase activity.

Figures 2A, 2B:
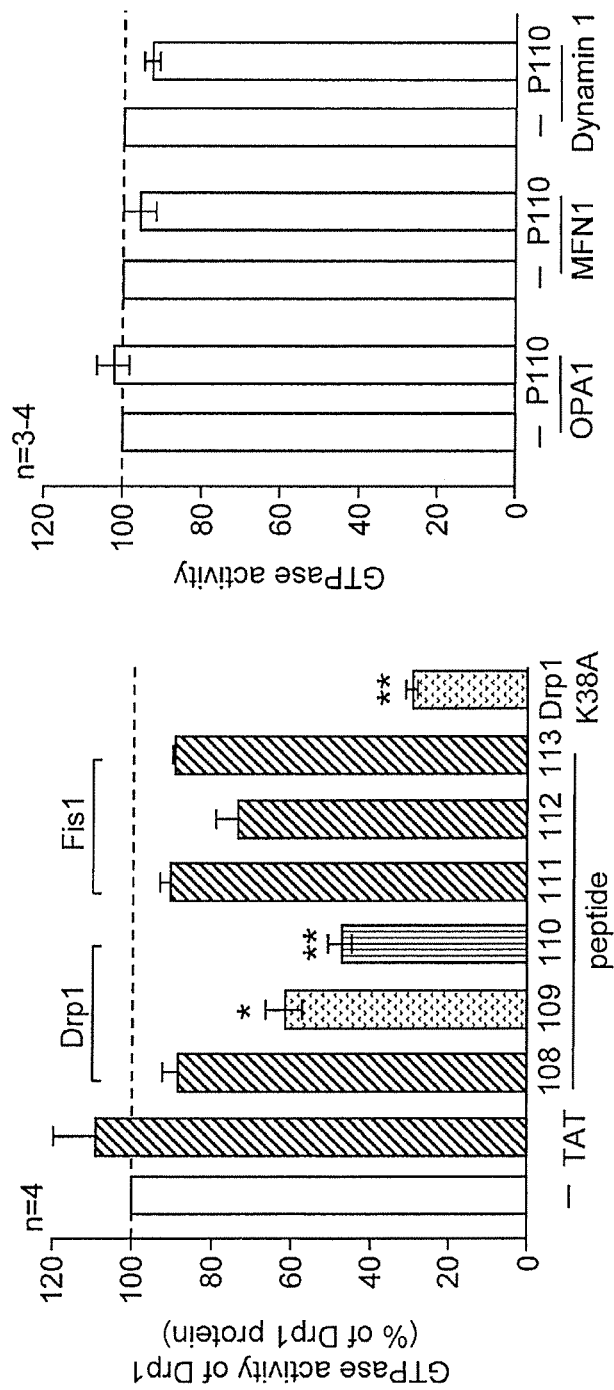
FIG. 2A is a graph showing effects of mitochondrial fission inhibitor peptides on GTPase activity of Drp1.
FIG. 2B shows the effect of a mitochondrial fission inhibitor construct on GTPase activity of various proteins.

Drp1 is a large GTPase and its mitochondrial fission activity is dependent on its GTP hydrolysis (9). As described in Example 2, two fission constructs, P109 and P110, comprising amino acid sequences derived from the Drp1 GTP exchange domain (GED) and GTPase domain, respectively (FIG. 1A), were tested for their ability to affect the enzymatic activity of Drp1. P109 and P110 inhibited 40% and 50% of the GTPase activity of recombinant Drp1, respectively (FIG. 2a). Additional experiments showed, however, that P110 had no effect on the GTPase activity of other mitochondrial dynamics-related proteins, including MFN1, OPA1, or Dynamin 1 (FIG. 2B). These data show that P110 comprises a mitochondrial fission inhibitor peptide which selectively inhibits Drp1 GTPase activity (e.g., inhibits Drp1 GTPase activity under conditions wherein P110 does not inhibit GTPase activity of a non-Drp1 protein such as MFN1, OPA1 or Dynamin 1). In some embodiments, a mitochondrial fission inhibitor construct comprises a mitochondrial fission inhibitor peptide which has a sequence which is about 42%, 57%, 71%, or 86% identical to SEQ ID NO:12 (e.g., contains 1, 2, 3, or 4 conservative amino acid substitutions such as Ser to Thr; e.g., SEQ ID NO:13), and in which the inhibitor construct or peptide selectively inhibits Drp1 GTPase activity. In other embodiments, the inhibitor construct comprises a sequence which is about 56%, 67%, 78%, or 89% identical to SEQ ID NO:13 or SEQ ID NO:16 (contains 1, 2, 3, or 4 conservative amino acid substitutions), and in which the inhibitor construct or peptide inhibits Drp1 GTPase activity.

In some embodiments, a mitochondrial fission inhibitor construct or peptide can inhibit GTPase activity of a Drp1 polypeptide by at least about 10%, at least about 15%, at least about 20%, at least about 25%, at least about 30%, at least about 35%, at least about 40%, at least about 50%, at least about 60%, at least about 70%, at least about 80%, or more than 80%, compared to the level of GTPase activity of the Drp1 polypeptide in the absence of the mitochondrial fission inhibitor construct or peptide.

A mitochondrial fission inhibitor construct or peptide may have no substantial effect on GTPase activity of a polypeptide that has GTPase activity, other than a Drp1 polypeptide. Thus, a mitochondrial fission inhibitor construct or peptide can in some cases selectively inhibit GTPase activity of a Drp1 polypeptide. For example, a mitochondrial fission inhibitor construct or peptide has no substantial effect on GTPase activity of mitofusin-1 or OPA1. Mitofusin-1 polypeptides are known in the art. See, e.g., Santel et al. (2003) *J. Cell Sci.* 116:2763; Santel and Fuller (2001) *J. Cell Sci.* 114:867; Hales and Fuller (1997) *Cell* 90:121; and GenBank Accession No. NP_284941. OPA1 polypeptides are known in the art. See, e.g., Alexander et al. (2000) *Nat. Genet.* 26:211; Dadgar et al. (2006) *Exp. Eye Res.* 83:702; and GenBank Accession No. NP_056375.

In one embodiment, a method for administering a mitochondrial inhibitor construct or peptide to a cell in vitro or to an animal is provided, wherein the effects of the construct or peptide on the cell are measured by measuring GTPase activity in the presence and in the absence of the inhibitor construct or peptide.

Inhibition of Drp1-Fis1 Interaction GTPase Activity

In one embodiment, the fission inhibitor proteins and constructs as described herein are identified by their ability to inhibit interaction between Drp1 and Fis1. Activation of mitochondrial fission by Drp1 involves the interaction of Drp1 with Fis1 which located in the outer membrane of the mitochondria. As shown in Example 2, the P110 inhibitor construct (SEQ ID NO:19) inhibited interaction of Drp1 and Fis1 on isolated mitochondria and in cultured neurons.

In some cases, a mitochondrial fission inhibitor construct or peptide can inhibit binding of a Drp1 polypeptide to an Fis1 polypeptide by at least about 10%, at least about 15%, at least about 20%, at least about 25%, at least about 30%, at least about 35%, at least about 40%, at least about 50%, at least about 60%, at least about 70%, at least about 80%, or more than 80%, compared to the degree of binding of the Drp1 polypeptide to the Fis1 polypeptide in the absence of the mitochondrial fission inhibitor construct or peptide.

In one embodiment, a method for administering a mitochondrial inhibitor construct or peptide to a cell in vitro or to an animal is provided, wherein the effects of the construct or peptide on the cell are measured by measuring interaction of Drp1 and Fis1 on isolated mitochondria or cultured neurons.

Inhibition of Mitochondrial Fission

A mitochondrial fission inhibitor peptide or construct can reduce mitochondrial fragmentation in a cell under pathological conditions (e.g., where mitochondria in the cell are undergoing pathological mitochondrial fission). For example, a mitochondrial fission inhibitor peptide or construct can reduce mitochondrial fragmentation in a cell by at least about 10%, at least about 15%, at least about 20%, at least about 25%, at least about 30%, at least about 35%, at least about 40%, at least about 50%, at least about 60%, at least about 70%, at least about 80%, or more than 80%, compared to the degree of mitochondrial fragmentation in the absence of the mitochondrial fission inhibitor construct or peptide.

In one embodiment, a method for administering a mitochondrial inhibitor construct or peptide to a cell in vitro or to an animal is provided, wherein the effects of the construct or peptide on the cell are measured by measuring the level of mitochondrial fragmentation in a cell (e.g., cultured neurons) which was treated in vitro or which was isolated from an animal which had been administered the construct or peptide.

Inhibition of Drp1 Translocation to the Mitochondria

A mitochondrial fission inhibitor peptide or construct can in some cases inhibit translocation of a Drp1 polypeptide from the cytosol to mitochondria in a cell. For example, a mitochondrial fission inhibitor peptide or construct can inhibit translocation of a Drp1 polypeptide from the cytosol to mitochondria in a cell by at least about 10%, at least about 15%, at least about 20%, at least about 25%, at least about 30%, at least about 35%, at least about 40%, at least about 50%, at least about 60%, at least about 70%, at least about 80%, or more than 80%, compared to the degree of translocation of the Drp1 polypeptide from the cytosol to mitochondria in the absence of the mitochondrial fission inhibitor peptide or construct.

In one embodiment, a method for administering a mitochondrial inhibitor construct or peptide to a cell in vitro or to an animal is provided, wherein the effects of the construct or peptide on the cell are measured by measuring the translocation of Drp1 to mitochondria in a cell (e.g., cultured neurons) which was treated in vitro or which was isolated from an animal which had been administered the construct or peptide.

Effects on Mitochondrial Morphology

The mitochondrial fission inhibitor constructs or peptides as described herein can affect mitochondrial morphology. More specifically, the constructs or peptides may function to decrease the extent of mitochondrial fragmentation as viewed using confocal microscopy with the appropriate fluorescent-labeled markers as described in the Examples below. In preferred embodiments, the inhibitor constructs or peptides described herein decrease the extent of mitochondrial fragmentation in a cell which is under a stressed condition as compared to effects of the construct or peptide in a cell which is not under a stressed condition. In some embodiments, the cell is a neuronal cell.

Effects on Production of Reactive Oxygen Species (ROS) and Membrane Potential

The fission inhibitor constructs or peptides as described herein can affect the production of reactive oxygen species (ROS) by a cell. Reactive oxygen species include, but are not limited to, hydrogen peroxide. The constructs or peptides can reduce production of mitochondrial superoxide or can reduce or inhibit cytochrome c release by the mitochondria. As noted above, such effects of the peptide or constructs are preferably observed in cells which are stressed, but the effects are not detected, or occur to a much lesser extent in cells which are not stressed. Similarly, the constructs or peptides described herein can improve or increase mitochondrial membrane potential (MMP) in stressed cells.

In one embodiment, a method for administering a mitochondrial inhibitor construct or peptide to a cell in vitro or to an animal is provided, wherein the effects of the construct or peptide on the cell or mitochondria obtained from the cell result in a decrease in the production of one or more reactive oxygen species, or result in an increase in mitochondrial membrane potential. In another embodiment, the effects are determined in stressed and/or diseased cells and the decrease in ROS or increase in MMP is relative to ROS production or MMP, respectively, in non-stressed and/or healthy cells.

Effects on Programmed Cell Death and Cell Survival

The fission inhibitor constructs or peptides as described herein can reduce the onset of programmed cell death and increase cell survival. In one embodiment, a method for administering a mitochondrial inhibitor construct or peptide to a cell in vitro or to an animal is provided, wherein the effects of the construct or peptide on the cell or mitochondria obtained from the cell result in a decrease in the onset of programmed cell death as measured by reduced accumulation of active Bax on the mitochondria, reduced or blocked release of cytochrome c from the mitochondria and increased Bcl-2 levels on the mitochondria, as compared to cells which have not been treated with or exposed to the inhibitor construct or peptide. In another embodiment, cells or animals which are exposed to or treated with the inhibitor construct or peptide exhibit a reduction in the number of cells which are Annexin V-positive as compared to cells which were not exposed to or treated with the inhibitor construct or peptide.

Effects on Neurite Degeneration in a Parkinsonism Model

The fission inhibitor constructs or peptides as described herein can reduce the neuronal degeneration in a cell culture model of Parkinsonism. In one embodiment, a method for administering a mitochondrial inhibitor construct or peptide to a cell in vitro or to an animal is provided, wherein the effects of the construct or peptide on the cell or mitochondria obtained from the cell result in reduced neurite loss of dopaminergic neurons as measured by levels of tyrosine hydroxylase (TH), as compared to cells which have not been treated with or exposed to the inhibitor construct or peptide.

Although the mitochondrial fission inhibitor constructs described herein may be peptides, such peptides may be bioavailable. For example, many of the constructs described herein are linked to a cell-permeable peptide carrier (e.g., TAT$_{47-57}$). Linking a biologically active peptide to such a carrier peptide or other transduction moiety as described herein has been widely and successfully used for cargo delivery in cultures (in vitro) and in vivo. Previous studies showed that TAT-conjugated peptides can quickly enter cells and pass through the blood-brain-barrier (43,46) and have extensive bio-distribution within minutes after single dose treatment in vivo and in cultures (47,48). Thus, P110 may be useful in treatment of diseases associated with excessive mitochondrial fission, such as Parkinsonism.

Developing strategies to limit mitochondrial damage and to ensure cellular integrity by inhibiting mitochondrial fission impairment can identify important new therapeutics. The first inhibitor of mitochondrial fission, Mdivi-1, was identified using a chemical screen in yeast cells harboring a mitochondrial fusion-defective mutant fzo1-1 (human mitofusin 1) (49). Mdivi-1 increases growth rate in yeast and inhibits mitochondrial division in yeast and mammals by blocking Dnm1 (yeast Drp1) polymerization. However, whether Mdivi-1 affects mammalian Drp1 in the same way as in yeast Dnm1 remains to be determined.

As described herein, Drp1-induced mitochondrial ROS disrupted the mitochondrial membrane potential (MMP), an important step for the induction of mitochondria-mediated cell death (Twig et al., 2008, *EMBO J* 27:433-446). These data are in agreement with the report that mitochondrial ROS is an upstream of MMP reduction, which is essential for initiation of mitochondrial fission. Indeed, it was discovered that a mitochondrial fission inhibitor construct, e.g., P110, can inhibit excessive mitochondrial fission in the presence of stressors, such as MPP+ and CCCP, resulting in decreased ROS production, preservation of mitochondrial membrane potential and inhibition of cell death. Excessive mitochondrial fission and fragmentation leads to apoptosis and autophagy in a number of human cell lines, such as human SH-SY5Y neuronal cells (Wang et al., 2011, *Aging Cell* 10:807-823). Drp1 function is required for apoptotic mitochondrial fission, as either expression of a dominant-negative mutant (Drp1K38A) or downregulation of Drp1 by RNAi delay mitochondrial fragmentation, cytochrome c release, caspase activation, and cell death (Cassidy-Stone et al., 2008, *Dev Cell* 14:193-204; Cereghetti et al., 2010, *Cell Death Differ* 17:1785-1794). Consistent with previous studies, it is shown herein that inhibition of Drp1 with a mitochondrial fission inhibitor construct, e.g., P110, prevents the accumulation of the apoptotic factor, Bax, on the mitochondria and cytochrome c release, and can recover anti-apoptotic factor Bcl-2 levels. The changes of these Bcl-2 family proteins and inhibition of the consequent cytochrome c release reflect a correction of the compromised MMP, which causes apoptosis at a later stage. Further, fission can yield asymmetric daughter mitochondria that differ in membrane potential (Rivolta et al., 2002, *Brain Res Dev Brain Res* 133:49-56), which could be later targeted by the autophagy machinery (Twig et al., 2008, EMBO 27:433-446). Indeed, overexpression of Fis1 reduces mitochondrial mass and triggers autophagy (Gomes et al., 2008, *Biochim Biophys Acta* 1777:860-866), whereas overexpression of a Drp1 dominant negative mutant reduces autophagy (Barsoum et al., 2006, *EMBO J* 25:3900-3911). Because a Drp1 peptide inhibitor, e.g., P110, greatly reduces MPP+-induced autophagy and apoptosis, it is likely that excessive activation of Drp1-mediated mitochondrial fission is involved in executing multiple cell death pathways (Reddy et al., 2011, *Brain Res Rev* 67:103-118). Importantly, inhibition of Drp1 by P110 could reduce these types of cell death at initial stage of mitochondrial damages, thus leading to neuronal cell protection.

A causal role of Drp1-dependent mitochondrial fission impairment in the pathogenesis of Parkinsonism has been recently reported (Bueler, 2009, 218:235-246). The Parkinsonism-inducing neurotoxins, 6-hydroxy dopamine, rotenone, and MPP+, all trigger Drp1 translocation to the mitochondria and mitochondrial fragmentation (fission), thus leading to dopaminergic cell death in neuronal cultures. Parkinsonism-related proteins PINK1, parkin, DJ-1 and alpha-synuclein appear to control mitochondrial function by associating with Drp1 and regulating mitochondrial fusion/fission events. It is clear that neurotoxins causing Parkinsonism and Parkinsonism-associated genes are related to mitochondrial dynamics. Thus, controlling Drp1-mediated mitochondrial fission impairment in Parkinsonism may be of particular importance to inhibit neurodegeneration. Using cell culture models of Parkinsonism, it was determined as described herein that in response to MPP+, a mitochondrial fission inhibitor construct or peptide, e.g, P110, reduces dopaminergic neuronal degeneration by inhibiting Drp1-mediated mitochondrial dysfunction. In addition, impaired mitochondrial dynamics and excessive mitochondrial fission have been connected to a number of neurological disorders, including neurodegenerative diseases (Knott et al., 2008, *Nat Rev Neurosci* 9:505-518), hypertensive encephalopathy (Qi et al., 2008, J Clin Invest 118:173-182), stroke (Liu et al., 2012, *Brain Res* 1456:94-99) and neurologic pain (Ferrari et al., 2011, *J Neurosci* 31:11404-11410). Therefore, an inhibitor of Drp1, such as P110, may be a useful treatment for the diseases in which impairment of mitochondrial dynamics occurs.

Further, using a model of Parkinson's disease (PD) in culture, it was demonstrated herein that a mitochondrial fission inhibitor construct or peptide, e.g, P110, is neuroprotective by inhibiting mitochondrial fragmentation and ROS production and subsequently improving mitochondrial membrane potential and mitochondrial integrity. A mitochondrial fission inhibitor construct or peptide, e.g, P110, can increase neuronal cell viability by reducing apoptosis and autophagic cell death, and reducing neurites loss of primary dopaminergic neurons in this PD cell culture model. Importantly, it was also discovered that treatment with a mitochondrial fission inhibitor construct or peptide, e.g, P110, had minimal effects on mitochondrial fission and cell viability under normal conditions.

Further Embodiments

Embodiment 1 is a mitochondrial fission inhibitor construct comprising a mitochondrial fission inhibitor peptide comprising about 7 to 20 amino acids, wherein the peptide comprises an amino acid sequence having at least about 80% amino acid identity to a contiguous stretch of from about 7 to 20 amino acids of a Drp1 polypeptide (SEQ ID NO:1) or a Fis1 polypeptide (SEQ ID NO:2).

Embodiment 2 is the inhibitor construct of embodiment 1, further comprising a protein transduction moiety.

Embodiment 3 is the inhibitor construct of embodiment 2, wherein the protein transduction moiety is a carrier peptide Embodiment 4 is the inhibitor construct of embodiment 2 or 3, wherein the protein transduction moiety comprises a carrier peptide derived from a human immunodeficiency virus Tat polypeptide.

Embodiment 5 is the inhibitor construct of embodiment 2, 3 or 4, wherein the protein transduction moiety comprises SEQ ID NO:32.

Embodiment 6 is the inhibitor construct of embodiment 1, wherein the construct is a linear peptide comprising:
a) the fission inhibitor peptide;
b) an optional linker; and
c) a carrier peptide.

Embodiment 7 is the inhibitor construct of embodiment 6, comprising a linker, wherein the linker is positioned between the fission inhibitor peptide and the carrier peptide.

Embodiment 8 is the inhibitor construct of any one of embodiments 1-7, wherein the fission inhibitor peptide comprises SEQ ID NO:12.

Embodiment 9 is the inhibitor construct of embodiment 6 or 7, comprising SEQ ID NO:19.

Embodiment 10 is the inhibitor construct of any one of embodiments 1-9, wherein the inhibitor construct selectively inhibits a GTPase activity of the Drp1 polypeptide.

Embodiment 11 is the inhibitor construct of any one of embodiments 1-9, wherein the inhibitor construct inhibits binding of the Drp1 polypeptide to the Fis1 polypeptide.

Embodiment 12 is the inhibitor construct of any one of embodiments 1-9, wherein the inhibitor construct reduces mitochondrial fragmentation in a cell.

Embodiment 13 is the inhibitor construct of any one of embodiments 1-9, wherein the inhibitor construct inhibits translocation of the Drp1 polypeptide from the cytosol to a mitochondrion in a cell.

Embodiment 14 is the use of the inhibitor construct of any one of embodiments 1-13 for inhibiting or reducing abnormal mitochondrial fission, comprising contacting a cell with a composition comprising a mitochondrial fission inhibitor construct, wherein the contacting reduces abnormal mitochondrial fission.

Embodiment 15 is the use according to embodiment 14, wherein the contacting a cell comprises administering the composition to an animal.

Embodiment 16 is the use according to embodiment 14 or 15, wherein administering the composition to the animal results in a decrease in tremor, bradykinesia, rigidiy, and/or postural dysfunction.

Embodiment 17 is the use of the inhibitor construct of any one of embodiments 1-13 for treating a subject suffering from, diagnosed with or predisposed to a disease or disorder associated with abnormal mitochondrial fission, comprising administering to a subject having or diagnosed with the disease or disorder a therapeutically effective amount of a pharmaceutical composition comprising a mitochondrial fission inhibitor construct, wherein the administering is effective to reduce at least one adverse symptom of the disease.

Embodiment 18 is the use according to embodiment 17, wherein the administering is by a route selected from oral, intravenous, intramuscular, and subcutaneous.

Embodiment 19 is the use according to embodiment 17 or 18, wherein the disease or disorder is Parkinson's disease, Huntington's disease, Alzheimer's disease, ischemia, reperfusion injury, diabetes-induced neuropathy, or heart disease.

Embodiment 20 is the use according to embodiment 17, 18 or 19, wherein administering the composition to the animal results in a decrease in tremor, bradykinesia, rigidiy, and/or postural dysfunction.

Ranging from tool design, target validation and bio-efficacy demonstration, the findings from the studies described herein are novel and important for understanding the role of mitochondrial impairment in neurodegeneration as well as representing a general and easy approach to identify protein-protein interaction inhibitors. Inhibitors, such as peptide inhibitor P110, open up a therapeutic avenue for treatment of neurodegenerative diseases, such as Parkinson's disease, which has no effective treatment available.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Rational Design of Modulator Peptides

An L-ALIGN sequence alignment software 31 was used, resulting in the identification of 3 different regions of similarity between Drp1 (human Drp1, GenBank Acc. No. AAH24590) and Fis 1 (human Fis1, GenBank Acc. No. NP_057152). The regions of similarity are shown as a schematic in FIG. 1A, marked as regions 108-113. Crystal structures for these proteins are known and show that these regions are present on the surface of Drp1 and Fis1, thus likely accessible for protein-protein interaction (PPI). Further, all these sequences are conserved in a variety of species (FIG. 1C). However, only the sequence in region 110 is conserved in mammals, fish, chicken and yeast, suggesting that this region is most likely critical for the function of Drp1. Further sequence alignment analysis showed that there are 17 other proteins in the human genome which contain a sequence that is at least 80% similar to the sequence in region 110. These proteins include TOM22, DYN1, DYN2, DYN3, MIA3, SCN5A, HIP1, PCDGK, B12L2, ZSWIM5, ADAM 17, AP2B, ZSWM4, CYP2W1 and MSLN. However, Fis1 was the only protein in which this sequence was 100% identical in other mammals, further supporting the idea that 110 represents an important region within Drp1 for interaction with Fis1.

Peptides corresponding to region 110, as well as to the five other sequence similarity regions which had been identified between Fis1 and Drp1 were synthesized using a standard phase peptide synthetic method. Peptides were synthesized using a microwave by Liberty Microwave Peptide Synthesizer (CEM Corporation, Matthews, N.C., USA). The C-terminus of the peptides was modified to C(O)—$NH_2$ using Rink Amide AM resin to increase stability (Gomes and Scorrano, 2008, *Biochim Biophys Acta* 1777:860-866). Peptides were analyzed by analytical reverse-phase high-pressure liquid chromatography (RP-HPLC) (Shimadzu, Md., USA) and matrix-assisted laser desorption/ionization (MALDI) mass spectrometry (MS) and purified by preparative RP-HPLC (Shimadzu, Md., USA).

Each peptide was linked via a Gly-Gly (GG) linker to the cell permeating TAT protein-derived peptide, $TAT_{47-57}$, (Chen et al., 2001, *Chem Biol* 8:1123-1129; Zhu et al., 2004, *J Biol Chem* 279:35967-35974) to produce a single linear peptide. These mitochondrial fission inhibitor constructs are referred to herein as P110, P108, P109, P111, P112 and P113:

The constructs used are as follows:

```
P108:
                                     (SEQ ID NO: 17)
RRRQRRKKRGYGGSTQELLRFPK;

P109:
                                     (SEQ ID NO: 18)
RRRQRRKKRGYGGKLSAREQRD;

P110:
                                     (SEQ ID NO: 19)
RRRQRRKKRGYGGDLLPRGS;

P110a:
                                     (SEQ ID NO: 20)
RRRQRRKKRGYGGDLLPRGT;

P111:
                                     (SEQ ID NO: 21)
RRRQRRKKRGYGGCSVEDLLKFEK;

P112:
                                     (SEQ ID NO: 22)
RRRQRRKKRGYGGKGSKEEQRD;
and P113:
                                     (SEQ ID NO: 23)
RRRQRRKKRGYGGELLPKGS.
```

Example 2

Effects on Drp1 GTPase Activity In Vitro

First, mitochondrial fission inhibitor constructs were tested to determine what, if any, effects each peptide had on enzyme (GTPase) activity. Recombinant protein Drp1, Mfn1, OPA1 or dynamin-1 (25 ng) was incubated with the indicated modulator peptides for 30 min. GTPase activity was assayed in vitro using a GTPase assay kit (Innova Biosciences, Littleton, USA, or Novus Biologicals, Littleton, Colo.) according to manufacturer's instructions.

Figure 2C:
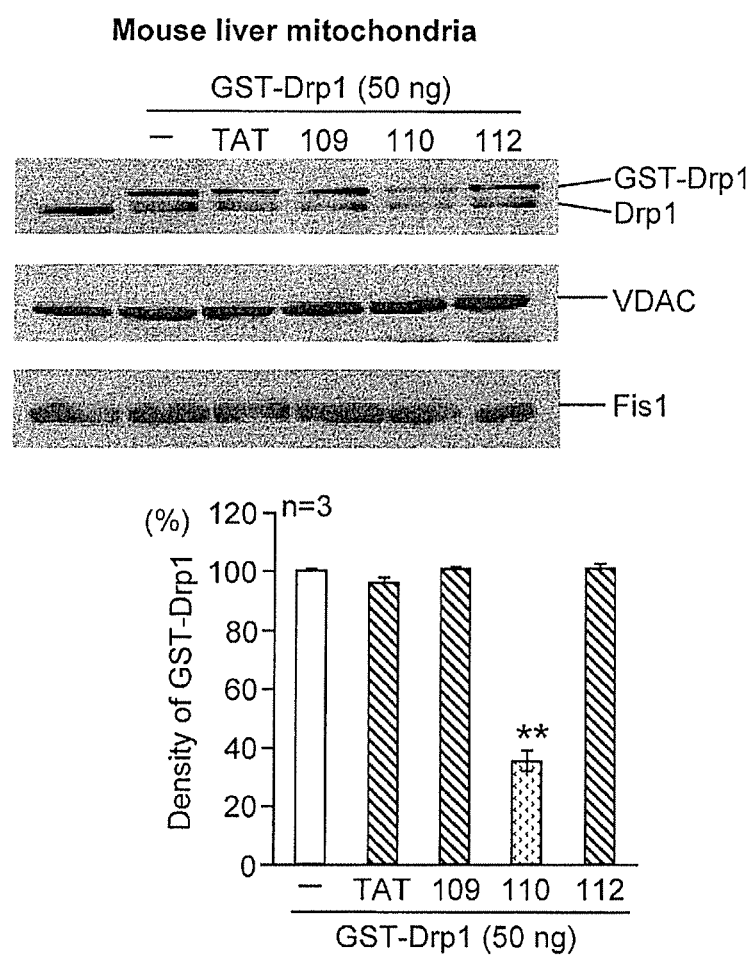
FIG. 2C shows the effects of mitochondrial fission inhibitor constructs on interaction of Drp1 with mitochondria. The top panel is a western blot; the bottom panel is a quantitative representation of the western blot.

In an in vitro GTPase assay, two of the peptide inhibitor constructs (P110 and P112) specifically inhibited Drp1 GTPase activity by 30% and 50% (n=3), respectively. These two inhibitor constructs had no effects on the GTPase activity of mitofusin1 and OPA1. In the presence of P109 and P110, a 40% and 50% of inhibition in the GTPase activity, respectively, was observed (FIG. 2A). The other peptides, including the constructs comprising the corresponding homologous peptides derived from Fis1, P112 and P113, respectively, exerted no significant effect. These data are surprising, because they indicate that these two Drp1-derived peptides interact with Drp1, thus suggesting that the sequence corresponding to P109 and P110 are also involved in intra-molecular interactions or in inter-molecular interactions between oligomers of Drp1 (Zhu et al., 2004, *J Biol Chem* 279:35967-35974). A dominant negative mutant of Drp1, Drp1 K38A, which inhibits Drp1 GTPase activity and fission activity (Frank et al., 2001, *Dev Cell* 1:515-525), was used as a positive control and reduced Drp1 activity by ~70% (FIG. 2A). Importantly, peptide P110 had no effects on the GTPase activities of other mitochondrial dynamics-related proteins, such as Mfn1 and OPA1 (FIG. 2B). P110 had also no effects on the GTPase activity of the related protein, dynamin-1 (FIG. 2B), which belongs to DRP family and mediates endocytosis of the plasma membrane (McClure and Robinson, 1996, *Mol Membr Biol* 13:189-215). These data indicate that peptide P110 is selective for Drp1. In contrast, P109 increased the GTPase activity of Mfn1 and OPA1 in the same assay (MFN1, 229%±10; OPA1, 177%±13;, p<0.05, n=3, respectively (FIG. 2F), indicating that only P110 is a selective for Drp1.

Example 3

Interaction Between Drp1 and Fis1

If the peptides designed do represent PPI surfaces between Drp1 and Fis1, the peptides should inhibit the association of Drp1 with the mitochondria. To obtain isolated mitochondria, SH-5YSH cells were washed with cold phosphate-buffered saline (PBS) and incubated on ice in lysis buffer (250 mM sucrose, 20 mmol/L HEPES-NaOH, pH 7.5, 10 mmol/L KCl, 1.5 mmol/L MgCl$_2$, 1 mmol/L EDTA, protease inhibitor cocktail, phosphatase inhibitor cocktail) for 30 minutes. Cells were scraped and then disrupted 10 times by repeated aspiration through a 25 gauge needle, followed by a 30 gauge needle. Mouse liver tissue was minced and ground by pestle in lysis buffer. The homogenates were spun at 800 g for 10 min at 4° C. and the resulting supernatants were spun at 10,000 g for 20 minutes at 4° C. The pellets were washed with lysis buffer and spun at 10,000 g again for 20 minutes at 4° C. The final pellets were suspended in lysis buffer containing 1% Triton X-100 and were mitochondrial-rich lysate fractions.

SH-SY5Y cells were treated with Drp1 peptides P110, P109, P112 or TAT$_{47-57}$ only (1 µM). Because the interaction between Drp1 and Fis1 is transient and dynamic, cells were treated with the crosslinker, DSP, (0.75 mM for 30 min), as described in a previous study (Yoon et al., 2003, *Mol Cell Biol* 23:5409-5420). The cells were lysed in total cell lystes (50 mM Tris-HCl, pH 7.5, containing 150 mM NaCl, 1% Triton X-100, and protease inhibitor).

Immunoprecipitates were analyzed by SDS-PAGE and immunoblotting with antibodies to Drp1, VDAC, and Fis1. VDAC was used as a loading control Mitochondria isolated from mouse liver were incubated with recombinant Drp1 (GST-Drp1). Drp1 bound to mitochondrial preparation and only P110 (1 µM) reduced this association by >60% (p<0.01, FIG. 2C); peptide carrier TAT$_{47-57}$ or the other Drp1-derived peptides had no effect. The mitochondrial membrane protein VDAC was used as marker and loading control.

In another set of experiments, Drp1 was incubated with Fis1 and the complex was immunoprecipitated using anti-Drp1 antibody followed by immunoblotting with anti-Fis1 antibody. For direct binding between Drp1 and Fis1, recombinant Drp1 (50 ng) and Fis1 (50 ng) were incubated in PBS containing 1 mM DSP for 30 min in the presence or absence of Drp1/Fis1 peptides (1 µM each) or control peptide TAT. After termination of the reaction by 50 mM Tris-HCl, pH 7.5, reaction mixtures were subjected to immunoprecipitation with anti-Fis1 antibody in the presence of 1% Triton X-100. Immunoprecipitates were washed with PBS containing 1% Triton X-100 and analyzed by SDS-PAGE and subsequent immunoblotting with antibodies to Fis1 and Drp1.

Figures 2D, 2E:
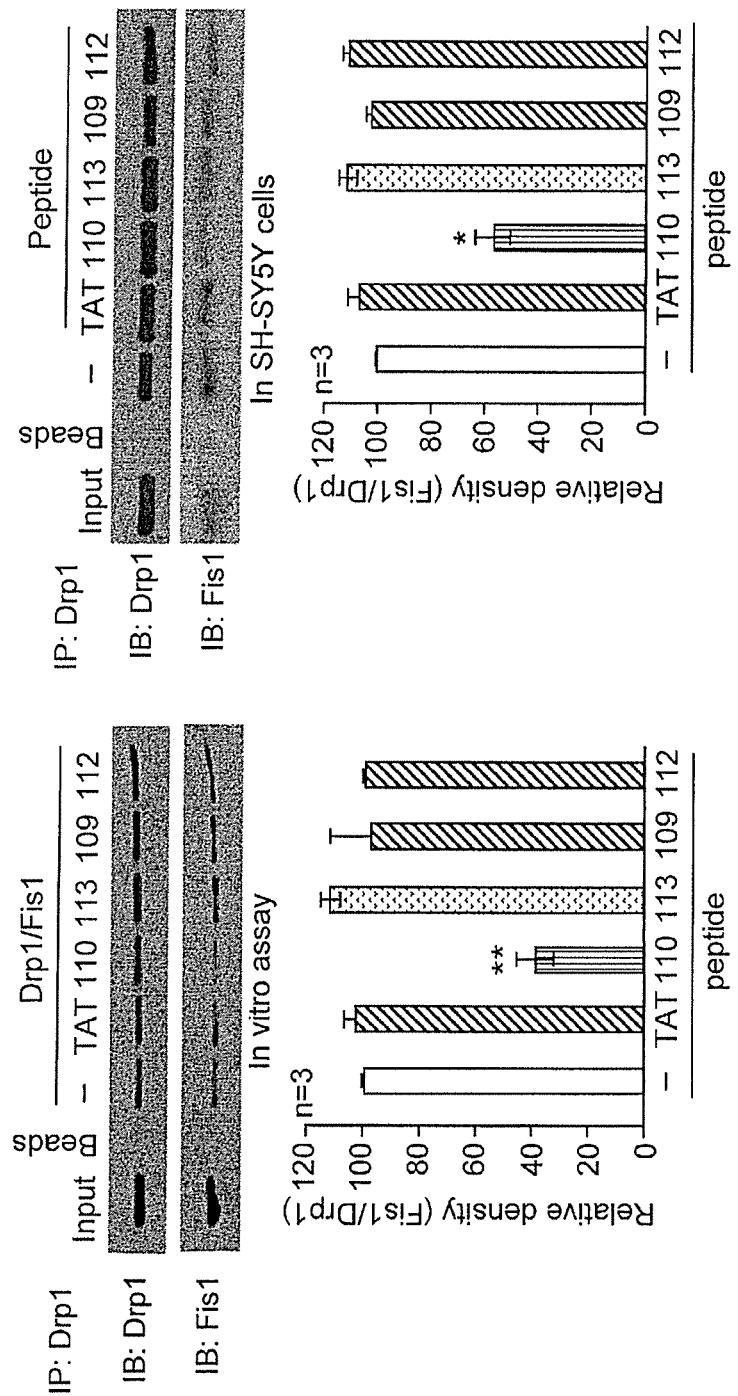
FIG. 2D shows the effects of mitochondrial fission inhibitor constructs on interaction of Drp1 with Fis1. The top panel is a western blot; the bottom panel is a quantitative representation of the western blot.
FIG. 2E shows the effects of mitochondrial fission inhibitor constructs on interaction of Drp1 with mitochondria. The top panel is a western blot; the bottom panel is a quantitative representation of the western blot.
Figure 2F:
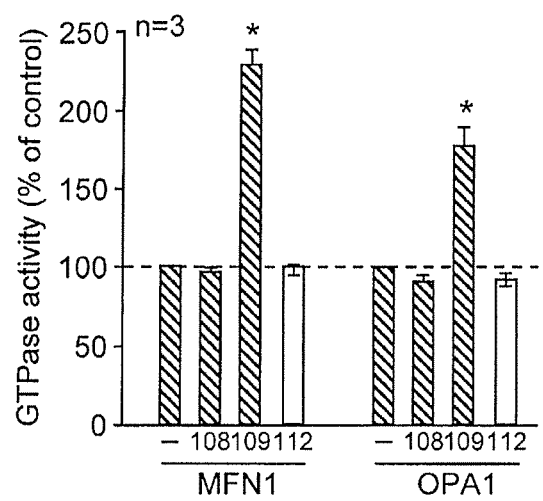
FIG. 2F shows the effects of a mitochondrial fission inhibitor construct on Drp1 GTPase activity in the presence of MFN1 and OPA1.

Drp1 bound Fis1 in this assay and this interaction was blocked by the addition of P110 but not by other peptides (FIG. 2D). Inhibition of the interaction between Drp1 and Fis1 by peptide P110 was also observed in the cultured SH-SY5Y neuronal cells (FIG. 2E). Again, other peptides have no effect on blocking the interaction.

P110 was further characterized to determine its effect on Drp1 activity and functions in cell culture.

Example 4

Effects of Mitochondrial Fission Inhibitor Construct on Drp1 Translocation

Drp1 translocation from cytosol to the mitochondria is a hallmark of mitochondrial fission. Experiments were done to determine if P110 can inhibit translocation of Drp1 to the mitochondria in cultured human neuroblastoma, SH-SY5Y cells.

Cultured human SH-SY5Y neuronal cells were treated with peptide P110 (1 µM) for 30 min prior to 1 hr incubation in the absence or presence of MPP+ (1-methyl-4-phenylpyridinium, a specific mitochondrial complex I inhibitor) (2 mM) or CCCP (carbonyl cyanide m-chloro phenyl hydrazone) (10 µM). Western blot analysis of mitochondrial fractions was determined by the indicated antibodies. VDAC was used as a loading control.

Figure 3A:
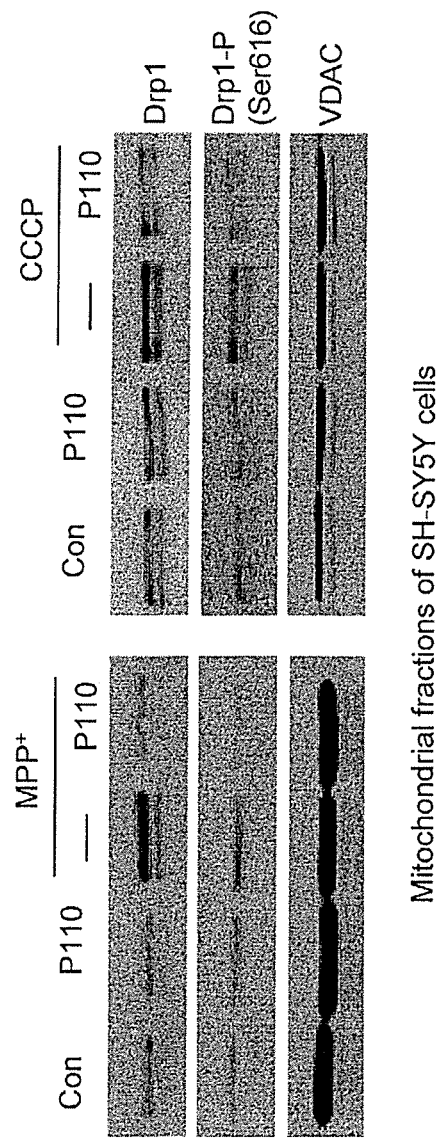
FIG. 3A shows western blots in which mitochondria membrane preparations were probed for the presence of proteins upon treatment with or without a mitochondrial fission inhibitor construct, and in the presence or absence of induced stress.
Figure 3B:
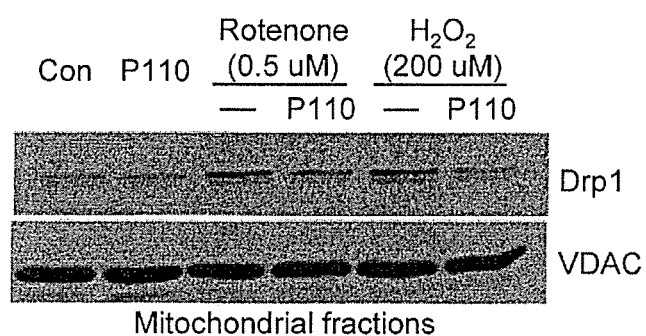
FIG. 3B shows a western blot in which mitochondria membrane preparations were probed for the presence of proteins upon treatment with or without a mitochondrial fission inhibitor construct, and in the presence or absence of induced stress.

SH-SY5Y cells were treated with MPP+, a neurotoxin causing PD, CCCP, a mitochondrial uncoupler (FIG. 3A), $H_2O_2$ (hydrogen peroxide, oxidative stress, FIG. 3B) or rotenone (a mitochondrial complex I inhibitor and a neurotoxin causing PD, FIG. 3B). Treatment with P110 abolished the increased levels of Drp1 associated with the mitochondrial fractions under all these stress conditions, suggesting that P110 blocked Drp1 translocation to the mitochondria induced by a wide range of stimuli.

In another experiment, mitochondria were isolated from SH-SY5Y neuronal cells exposed to MPP+ in the absence or presence of P110. Mitochondrial fractions were subjected to Western blot analysis. The levels of Drp1, Fis1, Mff, Mfn1 (mitofisin1) and OPA1 in the mitochondrial fractions were determined. Voltage-dependent ion channel (VDAC), a marker of mitochondria, was used as internal loading controls. Quantitative data from three independent experiments are provided a the histogram, with data shown as mean±S.E (FIG. 3D).

Figure 3C:
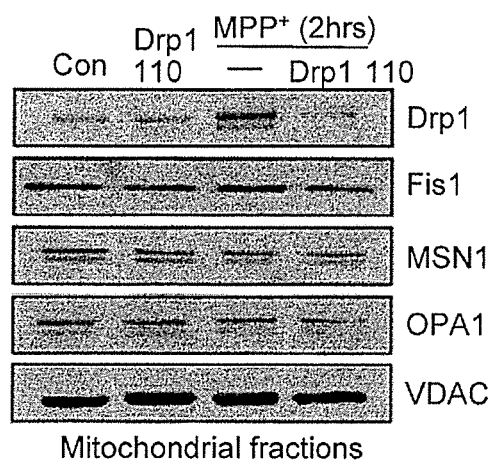
FIG. 3C shows a western blot in which mitochondria membrane preparations were probed for the presence of proteins upon treatment with or without a mitochondrial fission inhibitor construct, and in the presence or absence of induced stress.
Figure 3D:
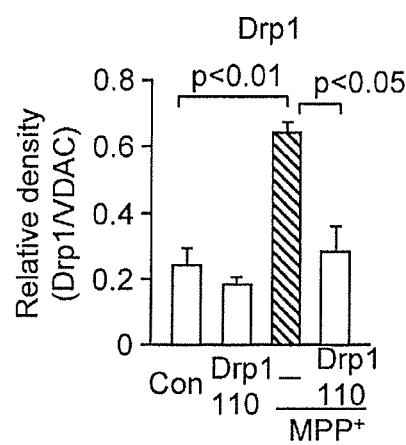
FIG. 3D shows a quantitative representation of Drp1 in mitochondrial membranes upon treatment with or without a mitochondrial fission inhibitor construct, and in the presence or absence of induced stress.

Treatment with P110 reduced MPP+-induced translocation of Drp1 from cytosol to the mitochondria by more than 60% ($p<0.01$, n=3), but did not affect the cellular level and distribution of other mitochondrial dynamics-related proteins, including mitofusin-1 and -2 (MFN-1/2), OPA1 and Fis1 (FIGS. 3C and 3D).

Figure 3E:
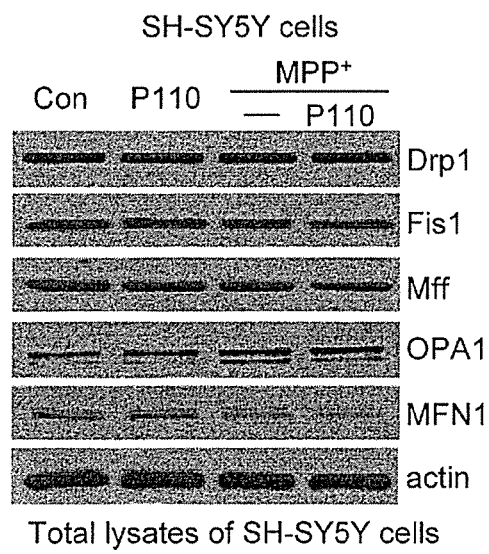
FIG. 3E shows a western blot in which mitochondria membrane preparations were probed for the presence of proteins upon treatment with or without a mitochondrial fission inhibitor construct, and in the presence or absence of induced stress.
Figure 3F:
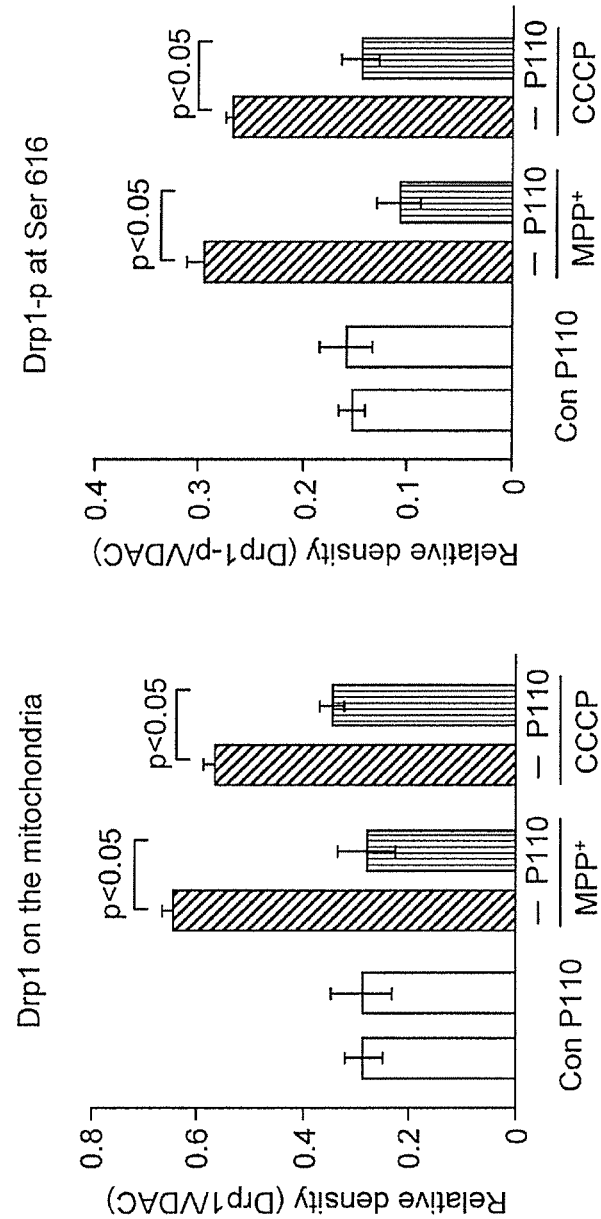
FIG. 3F shows a quantitative representation of phosphorylation of Drp1 upon treatment with or without a mitochondrial fission inhibitor construct, and in the presence or absence of induced stress. Left panel: phosphorylation of wildtype Drp1; Right panel: phosphorylation of a Drp1 having a Ser616 mutation.

The function of Drp1 is regulated at least in part by phosphorylation events. Previous studies demonstrated that Drp1 phosphorylation at Ser616 results in increased Drp1 fission activity and promotes mitochondrial fragmentation (Qi et al., 2011, *Mol Biol Cell* 22:256-265). As shown in FIG. 3F, P110 treatment abolished Ser616 phosphorylation in cultured SH-SY5Y neuronal cells exposed to either MPP+ or CCCP. Note that treatment with P110 did not affect Drp1 levels and phosphorylation under normal conditions (FIGS. 3A and 3B) and that no changes in the total levels of Drp1 or other proteins associated with mitochondrial fusion and fission were observed in any of the treatment groups (FIG. 3E). Together these data confirm selectivity of P110 for Drp1.

The effects of MPP+or CCCP on translocation of Drp1 in the absence and presence of P110 was measured using confocal microscopy. Cultured SH-SY5Y cells in black 96-well plate were treated with Drp1 peptide inhibitor P110 (1 µM) 30 min prior to treatment of MPP+ (2 mM) or CCCP (5 uM). After 2 hrs of treatment, cells were stained with MITOSOX™ (red mitochondrial superoxide indicator) (5 uM, for 10 min, mitochondrial ROS) or TMRM (0.5 uM, for 20 min, MMP) at 37° C. For total ROS detection, cells were treated with MPP+ or CCCP for 24 hrs. ROS level was measured by CM-H2DCFDA (1 µM for 30 min, Invitrogen). Cells were washed with PBS for three times. The detection was performed in a fluorescence microplate reader (Tecan, Infinite M1000) according to manufacturer's instructions. Measurements were normalized to the cell number counted using Hoechst staining.

Figure 3G:
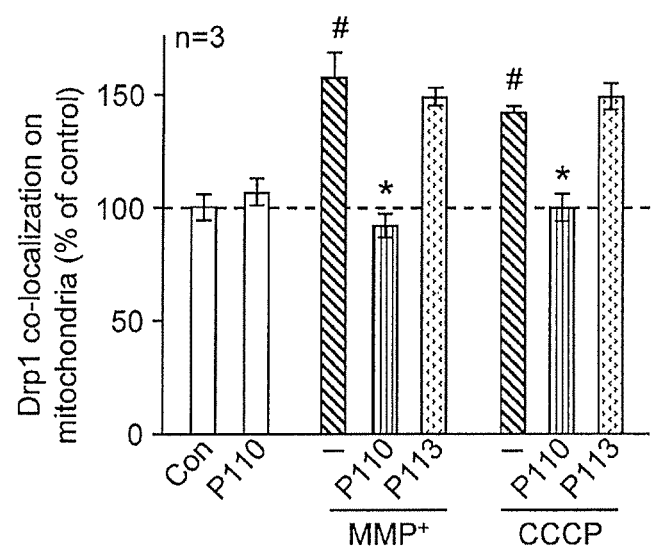
FIG. 3G shows a quantitative representation of Drp1 in mitochondrial membranes upon treatment with or without a mitochondrial fission inhibitor construct, and in the presence or absence of induced stress.

Confocal imaging analysis demonstrated that Drp1 is localized on the mitochondria after SH-SY5Y neuronal cells were exposed to MPP+ or CCCP. By contrast, P110 treatment greatly reduced this co-localization. The data, quantitated by Image J software, is provided in a histogram FIG. 3G. These results show that peptide P110 inhibited Drp1 association with the mitochondria as well as the enzymatic activity of Drp1, and support the conclusion that peptide P110 is a specific inhibitor Drp1.

Example 5

Effects of Modulator Peptides on Mitochondrial Morphology

Figure 4A:
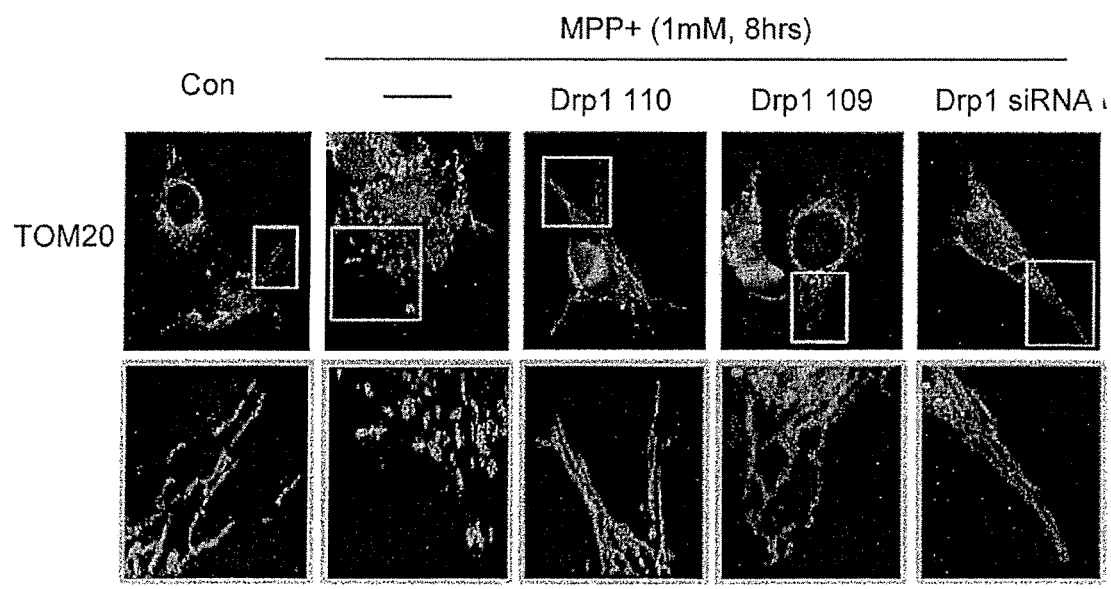
FIG. 4A shows confocal microscopy photographs of mitochondria after treatment with mitochondrial fission inhibitor constructs.
Figure 4B:
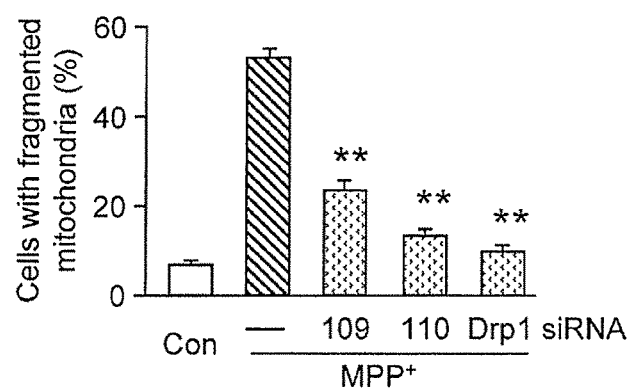
FIG. 4B provides quantitative analysis of the confocal microscopy results provided in FIG. 4A.

To determine effects of P110 on mitochondrial morphology in response to mitochondrial stresses, an immunostaining approach was used. In one experiment, SH-SY5Y neuronal cells were treated with Drp1 peptides or Drp1 siRNA followed by treatment of MPP+. The cells were then stained with TOM20 and Hoechst stain. As presented in FIGS. 4A and 4B, (the percentage of cells with fragmented mitochondria relative to the total number of cells presented as the mean±S.E. of three independent experiments. **, $p<0.01$; at least 200 cells per group were counted), treatment with P109 and P110 reduced mitochondrial fragmentation in the cultured cells exposed to MPP+ by 70% ($p<0.01$, n=3), similar to the reduction achieved by Drp1 siRNA treatment under the same condition. Importantly, treatment with these novel peptide inhibitors had no effect on mitochondrial morphology in control cells.

In another experiment, cultured SH-SY5Y cells were treated with P110 (1 µM) for 30 min followed by incubation with MPP+ (2 mM, 4 hrs) or CCCP (5 uM, 30 min). The cells were then stained with anti-Tom 20 antibody (green) and Hoechst stain (scale bar 0.5 µm). Mitochondrial morphology was analyzed using 6333 oil lens. The data were analyzed and are presented as a histogram in which the percentage of cells with fragmented mitochondria relative to the total number of cells is presented as the mean±S.E. of 3 independent experiments. At least 200 cells per group were counted.

Figure 5:
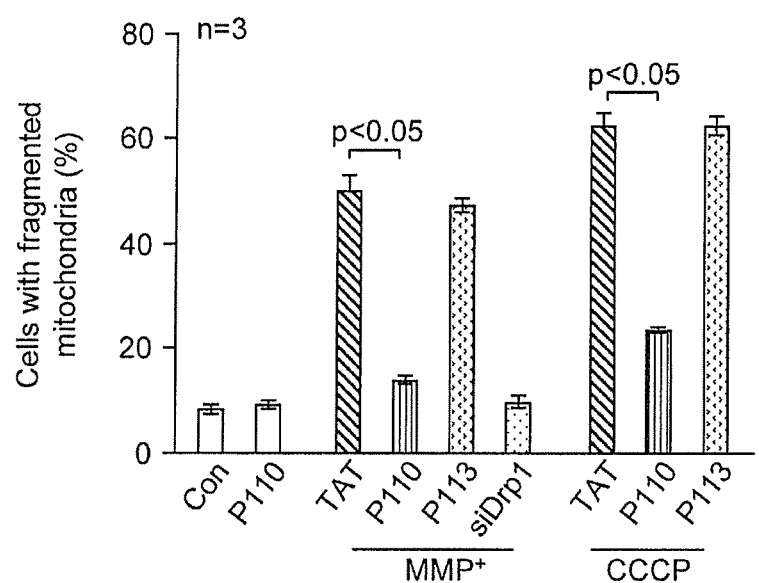
FIG. 5 provides quantitative data regarding mitochondrial fragmentation as affected by treatment with mitochondrial fission inhibitor constructs under non-stressed and stressed conditions.

As depicted in FIG. 5, extensive mitochondrial fragmentation was observed. The fragmentation visualized by confocal microscopy was featured by small, round or dot-like staining pattern in the cultures exposed to MPP+ or CCCP treatments, indicating that mitochondrial network was disrupted and fragmented. By contrast, mitochondrial fragmentation was greatly reduced by the treatment with Drp1 peptide inhibitor P110 in cells exposed to MPP+ (50% to 14%, $p<0.05$) and CCCP (63% to 23%, $p<0.05$), respectively. The extent of inhibition of mitochondrial fragmentation by P110 treatment was similar to that from the group treated with Drp1 siRNA under the same conditions. Interestingly, in the control cells incubated with P110, we did not observe dramatic difference on mitochondrial network as compared with control cells (FIG. 5). Given that P110 treatment did not affect Drp1 under normal conditions, we proposed that the peptide inhibitor P110 might have greater impact on Drp1 under pathological conditions in which Drp1 is hyper-activated.

Example 6

Effects on Mitochondrial ROS Production

Drp1-dependent mitochondrial fission impairment has been shown to occur during the early stage of mitochondrial dysfunction (Barsoum et al., 2006, *EMBO J* 25:3900-3911; Yuan et al., 2007, *Cell Death Differ* 14:462-471). Experiments were done to determine if P110 affects mitochondrial dysfunction as measured by the production of reactive oxygen species (ROS) under stress conditions and the effects on membrane potential.

SH-SY5Y cells were treated with P110 (1 µM) followed by incubation of MPP+ (2 mM) for 2 hrs. Mitochondrial superoxide production was determined using the mitochondrial superoxide indicator, MITOSOX™ red (red mitochondrial superoxide indicator). Nuclei were stained with Hoechst (blue). This experiment included the analysis of P110 alanine-scan analogs, further determine the contribution of each of the amino acids of the P110 fission inhibitor peptide sequence on the bioactivity of the peptide. The resultant sequences are shown here:

```
                            (SEQ ID NO: 24)
YGRKKRRQRRRGGaLLPRGS (SEQ ID NO: 25)
YGRKKRRQRRRGGDaLPRGS (SEQ ID NO: 26)
YGRKKRRQRRRGGDLaPRGS (SEQ ID NO: 27)
YGRKKRRQRRRGGDLLaRGS (SEQ ID NO: 28)
YGRKKRRQRRRGGDLLPaGS (SEQ ID NO: 29)
YGRKKRRQRRRGGDLLPRaS (SEQ ID NO: 30)
YGRKKRRQRRRGGDLLPRGa.
```

Figure 6A:
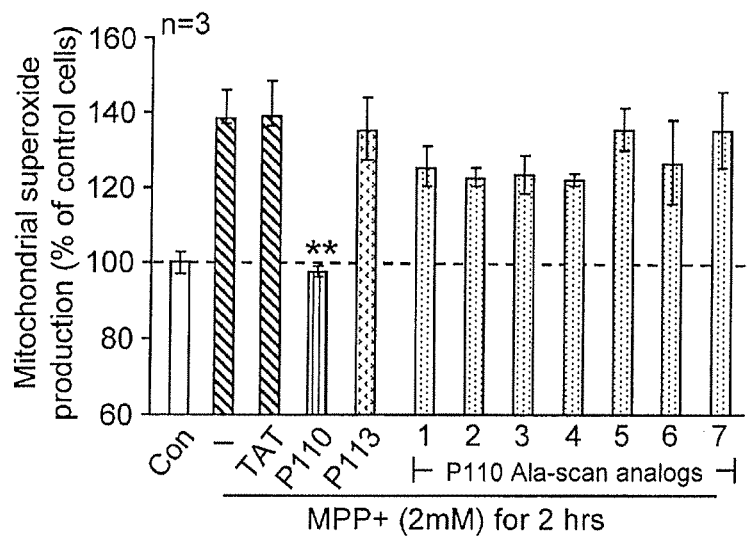
FIG. 6A provides quantitative data regarding superoxide production as affected by treatment with mitochondrial fission inhibitor constructs under stressed conditions.

The data are shown as a quantitative histogram of red fluorescence (FIG. 6A). P110 Ala-scan analogs were tested in the same assay, 1 µM each.

Figure 7:
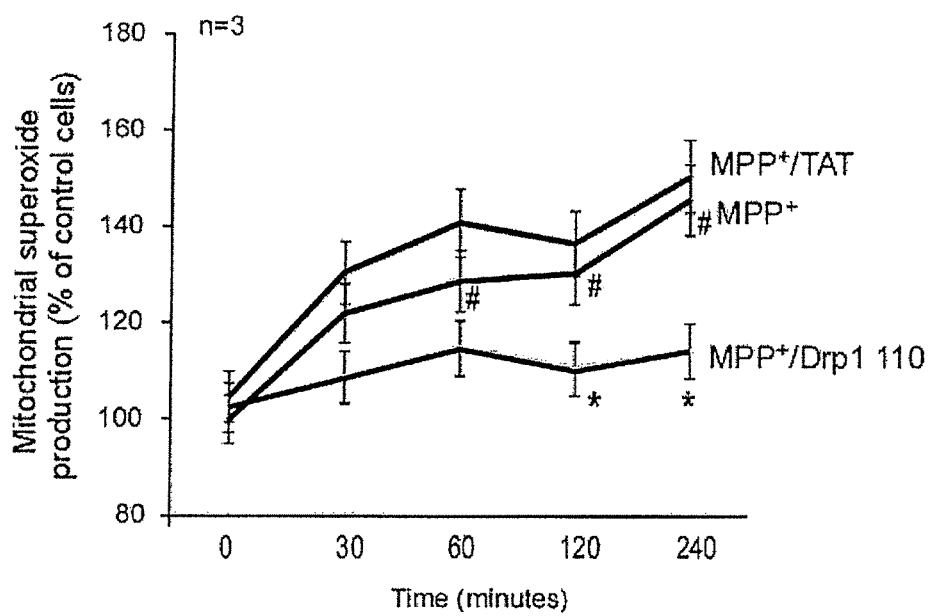
FIG. 7 shows effects of a mitochondrial inhibitor construct on mitochondrial superoxide production.

In cultures, treatment of SH-SY5Y cells with P110 abolished MPP+-induced production of mitochondrial superoxide, a major resource of mitochondrial ROS (FIG. 6A and FIG. 7). The Alan-scan analogs of P110 had limited or no activity relative to the effects of P110 on mitochondrial ROS production (FIG. 6A), suggesting that each of the 7 amino acids of the fission inhibitor peptide sequence (SEQ ID NO:12) of construct P110 contribute to the biological effects of the peptide.

Figure 6B:
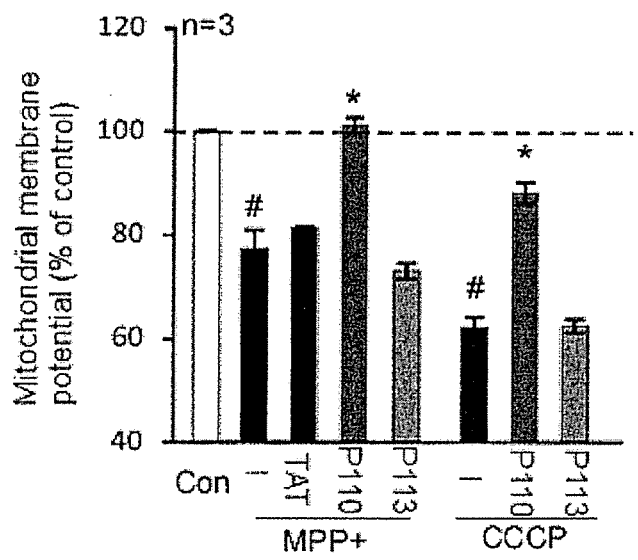
FIG. 6B shows effects on mitochondrial membrane potential by treatment with mitochondrial fission inhibitor constructs under stressed conditions.

Mitochondrial membrane potential was also determined using TMRM (tetramethylrhodamine methylester). Fifty µg of mitochondria were incubated with recombinant Drp1 (50 ng) followed by incubation with TMRM (0.5 µM) in the presence or absence of P110 (1 µM) or NAC (2.5 mM). Fluoresence detection was performed using black 96-well plates in a fluorescence microplate reader at 560 nm excitation and 690 nm emission and potential was assessed by quenching of the fluorescent signal. The data are presented as mean±S.E. of percentage relative to control mitochondria from three independent experiments (FIG. 6B, #, p<0.05 vs. control cells; *, p<0.05; **, P<0.01 vs. MPP+- or CCCP-treated cells). Isolated mouse liver mitochondria (50 µg) were incubated with Drp1 recombinant protein (50 ng) in the presence or absence of P110 (1 µM). A kinetic change of mitochondrial superoxide production was determined by using MITOSOX™ (red mitochondrial superoxide indicator). The data are presented as mean±S.E. of percentage relative to the value at basal level from three independent experiments (FIG. 6C, #, p<0.05 vs. control mitochondria; *, p<0.05 vs. mitochondria with the addition of Drp1). Mitochondrial membrane potential of isolated mouse liver mitochondria was determined by TMRM, as described above, in the indicated groups. NAC (2.5 mM) was used as a positive control (FIG. 6D). Protein levels of cytochrome c in the mitochondria were determined by western blot analysis with anti-cytochrome c antibodies in the indicated groups (insert, FIG. 6D). Total ROS production was determined by staining SH-SY5Y cells with CM2HDCFA (1 µM 30 min at 37° C.) in the indicated groups. The data are presented as mean±S.E. of percentage relative to control group from three independent experiments (FIG. 6E, *, p<0.05 vs. either MPP+ or CCCP treated-group; #, p<0.05 vs. control group).

Treatment with P110 significantly recovered mitochondrial membrane potential (MMP) in the presence of MPP+ or CCCP (FIG. 6B) and improved the assembly of the mitochondrial electron transport chain (ETC) (FIG. 8) in the cultured SH-SY5Y cells treated with MPP+.

Figure 8:
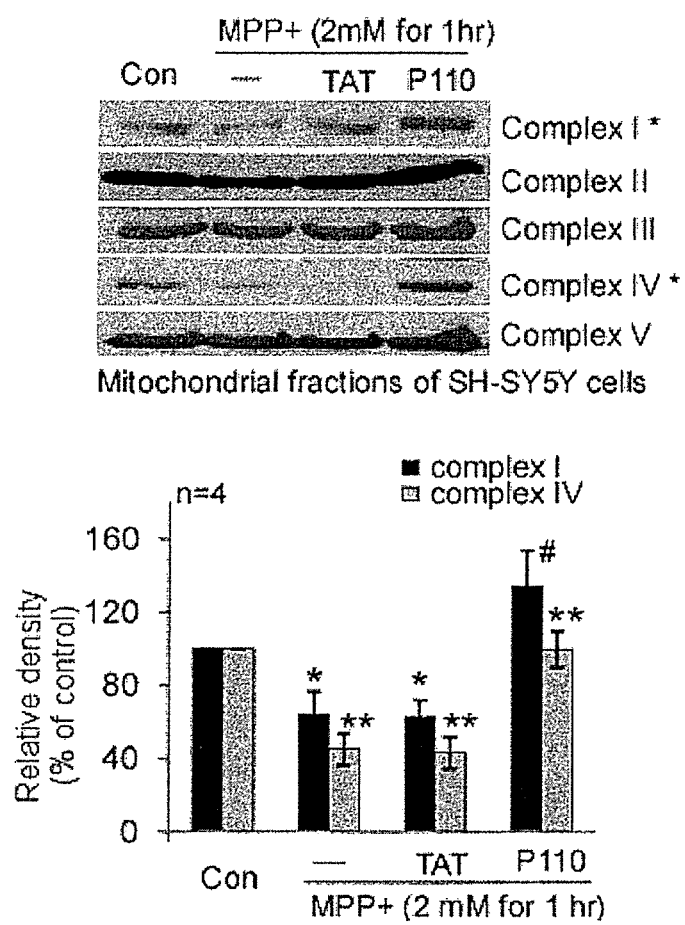
FIG. 8 shows the effects of a mitochondrial inhibitor construct on mitochondrial complex assembly under stressed conditions. Top panel: western blot in which probes detected complex I-V; bottom panel: quantitative data obtained from the western blot of the top panel. (*$p<0.05$ vs. MPP+-treated cells; **$p<0.01$ vs. MPP+-treated cells; #$p<0.05$ vs. control cells).

The oxidative phosphorylation system in the mitochondria is responsible for generating ATP and consists of five major membrane protein complexes, the mitochondrial complexes I-V. MPP+ is a specific mitochondrial complex I inhibitor. P110 was tested for potential effects on MPP+-induced defects in mitochondrial complexes. As shown in FIG. 8, in cultured SH-SY5Y cells, MPP+ treatment disassembled complex I and IV, as evidenced by the reduction of NDUFB8 (component of complex I) and MTCOI (component of complex IV). By contrast, treatment of P110 under the same conditions abolished the reduction of these two proteins, suggesting that P110 treatment recovered MPP+-induced oxidative phosphorylation defect and mitochondrial integrity. The upper panel of FIG. 8 shows the western blot. The lower panel is a histogram in which the quantitative data generated from the western blot are expressed as mean±S.E. of 3 independent experiments.

To determine the direct effects of activated Drp1 on the mitochondria, Drp1 was incubated with isolated mouse liver mitochondria. Using the approach as in (Johnson-Cadwell et al., 2007, *J Neurochem* 101:1619-1631), mitochondrial superoxide production was measured followed by the addition of Drp1 recombinant protein in the presence or absence of P110.

Figure 6C:
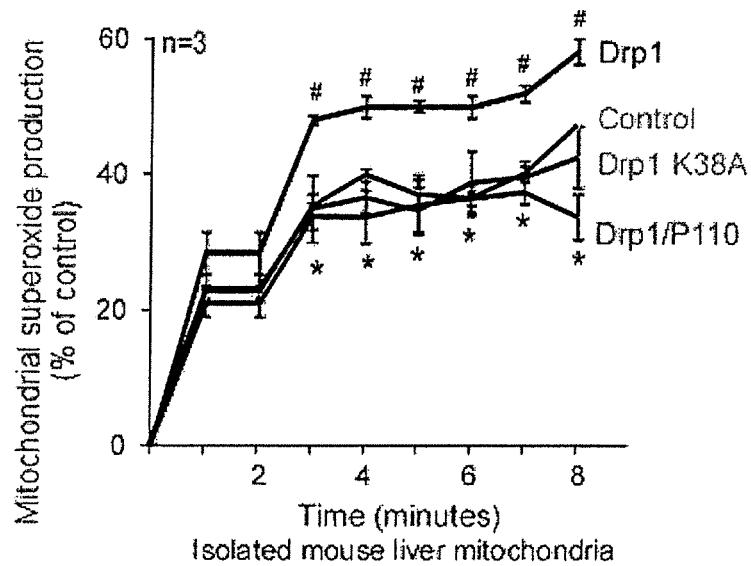
FIG. 6C shows effects on superoxide production by treatment with mitochondrial fission inhibitor constructs.
Figure 6D:
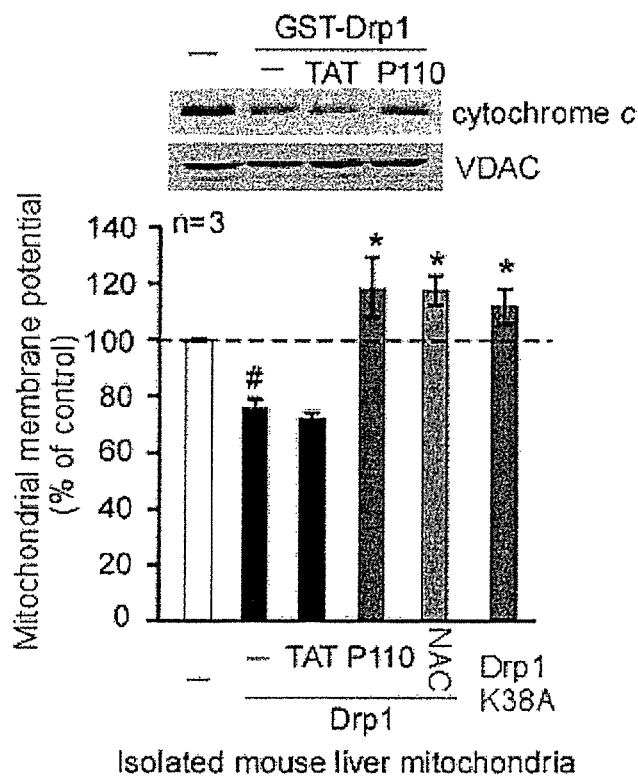
FIG. 6D shows a western blot indication effects of a mitochondrial inhibitor construct on cytochrome c release (top panel) and effects on mitochondrial membrane potential (bottom panel).

Interestingly, Drp1 addition triggered about a 50% increase in mitochondrial superoxide production over 8 minutes (p<0.05, n=3) relative to basal condition (FIG. 6C). Importantly, adding either P110 or the Drp1 dominant negative mutant, Drp1 K38A, abolished Drp1-induced ROS elevation in the mitochondria (FIG. 6c, p<0.05, n=3). These data suggest that activated Drp1 directly caused mitochondrial ROS production.

Further, after 8 min of Drp1 incubation with the mitochondria, the levels of cytochrome c in the mitochondria declined, an effect that was inhibited in the presence of P110 (FIG. 6D-top panel (western blot)), indicating that P110 inhibited cytochrome c release from the mitochondria under these condition. Cytochrome c release is one of the signs of mitochondrial membrane potential (MMP) dissipation.

Figure 6E:
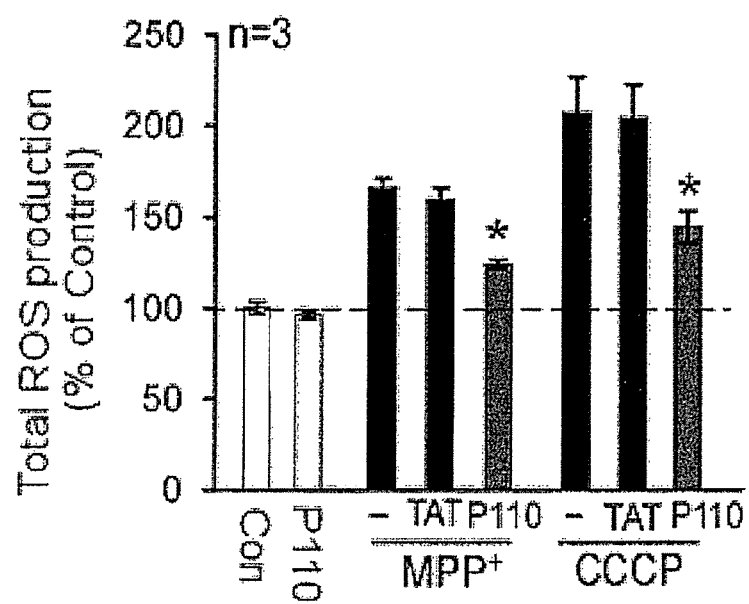
FIG. 6E shows effects of a mitochondrial inhibitor construct on total reactive oxygen species (ROS) production under stressed conditions.

The mitochondrial membrane potential of isolated mouse liver mitochondria was then measured in the presence or absence of P110. Drp1 addition caused a significant reduction of MMP, and treatment with P110 improved the MMP, similar to that of the Drp1 K38A-treated group (FIG. 6D, bottom panel). As expected, the anti-oxidant N-Acetyl cysteine (NAC), also prevented the dissipated MMP to the same extent as that of P110. Finally, treatment with P110 greatly reduced total ROS produced by the mitochondrial stressors, MPP+ and CCCP (FIG. 6E). Taken together, these data demonstrate that inhibition of stressor-induced hyper-activation of Drp1 by P110 reduced mitochondrial damages by suppressing mitochondrial ROS, improving mitochondrial membrane potential and mitochondrial integrity.

Example 7

Effects on Programmed Cell Death and Mitochondrial Integrity

Previous studies demonstrated that impairment of mitochondrial fission is closely linked with increased apoptosis and autophagic cell death in response to various stimuli through increasing mitochondrial depolarization and ROS (Wikstrom et al., 2009, *Int J Biochem Cell Biol* 41:1914-1927). Moreover, Drp1 hyperactivation on the mitochondria has been recently demonstrated to participate in TN Fα-induced necrotic cell death (Wang et al., 2012, *Cell* 148:228-243). Thus, Drp1-dependent mitochondrial dysfunction may represent a convergent point of several programmed cell death (PCD) pathways. Experiments were performed to determine if P110 affects programmed cell death under stress conditions by inhibiting aberrant mitochondrial fission.

SH-SY5Y neuronal cells were treated with P110 followed by the exposure to MPP+ (2 mM for 1 hour). Active form of Bax (NT-Bax), cytochrome c and Bcl-2 on the mitochondria were determined by western blot analysis with the indicated antibodies. Shown are representative data of three independent experiments. Quantification of the data are provided as mean±SE of three independent experiments.

Figure 9A:
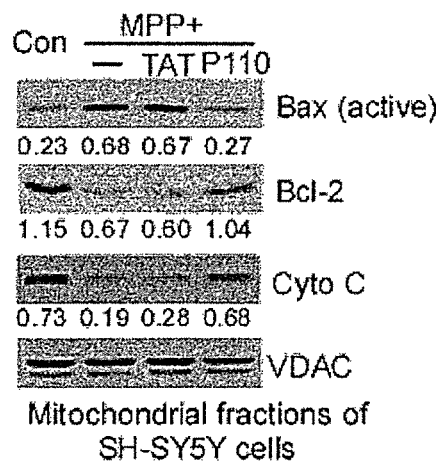
FIG. 9A shows a western blot showing the effects of a mitochondrial fission inhibitor construct on apoptosis marker levels under a stressed condition.
Figure 9B:
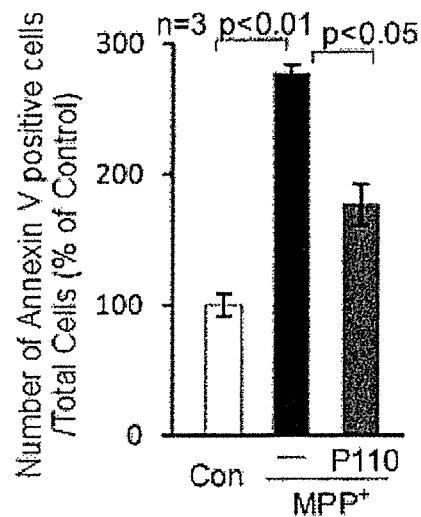
FIG. 9B shows the effects of a mitochondrial fission inhibitor construct on levels of an apoptosis marker under a stressed condition.

P110 treatment inhibited early stages of apoptosis as shown by the greatly reduced accumulation of active Bax on the mitochondria, blocked the release of cytochrome c from the mitochondria and improved decreased Bcl-2 levels on the mitochondria in cultured SH-SY5Y neuronal cells treated with MPP+ (FIG. 9A). The number of apoptotic SH-SY5Y cells exposed to MPP+ was also greatly reduced by P110 treatment (FIG. 9B). Apoptosis was determined by annexin V staining 8 hours after MPP+ exposure. The number of apoptotic cells was expressed as mean±S.E. of percentage relative to total number of cells.

Figure 9C:
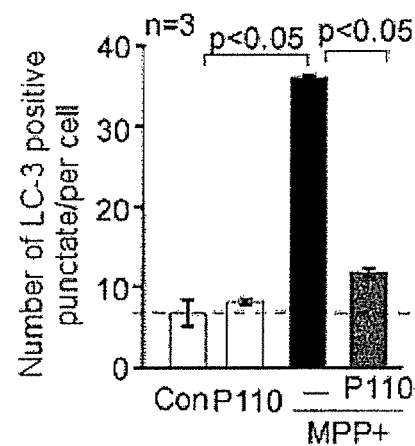
FIG. 9C shows the effects of a mitochondrial fission inhibitor construct on levels of an autophagic marker under a stressed condition.
Figure 9D:
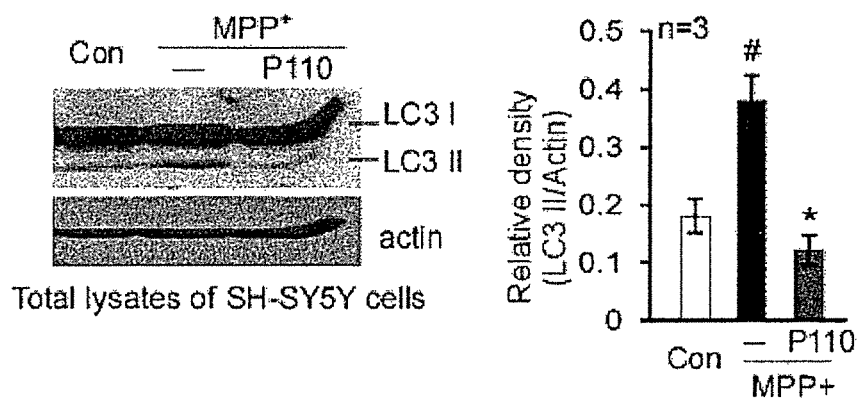
FIG. 9D shows the effects of a mitochondrial fission inhibitor construct on levels of an autophagic marker under a stressed condition. Left panel: western blot using a probe to detect LC3 I and LC3 II; right panel: quantitative data). (#$p<0.05$ vs. control group; *$p<0.05$, **$p<0.01$ vs. MPP+-treated cells)

Autophagy is another consequence of excessive mitochondrial fission (Twig et al., 2008, *EMBO J* 27:433-446; Wikstrom et al., 2009, *Int J Biochem Cell Biol* 41:1914-1927). Autophagy can be measured by the induction of the autophagic marker LC3 (microtubule-associated protein 1, light chain 3, also known as ATG8). Cultured SH-SY5Y cells were stained by anti-LC3 antibodies and nuclei were stained by Hoechsts staining. A histogram (FIG. 9C) depicts the number of LC3-positive punctate/per cell in the indicated groups. The data are presented as the mean±S.E. of three independent experiments. Western blot analysis of LC3 I/II with anti-LC3 antibodies is shown and is presented as a histogram where the data are expressed as mean±S.E. of three independent experiments (FIG. 9D, left panel).

Consistent with previous studies (Zhu et al., 2007, *Am J Pathol* 170:75-86), MPP+ caused excessive autophagy, as evidenced by the induction of autophagic marker LC3 (microtubule-associated protein 1, light chain 3, also known as ATG8). Treatment with P110 reduced the number of LC3-positive puncti in the cells and LC3 cleavage (LC3 I to LC3 II) (FIGS. 9C and 9D, right panel), suggesting an inhibition of excessive autophagy.

Cell viability of stressed SH-SY5Y cells was measured by MTT assay. SH-SY5Y cells were treated with MPP+ (2 mM for 24 hours) following treatment with TAT, P110 or P110 Ala-scan analogs (1 µM each) (FIG. 9E, #, p <0.05 vs. control group; *, p<0.05, **, p<0.01 vs. MPP+-treated cells).

Figure 9E:
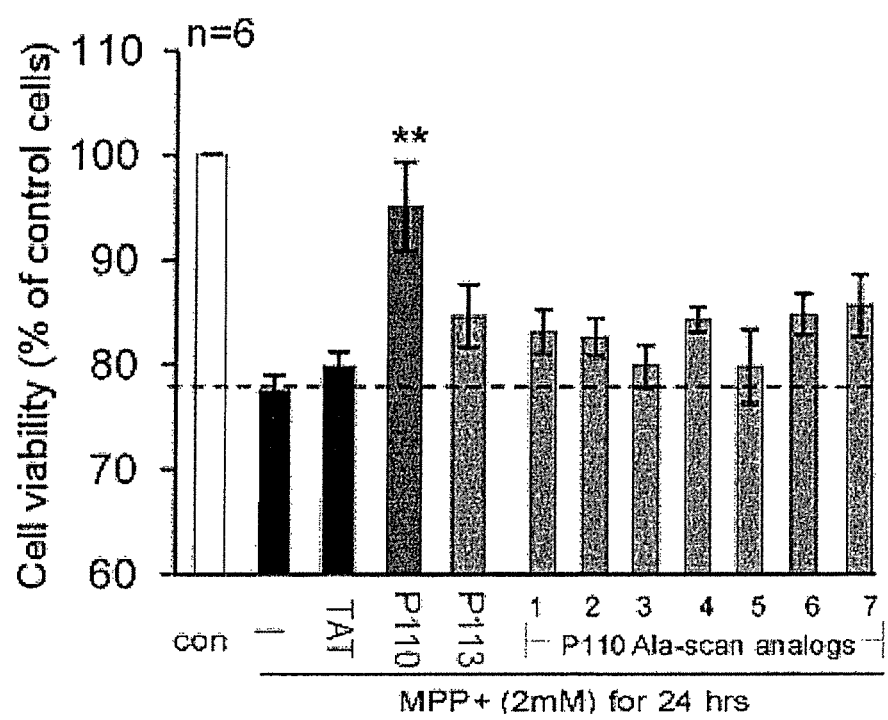
FIG. 9E shows the effects of mitochondrial fission inhibitor constructs on cell viability under stressed conditions. (**$p<0.01$ vs. MPP+-treated cells)

Reduction in the PCD by treatment with P110 was also associated with improved cell viability in cultured SH-SY5Y cells in response to stress (FIG. 9E). Consistent with results described above, treatment with P113 or the seven P110 Ala-scan analogs had no significant effect on cell viability under the same conditions (FIG. 9E). Together, the data are consistent with previous studies showing that Drp1 hyperactivation plays an active role in different types of cell death. Importantly, the selective mitochondrial fission inhibitor, P110, rescued cells from these cell death pathways.

In another experiment, Human SH-SY5Y cells were treated with Drp1 P108, P109 or P110 or Fis1 P111, P112 or P113 (0.5 µM) for 15 min followed by treatment with MPP+ (1 mM for 24 hrs). The cell viability was then determined by MTT test.

Figure 9F:
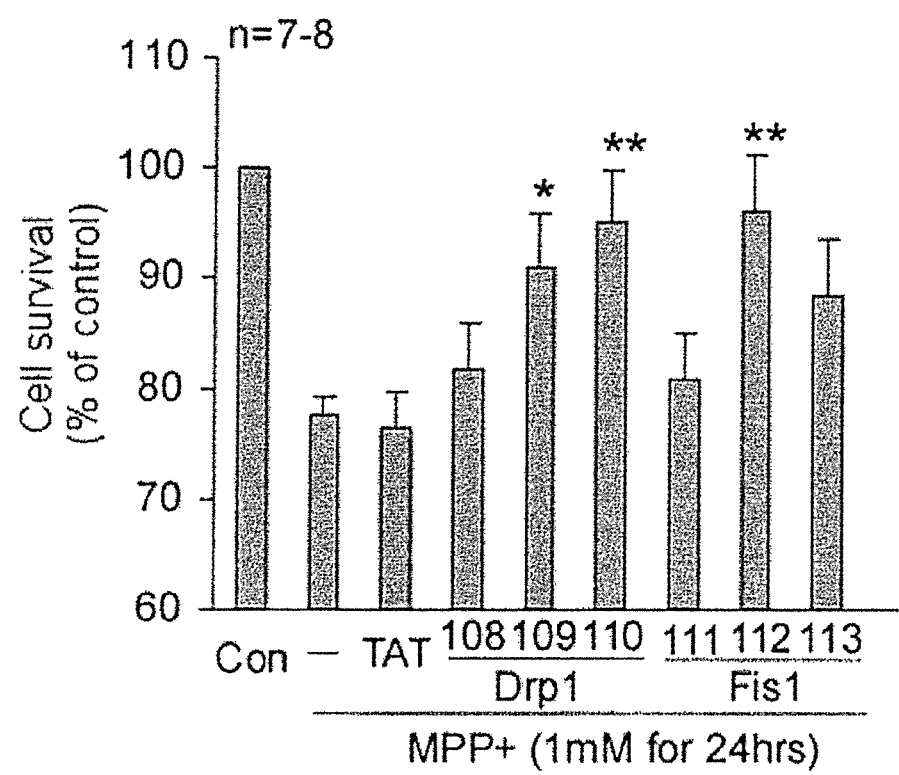
FIG. 9F shows the effects of mitochondrial fission inhibitor constructs on cell survival under stressed conditions. (*, $p<0.05$; **, $p<0.01$ vs. control)

Treatment with P109, P110, and P112 reduced mitochondrial damage and neuronal cell death (p<0.05 or p<0.01, n=7-8) that were triggered by MPP+ (1 mM for 24 hours). These peptides had no effects on mitochondrial health in control cells (Provisional FIG. 9F; *, p<0.05; **, p<0.01 vs. control cells, n=7-8).

Example 8

Effects on Neurite Degeneration of in a Parkinsonism Model

Aberrant mitochondrial fission has been highlighted in a number of neurodegenerative diseases, such as parkinsonism, indicating a potential mechanism by which mitochondrial dysfunction contributes to neurodegenerative diseases (Reddy et al., 2011, *Brain Res Rev* 67:103-118). MPP+ induces selective degeneration of dopaminergic neurons in a chemical experimental model of Parkinsonism. We therefore determined the effects of P110 treatment on the viability of primary dopaminergic neuronal cells in response to MPP+ exposure.

Primary rat dopaminergic neurons (cultured for 6 days) were treated without or with P110 (1 µM) followed by treatment with or without MPP+ (1 µM). Two hrs following MPP+ treatment, the cells were stained with MITOSOX™ red (to measure mitochondrial superoxide production) and anti-TH antibody (a marker of dopaminergic neurons). Fifteen hrs after MPP+ treatment, cells were stained with anti-TH antibody and anti-Tom20 antibody (a marker of mitochondria).

Figures 10A, 10B, 10C:
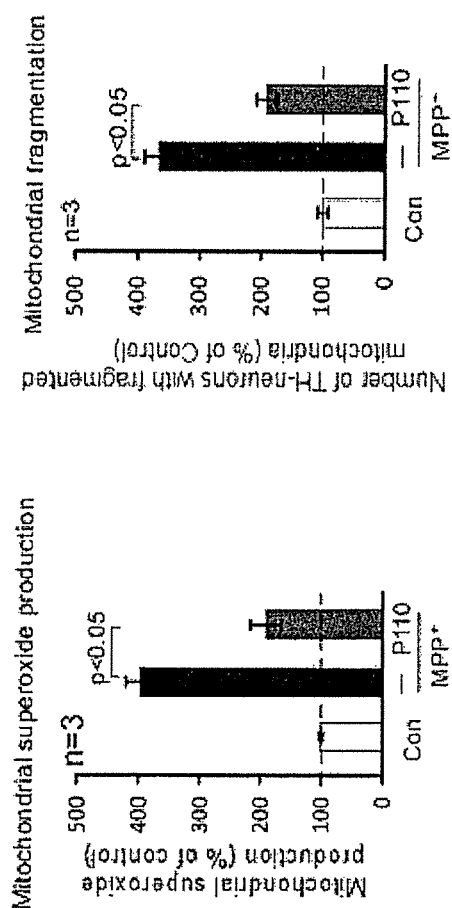
FIG. 10A shows effects of a mitochondrial fission inhibitor construct on mitochondrial superoxide production in a dopaminergic neuronal cell under stressed conditions.
FIG. 10B shows effects of a mitochondrial fission inhibitor construct on mitochondrial fragmentation in a dopaminergic neuronal cell under stressed conditions.
FIG. 10C shows effects of a mitochondrial fission inhibitor construct on neurite loss under stressed conditions.

Quantitative results are provided for mitochondrial superoxide production (FIG. 10A), mitochondrial fragmentation (FIG. 10B) and neurite loss (FIG. 10C) (as mean±SE of three independent experiments. Consistent with the findings above, treatment with P110 reduced mitochondrial fragmentation and mitochondrial ROS production in primary dopaminergic neurons exposed to MPP+. Importantly, P110 treatment reduced neurite loss of dopaminergic neurons, which were identified by tyrosine hydroxylase (TH), a marker of dopaminergic neurons (FIG. 10C). These data suggest that inhibition of Drp1-induced mitochondrial dysfunction by P110 decreased neuronal degeneration in a cell culture model of Parkinsonism.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for identifying an inhibitor of dynamin 1-like protein (Drp1) interaction with mitochondrial fission 1 protein (Fis1) comprising:
   incubating Drp1 with Fis1 and a test agent to form a test mixture;
   incubating Drp1 with Fis1 and a negative control agent which does not block Drp1 interaction with Fis1 to form a negative control mixture; and
   incubating Drp1 with Fis1 and a positive control agent which does block Drp1 interaction with Fis1 to form a positive control mixture, wherein the positive control agent is a peptide consisting of 7, 8 or 9 amino acids and having at least 80% amino acid sequence identity to SEQ ID NO:13;
   detecting the presence of a complex between Drp1 and Fis1 in each of the test, negative control, and positive control mixtures;
   wherein the presence of a complex between Drp1 and Fis1 in the negative control mixture and the absence of a complex between Drp1 and Fis1 in the test and positive control mixtures indicates that the test agent is an inhibitor of Drp1 interaction with Fis1.

2. The method according to claim 1, wherein the step of detecting the presence of a complex between Drp1 and Fis1 comprises immunoprecipitating each of the test, negative control and positive control mixtures by adding an antibody to each of the test, negative control and positive control mixtures wherein the antibody binds to Drp1 or Fis1 to form an immunoprecipitate; and
   measuring Drp1 and Fis1 in the immunoprecipitate, wherein
      when the antibody is an antibody that binds to Drp1, the absence of Fis1 in the test mixture immunoprecipitate indicates that the test agent is an inhibitor of Drp1 interaction with Fis1; and
      when the antibody is an antibody that binds to Fis1, the absence of Drp1 in the test mixture immunoprecipitate indicates that the test agent is an inhibitor of Drp1 interaction with Fis1.

3. The method according to claim 1, wherein the peptide inhibits a guanosine triphosphate phosphatase (GTPase) activity of the Dynamin 1-like protein (Drp1) (SEQ ID NO:1).

4. The method according to claim 1, wherein the positive control agent is SEQ ID NO:12 or SEQ ID NO:13.

5. The method according to claim 1, wherein the step of incubating Drp1 with Fis1 comprises incubating recombinant Drp1 with mitochondria and a cross-linker.

6. The method according to claim 5, wherein the mitochondria are isolated.

7. The method according to claim 5, wherein the cross-linker is dithiobis(succinimidyl propionate) (DSP).

8. The method according to claim 1, wherein the inhibitor is a peptide.

* * * * *